United States Patent
Purcell et al.

(10) Patent No.: US 12,350,155 B2
(45) Date of Patent: Jul. 8, 2025

(54) METHOD AND APPARATUS FOR MITRAL VALVE CHORD REPAIR

(71) Applicant: Pipeline Medical Technologies, Inc., Santa Rosa, CA (US)

(72) Inventors: Cameron Paul Purcell, Santa Rosa, CA (US); Gordon B. Bishop, Santa Rosa, CA (US); Trung Ho Pham, Santa Rosa, CA (US); Stephen R. McDaniel, San Rafael, CA (US); Hien Ngoc Lam, Santa Rosa, CA (US); Whittaker Ian Hamill, Santa Rosa, CA (US); Katie Nicole Riojas, Santa Rosa, CA (US)

(73) Assignee: Pipeline Medical Technologies, Inc., Newark, DE (US)

( * ) Notice: Subject to any disclaimer, the term of this patent is extended or adjusted under 35 U.S.C. 154(b) by 389 days.

(21) Appl. No.: 18/001,981

(22) PCT Filed: Jun. 2, 2021

(86) PCT No.: PCT/US2021/035423
§ 371 (c)(1),
(2) Date: Dec. 15, 2022

(87) PCT Pub. No.: WO2021/257278
PCT Pub. Date: Dec. 23, 2021

(65) Prior Publication Data
US 2023/0225865 A1 Jul. 20, 2023

Related U.S. Application Data

(60) Provisional application No. 63/040,389, filed on Jun. 17, 2020.

(51) Int. Cl.
*A61F 2/24* (2006.01)
*A61B 17/04* (2006.01)

(52) U.S. Cl.
CPC ........ *A61F 2/2457* (2013.01); *A61B 17/0401* (2013.01); *A61B 17/0467* (2013.01);
(Continued)

(58) Field of Classification Search
CPC ...... A61B 17/0401; A61B 2017/00243; A61B 2017/0464; A61B 2017/0409;
(Continued)

(56) References Cited

U.S. PATENT DOCUMENTS

| 4,969,870 A | 11/1990 | Kramer et al. |
| 5,329,923 A | 7/1994 | Lundquist |

(Continued)

FOREIGN PATENT DOCUMENTS

| CN | 101495049 | 7/2009 |
| CN | 101553190 | 10/2009 |

(Continued)

OTHER PUBLICATIONS

International Preliminary Report on Patentability received for PCT Patent Application No. PCT/US21/35423, mailed on Dec. 29, 2022, 11 pages.

(Continued)

*Primary Examiner* — Katherine M Shi
(74) *Attorney, Agent, or Firm* — Faegre Drinker Biddle & Reath LLP

(57) ABSTRACT

Methods and devices for transvascular prosthetic chordae tendinea implantation are disclosed. A catheter is advanced into the left atrium. From an atrium side, the catheter can be anchored to a superior surface of a mitral valve leaflet and a leaflet anchor can be advanced into the mitral valve leaflet to secure the mitral valve leaflet to a leaflet suture. A ventricular anchor is anchored to the wall of the ventricle to secure the ventricular wall to a ventricle suture. The leaflet (Continued)

suture and the ventricle suture may be tensioned and connected by a suture lock to form an artificial chordae.

20 Claims, 69 Drawing Sheets

(52) U.S. Cl.
CPC .... *A61F 2/2466* (2013.01); *A61B 2017/0409* (2013.01); *A61B 2017/0441* (2013.01); *A61F 2220/0016* (2013.01); *A61F 2220/0075* (2013.01); *A61F 2230/0091* (2013.01); *A61F 2250/0098* (2013.01)

(58) Field of Classification Search
CPC .... A61B 2017/0412; A61B 2017/0414; A61B 2017/0496; A61B 2017/00783; A61B 17/0469; A61B 2017/0441; A61B 2017/0649; A61B 2017/048; A61B 2017/06171; A61B 2017/0427; A61B 2017/0429; A61B 2017/043; A61B 2017/0435; A61B 2017/0437; A61B 17/0467; A61B 2017/00044; A61B 2017/00703; A61B 17/0483; A61B 17/0487; A61B 2017/003; A61B 2017/00738; A61B 2017/00862; A61B 2017/0451; A61B 2017/0453; A61B 2017/0456; A61B 2017/06095; A61B 2090/031; A61B 2090/3966; A61F 2/2457; A61F 2/2466; A61F 2220/0016; A61F 2220/0075; A61F 2230/0091; A61F 2250/0098

See application file for complete search history.

(56) References Cited

U.S. PATENT DOCUMENTS

| | | | |
|---|---|---|---|
| 5,456,708 A | 10/1995 | Doan et al. |
| 5,674,217 A | 10/1997 | Wahlstrom et al. |
| 6,269,819 B1 | 8/2001 | Oz |
| 6,458,107 B1 | 10/2002 | Ockuly |
| 6,461,366 B1 | 10/2002 | Seguin |
| 6,569,105 B1 | 5/2003 | Kortenbach et al. |
| 6,626,930 B1 | 9/2003 | Allen et al. |
| 6,629,534 B1 | 10/2003 | Goar et al. |
| 6,743,239 B1 | 6/2004 | Kuehn et al. |
| 6,752,813 B2 | 6/2004 | Goldfarb et al. |
| 6,770,083 B2 | 8/2004 | Seguin |
| 6,840,246 B2 | 1/2005 | Downing |
| 6,978,176 B2 | 12/2005 | Lattouf |
| 7,048,754 B2 | 5/2006 | Martin et al. |
| 7,083,628 B2 | 8/2006 | Bachman |
| 7,191,545 B2 | 3/2007 | Yi |
| 7,226,467 B2 | 6/2007 | Lucatero et al. |
| 7,288,097 B2 | 10/2007 | Seguin |
| 7,464,712 B2 | 12/2008 | Oz et al. |
| 7,563,267 B2 | 7/2009 | Goldfarb et al. |
| 7,604,646 B2 | 10/2009 | Goldfarb et al. |
| 7,608,091 B2 | 10/2009 | Goldfarb et al. |
| 7,632,308 B2 | 12/2009 | Loulmet |
| 7,635,386 B1 | 12/2009 | Gammie |
| 7,637,903 B2 | 12/2009 | Lentz et al. |
| 7,655,015 B2 | 2/2010 | Goldfarb et al. |
| 7,666,204 B2 | 2/2010 | Thornton et al. |
| 7,682,369 B2 | 3/2010 | Seguin |
| 7,736,388 B2 | 6/2010 | Goldfarb et al. |
| 7,871,368 B2 | 1/2011 | Zollinger et al. |
| 7,871,433 B2 | 1/2011 | Lattouf |
| 7,887,552 B2 | 2/2011 | Bachman |
| 7,914,515 B2 | 3/2011 | Heideman et al. |
| 7,914,545 B2 | 3/2011 | Ek |
| 8,075,570 B2 | 12/2011 | Bolduc et al. |
| 8,100,923 B2 | 1/2012 | Paraschac et al. |
| 8,172,872 B2 | 5/2012 | Osypka |
| 8,241,304 B2 | 8/2012 | Bachman |
| 8,252,050 B2 | 8/2012 | Maisano et al. |
| 8,273,054 B2 | 9/2012 | St. Germain et al. |
| 8,303,622 B2 | 11/2012 | Alkhatib |
| 8,382,829 B1 | 2/2013 | Call et al. |
| 8,394,113 B2 | 3/2013 | Wei et al. |
| 8,409,273 B2 | 4/2013 | Thornton et al. |
| 8,465,500 B2 | 6/2013 | Speziali |
| 8,475,472 B2 | 7/2013 | Bachman |
| 8,475,525 B2 | 7/2013 | Maisano et al. |
| 8,480,730 B2 | 7/2013 | Maurer et al. |
| 8,535,339 B2 | 9/2013 | Levin et al. |
| 8,545,551 B2 | 10/2013 | Loulmet |
| 8,545,553 B2 | 10/2013 | Zipory et al. |
| 8,603,066 B2 | 12/2013 | Heidman et al. |
| 8,690,939 B2 | 4/2014 | Miller et al. |
| 8,718,794 B2 | 5/2014 | Helland |
| 8,740,940 B2 | 6/2014 | Maahs et al. |
| 8,778,016 B2 | 7/2014 | Janovsky et al. |
| 8,814,824 B2 | 8/2014 | Kauphusman et al. |
| 8,852,213 B2 | 10/2014 | Gammie et al. |
| 8,940,042 B2 | 1/2015 | Miller et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,594 B2 | 2/2015 | Maisano et al. |
| 8,961,596 B2 | 2/2015 | Maisano et al. |
| 9,011,520 B2 | 4/2015 | Miller et al. |
| 9,023,065 B2 | 5/2015 | Bolduc et al. |
| 9,050,187 B2 | 6/2015 | Sugimoto et al. |
| 9,131,939 B1 | 9/2015 | Call et al. |
| 9,180,007 B2 | 11/2015 | Reich et al. |
| 9,198,649 B2 | 12/2015 | Karapetian et al. |
| 9,241,702 B2 | 1/2016 | Maisano et al. |
| 9,259,218 B2 | 2/2016 | Robinson |
| 9,277,994 B2 | 3/2016 | Miller et al. |
| 9,307,980 B2 | 4/2016 | Gilmore et al. |
| 9,314,242 B2 | 4/2016 | Bachman |
| 9,474,606 B2 | 10/2016 | Zipory et al. |
| 9,492,264 B2 | 11/2016 | Fifer et al. |
| 9,572,667 B2 | 2/2017 | Solem |
| 9,579,097 B2 | 2/2017 | Shluzas |
| 9,636,205 B2 | 5/2017 | Lee et al. |
| 9,636,224 B2 | 5/2017 | Zipory et al. |
| 9,668,860 B2 | 6/2017 | Kudlik et al. |
| 9,681,864 B1 | 6/2017 | Gammie et al. |
| 9,681,964 B2 | 6/2017 | MacKenzie |
| 9,693,865 B2 | 7/2017 | Gilmore et al. |
| 9,724,195 B2 | 8/2017 | Goodwin et al. |
| 9,750,493 B2 | 9/2017 | Robinson et al. |
| 9,788,948 B2 | 10/2017 | Gilmore et al. |
| 9,801,720 B2 | 10/2017 | Gilmore et al. |
| 9,814,454 B2 | 11/2017 | Sugimoto et al. |
| 9,877,833 B1 | 1/2018 | Bishop et al. |
| 9,907,547 B2 | 3/2018 | Gilmore et al. |
| 9,907,681 B2 | 3/2018 | Tobis et al. |
| 10,022,114 B2 | 7/2018 | Gilmore et al. |
| 10,039,643 B2 | 8/2018 | Gilmore et al. |
| 10,039,644 B2 | 8/2018 | Navia et al. |
| 10,052,095 B2 | 8/2018 | Gilmore et al. |
| 10,058,323 B2 | 8/2018 | Maisano |
| 10,076,327 B2 | 9/2018 | Ellis et al. |
| 10,076,658 B2 | 9/2018 | Hastings et al. |
| 10,130,791 B2 | 11/2018 | Heideman et al. |
| 10,159,571 B2 | 12/2018 | de Canniere |
| 10,206,673 B2 | 2/2019 | Maisano et al. |
| 10,213,291 B2 | 2/2019 | Berra et al. |
| 10,231,727 B2 | 3/2019 | Sutherland et al. |
| 10,238,491 B2 | 3/2019 | Tobis |
| 10,285,686 B2 | 5/2019 | Gammie et al. |
| 10,376,266 B2 | 8/2019 | Herman et al. |
| 10,543,090 B2 | 1/2020 | Griswold et al. |
| 10,548,733 B2 | 2/2020 | Purcell et al. |
| 10,595,994 B1 | 3/2020 | Christianson et al. |
| 10,617,523 B2 | 4/2020 | Purcell et al. |
| 10,624,743 B2 | 4/2020 | Keidar et al. |
| 10,660,753 B2 | 5/2020 | Pham et al. |

(56) References Cited

U.S. PATENT DOCUMENTS

| | | |
|---|---|---|
| 10,667,910 B2 | 6/2020 | Bishop et al. |
| 10,675,150 B2 | 6/2020 | Bishop et al. |
| 10,682,230 B2 | 6/2020 | Bishop et al. |
| 10,925,731 B2 | 2/2021 | Bishop et al. |
| 11,083,580 B2 | 8/2021 | Purcell et al. |
| 2003/0105519 A1 | 6/2003 | Fasol et al. |
| 2003/0120341 A1 | 6/2003 | Shennib et al. |
| 2003/0130598 A1 | 7/2003 | Manning et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0073216 A1 | 4/2004 | Lieberman |
| 2004/0097979 A1 | 5/2004 | Svanidze et al. |
| 2005/0119735 A1 | 6/2005 | Spence et al. |
| 2005/0177132 A1 | 8/2005 | Lentz et al. |
| 2005/0177180 A1 | 8/2005 | Kaganov et al. |
| 2005/0251210 A1 | 11/2005 | Westra et al. |
| 2007/0038230 A1 | 2/2007 | Stone et al. |
| 2007/0118151 A1 | 5/2007 | Davidson |
| 2007/0123979 A1 | 5/2007 | Perier et al. |
| 2007/0219565 A1 | 9/2007 | Saadat |
| 2008/0177281 A1 | 7/2008 | Weitzner et al. |
| 2008/0177304 A1 | 7/2008 | Westra et al. |
| 2008/0195126 A1 | 8/2008 | Solem |
| 2008/0228165 A1 | 9/2008 | Spence et al. |
| 2008/0228223 A1 | 9/2008 | Alkhatib |
| 2008/0288061 A1 | 11/2008 | Maurer et al. |
| 2008/0294188 A1 | 11/2008 | Appling et al. |
| 2009/0043153 A1 | 2/2009 | Zollinger et al. |
| 2009/0069847 A1 | 3/2009 | Hashiba et al. |
| 2009/0082828 A1 | 3/2009 | Ostroff |
| 2009/0088837 A1 | 4/2009 | Gillinov et al. |
| 2009/0287304 A1 | 11/2009 | Dahlgren et al. |
| 2009/0312790 A1 | 12/2009 | Forsberg et al. |
| 2010/0023118 A1 | 1/2010 | Medlock et al. |
| 2010/0161042 A1 | 6/2010 | Maisano et al. |
| 2010/0161043 A1 | 6/2010 | Maisano et al. |
| 2010/0249919 A1 | 9/2010 | Gillinov et al. |
| 2010/0280604 A1 | 11/2010 | Zipory et al. |
| 2011/0011917 A1 | 1/2011 | Loulmet |
| 2011/0022083 A1 | 1/2011 | DiMatteo et al. |
| 2011/0060407 A1 | 3/2011 | Ketai et al. |
| 2011/0106245 A1 | 5/2011 | Miller et al. |
| 2011/0257581 A1 | 10/2011 | Koziczynski et al. |
| 2011/0301698 A1 | 12/2011 | Miller et al. |
| 2012/0065464 A1 | 3/2012 | Ellis et al. |
| 2012/0116418 A1 | 5/2012 | Belson et al. |
| 2012/0116489 A1 | 5/2012 | Khairkhahan et al. |
| 2012/0158021 A1 | 6/2012 | Morrill |
| 2012/0172915 A1 | 7/2012 | Fifer et al. |
| 2013/0035757 A1 | 2/2013 | Zentgraf et al. |
| 2013/0046380 A1 | 2/2013 | Maisano et al. |
| 2013/0096672 A1 | 4/2013 | Reich et al. |
| 2013/0190741 A1 | 7/2013 | Moll et al. |
| 2013/0197575 A1 | 8/2013 | Karapetian et al. |
| 2013/0197577 A1 | 8/2013 | Wolf et al. |
| 2013/0197578 A1 | 8/2013 | Gregoire et al. |
| 2013/0253639 A1 | 9/2013 | Alkhatib |
| 2014/0142687 A1 | 5/2014 | De Canniere et al. |
| 2014/0142689 A1 | 5/2014 | De Canniere et al. |
| 2014/0243877 A9 | 8/2014 | Lee et al. |
| 2014/0243963 A1 | 8/2014 | Sheps et al. |
| 2014/0350417 A1 | 11/2014 | Van Bladel et al. |
| 2015/0032127 A1 | 1/2015 | Gammie et al. |
| 2015/0119979 A1 | 4/2015 | Maisano et al. |
| 2015/0182255 A1 | 7/2015 | Shivkumar |
| 2015/0230919 A1 | 8/2015 | Chau et al. |
| 2015/0250590 A1 | 9/2015 | Gries et al. |
| 2015/0313620 A1 | 11/2015 | Suri |
| 2015/0342737 A1 | 12/2015 | Biancucci et al. |
| 2015/0359632 A1 | 12/2015 | Navia et al. |
| 2016/0058557 A1 | 3/2016 | Reich et al. |
| 2016/0143737 A1 | 5/2016 | Zentgraf et al. |
| 2016/0174964 A1 | 6/2016 | Tobis |
| 2016/0192925 A1 | 7/2016 | Bachman |
| 2016/0228117 A1 | 8/2016 | Borden |
| 2016/0240941 A1 | 8/2016 | Stavrianoudakis |
| 2016/0256269 A1 | 9/2016 | Cahalane et al. |
| 2016/0262741 A1 | 9/2016 | Gilmore et al. |
| 2016/0310701 A1 | 10/2016 | Pai |
| 2016/0354082 A1 | 12/2016 | Oz et al. |
| 2016/0367367 A1 | 12/2016 | Maisano et al. |
| 2017/0042658 A1 | 2/2017 | Lee et al. |
| 2017/0079797 A1 | 3/2017 | Maisano et al. |
| 2017/0086975 A1 | 3/2017 | Gilmore et al. |
| 2017/0119368 A1 | 5/2017 | Solem |
| 2017/0135817 A1 | 5/2017 | Tylis et al. |
| 2017/0156719 A1 | 6/2017 | Tobis |
| 2017/0156861 A1 | 6/2017 | Longoria et al. |
| 2017/0202657 A1 | 7/2017 | Lee et al. |
| 2017/0202669 A1 | 7/2017 | Schaffner et al. |
| 2017/0252032 A1 | 9/2017 | Hiorth et al. |
| 2017/0258464 A1 | 9/2017 | Gammie et al. |
| 2017/0258588 A1 | 9/2017 | Zipory et al. |
| 2017/0258594 A1 | 9/2017 | Gilmore et al. |
| 2017/0273681 A1 | 9/2017 | Gilmore et al. |
| 2017/0304051 A1 | 10/2017 | Tobis et al. |
| 2017/0340433 A1 | 11/2017 | Berra et al. |
| 2017/0340443 A1 | 11/2017 | Stearns et al. |
| 2018/0064535 A1 | 3/2018 | Gilmore et al. |
| 2018/0185179 A1 | 7/2018 | Murphy et al. |
| 2018/0206992 A1 | 7/2018 | Brown |
| 2018/0221148 A1 | 8/2018 | Guidotti et al. |
| 2018/0249993 A1 | 9/2018 | Denti et al. |
| 2018/0289480 A1 | 10/2018 | D'ambra et al. |
| 2018/0303614 A1 | 10/2018 | Schaffner et al. |
| 2018/0311007 A1 | 11/2018 | Tyler, II et al. |
| 2018/0318079 A1 | 11/2018 | Patel et al. |
| 2018/0318083 A1 | 11/2018 | Bolling et al. |
| 2018/0344311 A1 | 12/2018 | Gilmore et al. |
| 2018/0353297 A1 | 12/2018 | Griffin |
| 2018/0360439 A1 | 12/2018 | Niland et al. |
| 2019/0000624 A1 | 1/2019 | Wilson et al. |
| 2019/0015205 A1 | 1/2019 | Rajagopal et al. |
| 2019/0069891 A1 | 3/2019 | Gilmore et al. |
| 2019/0083085 A1 | 3/2019 | Gilmore et al. |
| 2019/0105027 A1 | 4/2019 | Gilmore et al. |
| 2019/0117401 A1 | 4/2019 | Cortez, Jr. et al. |
| 2019/0151090 A1 | 5/2019 | Gross et al. |
| 2019/0175345 A1 | 6/2019 | Schaffner et al. |
| 2019/0175346 A1 | 6/2019 | Schaffner et al. |
| 2019/0183480 A1 | 6/2019 | Hiorth et al. |
| 2019/0183648 A1 | 6/2019 | Trapp et al. |
| 2019/0216599 A1 | 7/2019 | Alkhatib |
| 2019/0240023 A1 | 8/2019 | Spence et al. |
| 2019/0314155 A1 | 10/2019 | Franklin et al. |
| 2019/0328529 A1 | 10/2019 | Griswold et al. |
| 2019/0328530 A1 | 10/2019 | McDaniel et al. |
| 2019/0343506 A1* | 11/2019 | Karapetian ........ A61B 17/0482 |
| 2019/0365539 A1 | 12/2019 | Rabito et al. |
| 2019/0380699 A1 | 12/2019 | Bak-Boychuk et al. |
| 2020/0155798 A1 | 5/2020 | Yang et al. |
| 2020/0297489 A1 | 9/2020 | Bishop et al. |
| 2020/0330228 A1 | 10/2020 | Anderson et al. |
| 2020/0345496 A1 | 11/2020 | Bishop et al. |
| 2020/0390554 A1 | 12/2020 | Pham et al. |
| 2021/0186699 A1 | 6/2021 | Bishop et al. |
| 2021/0213259 A1 | 7/2021 | Giasolli et al. |
| 2022/0338990 A1 | 10/2022 | Hammill et al. |
| 2022/0339437 A1 | 10/2022 | Sorajja |

FOREIGN PATENT DOCUMENTS

| | | |
|---|---|---|
| CN | 101184454 | 10/2010 |
| CN | 101902975 | 12/2010 |
| CN | 103491901 | 1/2014 |
| CN | 103635160 | 3/2014 |
| CN | 103813757 | 5/2014 |
| CN | 103889345 | 6/2014 |
| CN | 104000625 | 8/2014 |
| CN | 104582637 | 4/2015 |
| CN | 105555229 | 5/2016 |
| CN | 107569301 | 1/2018 |
| EP | 1 898 802 | 9/2015 |

(56) References Cited

FOREIGN PATENT DOCUMENTS

| | | |
|---|---|---|
| EP | 2 979 647 | 2/2016 |
| EP | 3562410 | 11/2019 |
| JP | 2014-523282 | 9/2014 |
| RU | 2219853 | 12/2003 |
| WO | WO 2007/061834 | 5/2007 |
| WO | WO 2007/100268 | 9/2007 |
| WO | WO 2008/005747 | 1/2008 |
| WO | WO 2010/128502 | 11/2010 |
| WO | WO 2012/040865 | 4/2012 |
| WO | WO 2013/179295 | 12/2013 |
| WO | WO 2014/134185 | 9/2014 |
| WO | WO 2017/066888 | 4/2017 |
| WO | WO 2017/066889 | 4/2017 |
| WO | WO 2017/066890 | 4/2017 |
| WO | WO 2017/117560 | 7/2017 |
| WO | WO 2018/035378 | 2/2018 |
| WO | WO 2018/126188 | 7/2018 |
| WO | WO 2018/148324 | 8/2018 |
| WO | WO 2018/148364 | 8/2018 |
| WO | WO 2018/160456 | 9/2018 |
| WO | WO 2018/227048 | 12/2018 |
| WO | WO 2019/013994 | 1/2019 |
| WO | WO 2019/074815 | 4/2019 |
| WO | WO 2019/177909 | 9/2019 |
| WO | WO 2019/195860 | 10/2019 |
| WO | WO 2019/231744 | 12/2019 |
| WO | WO 2019/236654 | 12/2019 |
| WO | WO 2020/106705 | 5/2020 |
| WO | WO 2020/109594 | 6/2020 |
| WO | WO 2020/109596 | 6/2020 |
| WO | WO 2020/109599 | 6/2020 |
| WO | WO 2020/123719 | 6/2020 |
| WO | WO 2020/219281 | 10/2020 |
| WO | WO 2020/256853 | 12/2020 |
| WO | WO 2021/257278 | 12/2021 |
| WO | WO 2022/232070 | 11/2022 |

OTHER PUBLICATIONS

Carpentier, M.D., Alain, "Cardiac Valve Surgery—the 'French Correction'", The Journal of Thoracic and Cardiovascular Surgery, Sep. 1983, vol. 86, No. 3, pp. 323-337.

Júnior, Francisco Gregori et al., "Surgical Repair of Chordae Tendineae Rupture After Degenerative Valvular Regurgitation Using Standardized Bovine Pericardium", Revista Brasileira de Cirurgia Cardiovascular, Jan. 2013, vol. 28, No. 1, pp. 36-46.

Kobayashi et al., "Ten Year Experience of Chordal Replacement with Expanded Polytetrafluoroethylene in Mitral Valve Repair", Circulation, American Heart Association, Nov. 7, 2000, pp. III-30-34.

Shikata et al., "Repair of Congenitally Absent Chordae in a Tricuspid Valve Leaflet with Hypoplastic Papillary Muscle Using Artificial Chordae", J Card Surg, 25:737-739 (2010).

International Search Report and Written Opinion received in PCT Application No. PCT/US2021/035423, dated Oct. 6, 2021 in 20 pages.

\* cited by examiner

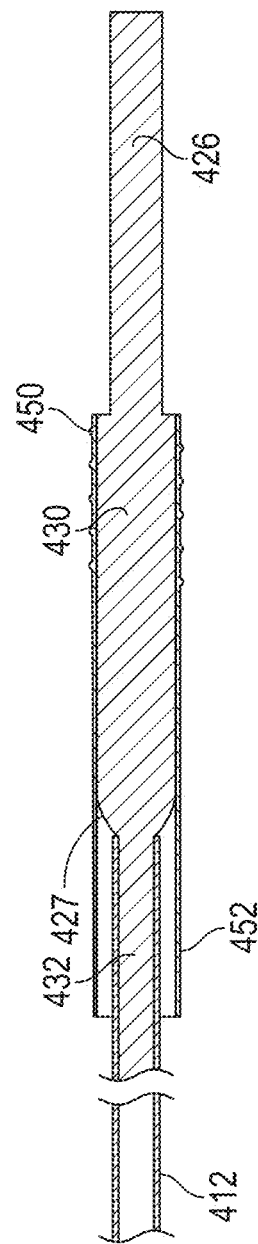

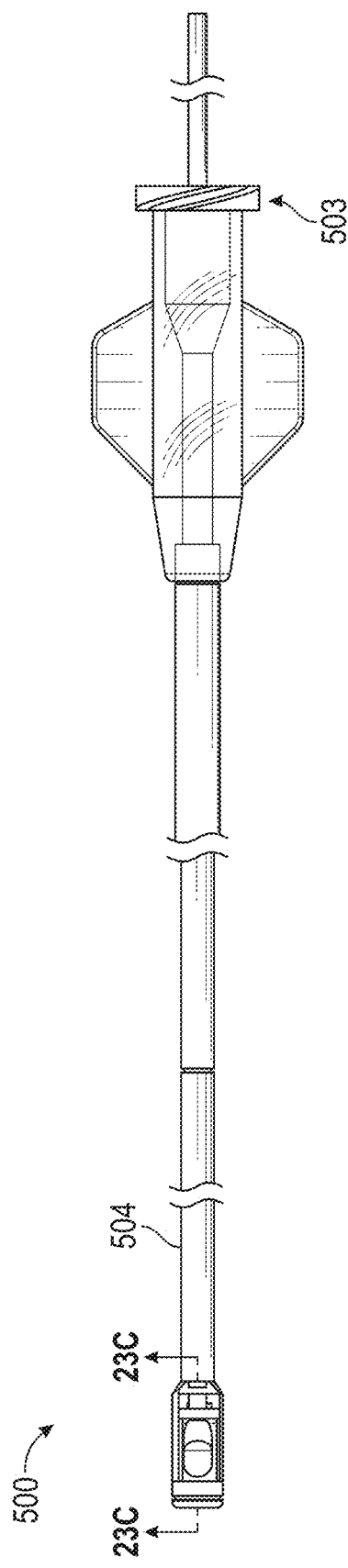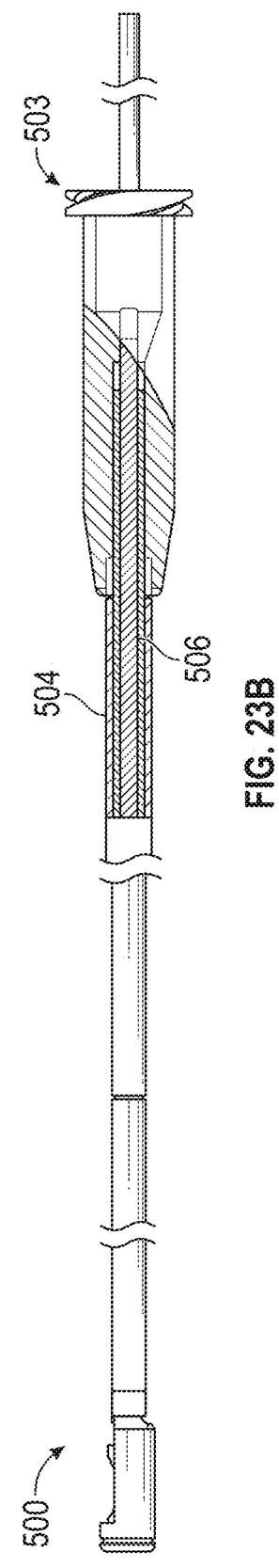
FIG. 23A
FIG. 23B

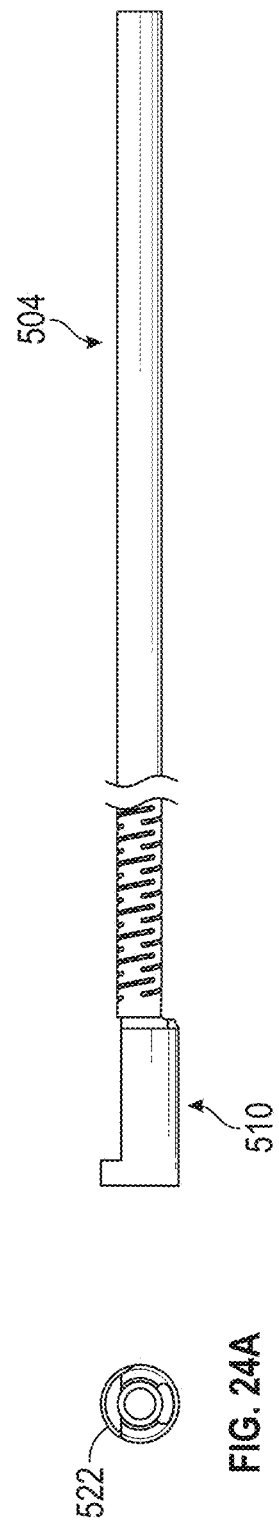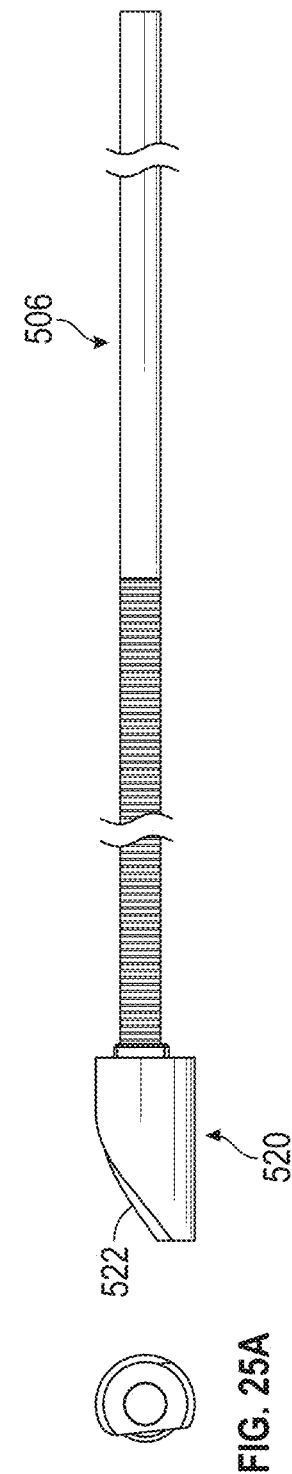

METHOD AND APPARATUS FOR MITRAL VALVE CHORD REPAIR

INCORPORATION BY REFERENCE TO ANY PRIORITY APPLICATIONS

This application is the U.S. National Phase under 35. U.S.C. § 371 of International Application PCT/US2021/035423, filed Jun. 2, 2021, which claims priority to U.S. Provisional Application No. 63/040,389, filed Jun. 17, 2020, the entirety of these applications are hereby incorporated by reference herein for all purposes.

Any and all applications for which a foreign or domestic priority claim is identified in the PCT Request as filed with the present application are hereby incorporated by reference.

BACKGROUND

The present disclosure relates to mitral valve repair or replacement and more generally to methods and methods and devices for mitral valve reshaping, repair and/or replacement of mitral chords to restore proper functioning of the mitral valve from a state of mitral valve regurgitation.

The heart includes four heart valves, which allow blood to pass through the four chambers of the heart in one direction. The four valves are the tricuspid, mitral, pulmonary and aortic valves. The four chambers are the right and left atria (upper chambers) and right and left ventricle (lower chambers).

The mitral valve is formed by two leaflets, which are known as the anterior leaflet and the posterior leaflet, which open and close in response to pressure placed on the leaflets by the pumping of the heart. There are several problems that can develop or occur with respect to the mitral valve. Such problems include mitral valve regurgitation (MR), in which the mitral valve leaflets do not close properly, which can cause leakage of the mitral valve. Severe mitral regurgitation can adversely affect cardiac function and compromise a patient's quality of life and life-span.

Several techniques have been developed for correcting mitral valve regurgitation. These include heart transplant, valve replacement or repair, chordae tendinea shortening or replacement and mitral annular repair also known as annuloplasty, depending upon the stage and underlying etiology.

As it relates to chordae tendinea replacement or repair, certain surgical and trans apical approaches have been proposed. Despite those efforts, however, there remains a need for a transvascular approach for chordae tendinea replacement or repair, for, such as but not limited to, reduce or eliminate MR.

SUMMARY

Methods and devices for transvascular prosthetic chordae tendinea implantation are disclosed. A catheter is advanced into the left atrium. From an atrium side, the catheter can be anchored to a superior surface of a mitral valve leaflet and a leaflet anchor can be advanced into the mitral valve leaflet to secure the mitral valve leaflet to a leaflet suture. A ventricular anchor is anchored to the wall of the ventricle to secure the ventricular wall to a ventricle suture. The leaflet suture and the ventricle suture may be tensioned and connected by a suture lock to form an artificial chordae.

According to one example ("Example 1"), a tissue anchor includes a hub, a suture extending proximally from the hub, a helical anchor extending distally from the hub; and a secondary anchor axially moveable in a distal direction from a first configuration to a second, deployed configuration to engage tissue and inhibit unscrewing of the helical anchor.

According to another example ("Example 2") further to Example 1, the secondary anchor comprises a tine that extends between a proximal end and a sharpened distal end.

According to another example ("Example 3") further to Example 2, the tine is carried by a support.

According to another example ("Example 4") further to Example 3, the support includes an annular structure.

According to another example ("Example 5") further to any one of Examples 3 or 4, the support can receive a tubular structure of a deployment system for advancing the support distally with respect to the helical anchor.

According to another example ("Example 6") further to Example 2, the hub includes a tine guide for axially moveably receiving the tine.

According to another example ("Example 7") further to Example 6, the tine guide includes a deflection surface for deflecting the tine into a launch angle that inclines radially outwardly in the distal direction.

According to another example ("Example 8") further to Example 7, the launch angle is within a range of 30 to 45 degrees.

According to another example ("Example 9") further to Example 1, the hub includes an aperture for axially moveably receiving the secondary anchor.

According to another example ("Example 10") further to any one of Examples 1-9, the tissue anchor further includes a core wire attached to the hub and extending concentrically through the helical anchor.

According to another example ("Example 11") further to any one of Examples 1-10, the tissue anchor further includes a suture anchor guide extending proximally from the hub.

According to another example ("Example 12") further to Example 11, in a second, deployed configuration, the secondary anchor extends through the suture anchor guide.

According to another example ("Example 13") further to Example 12, the secondary anchor extends through an aperture in the suture anchor guide.

According to another example ("Example 14") further to Example 13, as the secondary anchor moves to the second, deployed configuration, the secondary anchor is operable to pierce the suture anchor guide.

According to another example ("Example 15") further to Example 1, the tissue anchor further includes a radiopaque marker carried by the secondary anchor.

According to another example ("Example 16") further to any one of Examples 1-15, the tissue anchor further includes a core wire attached to the hub and extending concentrically through the helical anchor.

According to another example ("Example 17") further to Example 16, the tissue anchor further includes a radiopaque marker axially movably carried by the core wire.

According to another example ("Example 18") further to Example 16, the tissue anchor further includes a spring carried by the core wire.

According to another example ("Example 19") further to Example 16, the core wire extends distally beyond the helical anchor.

According to another example ("Example 20") further to Example 16, the tissue anchor further includes a distal stop on the core wire operable to limit distal travel of the radiopaque marker.

According to another example ("Example 21") further to Example 1, the tissue anchor further includes a tissue piercing point on a distal end of the helical anchor, and a barb on the helical anchor, proximal to the point and configured to resist rotation of the helical anchor out of engagement with tissue.

According to another example ("Example 22") further to any one of Examples 1-21, the secondary anchor is operable to increase an anchor torque resistance of the tissue anchor by a factor between 2 to 5 as compared to an anchor torque resistance of the tissue anchor without the secondary anchor.

According to another example ("Example 23") further to any one of Examples 1-21, an anchor torque resistance of the helical anchor with the secondary anchor is between 2 N/cm to 5 N/cm.

According to another example ("Example 24") further to any one of Examples 1-21, the secondary anchor increases an anchor torque resistance of the helical anchor by at least a factor of 2 as compared to an anchor torque resistance of the tissue anchor without the secondary anchor.

According to another example ("Example 25") further to any one of Examples 1-21, an anchor torque resistance of the helical anchor is greater than 2 N/cm.

According to one example ("Example 26"), a method of transvascular prosthetic chordae tendinae implantation includes advancing a catheter into a left atrium, through a mitral valve, and into a left ventricle; deploying a ventricular anchor from the catheter and into a wall of the left ventricle by rotating a helical tissue anchor into the wall of the left ventricle; deploying a secondary tissue anchor into the wall of the left ventricle to inhibit unscrewing of the helical tissue anchor; leaving a ventricular suture attached to the ventricular anchor and extending proximally through the catheter; from an atrium side, securing a leaflet anchor catheter to a mitral valve leaflet; with the leaflet anchor catheter secured to the leaflet, advancing a leaflet anchor from the catheter through the mitral valve leaflet to secure the mitral valve leaflet to a leaflet suture, with the leaflet suture extending proximally through the catheter; and securing the leaflet suture to the ventricular suture to limit a range of travel of the leaflet in a direction of the left atrium.

According to another example ("Example 27") further to Example 26, in which deploying the secondary tissue anchor comprises axially advancing the secondary tissue anchor in a distal direction with respect to the helical tissue anchor.

According to another example ("Example 28") further to Example 26, in which deploying the secondary tissue anchor increases an anchor torque resistance of the ventricular anchor by a factor of between 2 to 5 as compared to an anchor torque resistance of the ventricular anchor without the secondary anchor.

According to another example ("Example 29") further to Example 26, an anchor torque resistance of the tissue anchor and secondary tissue anchor is between 2 N/cm to 5 N/cm.

According to another example ("Example 30") further to Example 26, the secondary tissue anchor increases an anchor torque resistance of the ventricular anchor by at least a factor of 2 as compared to an anchor torque resistance of the ventricular anchor without the secondary anchor.

According to another example ("Example 31") further to Example 26, an anchor torque resistance of the secondary tissue anchor and the ventricular anchor is at least greater than 2 N/cm.

According to one example ("Example 32"), an access system for directing a ventricular anchor sheath at a target site in a left ventricle includes a delivery catheter having an elongate, flexible tubular body with a proximal end, a distal end, a central axis and a steering zone near the distal end, the steering zone actively deflectable to provide a delivery catheter curve residing in a delivery catheter curve plane; and an anchor sheath axially advanceable through the delivery catheter, the anchor sheath having a proximal preset curve residing in a proximal preset curve plane and a distal preset curve, wherein the anchor sheath is configured to rotate within the delivery catheter to bias the proximal preset curve plane into alignment with the delivery catheter curve plane in response to axial alignment of the proximal preset curve within the delivery catheter curve.

According to another example ("Example 33") further to Example 32, the distal preset curve resides in a distal preset curve plane which is angled from the proximal preset curve plane.

According to another example ("Example 34") further to any one of Examples 32-33, in which the delivery catheter curve is actively adjustable throughout a range of at least 10 to 150 degrees.

According to one example ("Example 35"), an access system for directing a ventricular anchor sheath at a target site in a left ventricle includes a delivery catheter having an elongate, flexible tubular body with a proximal end, a distal end and a steering zone near the distal end, the steering zone actively deflectable to provide a delivery catheter curve residing in a delivery catheter curve plane; and an anchor sheath axially advanceable through the delivery catheter, the anchor sheath having a proximal preset curve residing in a proximal preset curve plane and a distal preset curve, wherein the proximal preset curve and the delivery catheter curve are configured to cooperate to provide tactile indicium of a rotational alignment of the anchor sheath within the delivery catheter.

According to one example ("Example 36"), a ventricular anchor delivery sheath includes an elongate, flexible tubular body having a proximal end, a distal end, and a longitudinal axis; a proximal preset curve in the tubular body; and a distal preset curve in the tubular body According to another example ("Example 37") further to Example 36, the proximal preset curve resides in a first plane and the distal preset curve resides in a second plane, and the second plane is rotationally angled from the first plane.

According to another example ("Example 38") further to Example 37, the second plane is rotationally angled from the first plane by an angle within a range from 40 to 75 degrees.

According to another example ("Example 39") further to any one of Examples 37-38, the distal preset curve has an angle within a range of from 5 to 60 degrees in the first plane.

According to another example ("Example 40") further to any one of Examples 36-39, a length of the distal preset curve is no more than 50% of a length of the proximal preset curve.

According to another example ("Example 41") further to any one of Examples 36-39, a length of the distal preset curve is no more than 20% of a length of the proximal preset curve.

According to another example ("Example 42") further to any one of Examples 36-41, a distance between a longitudinal center of the proximal preset curve and a longitudinal center of the distal preset curve is with a range between 45 and 85 millimeters.

According to another example ("Example 43") further to any one of Examples 36-41, a longitudinal center of distal preset curve is within a range of from 50 to 70 millimeters from the distal end of the ventricular anchor delivery sheath.

According to another example ("Example 44") further to any one of Examples 36-41, a longitudinal center of proximal preset curve is within a range of from 100 to 145 millimeters from the distal end of the ventricular anchor delivery sheath.

According to another example ("Example 45") further to any one of Examples 36-44, a distal anchor compartment having a collapsible side wall.

According to another example ("Example 46"), a ventricular anchor delivery sheath includes an elongate, flexible tubular body having a proximal end, a distal end, and a longitudinal axis; and a distal preset curve in the tubular body.

According to another example ("Example 47") further to Example 46, a longitudinal center of distal preset curve is within a range of from 50 to 70 millimeters from the distal end of the ventricular anchor delivery sheath.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting on scope.

FIG. 22F is longitudinal cross-sectional view taken through a mandrel that can be used to form the distal portion of the ventricular anchor delivery subsystem shown in FIG. 22A, in accordance with an embodiment.

FIG. 23A is a top view of an embodiment of a cutter catheter according to aspects of the disclosure, in accordance with an embodiment.

FIG. 23B is a side and partial cross-sectional view of the cutter catheter of FIG. 23A, in accordance with an embodiment.

FIG. 24A is a front view of a cutter housing of the cutter catheter of FIG. 23A according to aspects of the disclosure, in accordance with an embodiment.

FIG. 24B is a side view of the cutter housing of FIG. 23A, in accordance with an embodiment.

FIG. 25A is front view of an embodiment of a cutter head, in accordance with an embodiment.

FIG. 25B is a side view of the cutter head of FIG. 25A, in accordance with an embodiment.

DETAILED DESCRIPTION

U.S. patent application Ser. No. 15/858,671, filed Dec. 29, 2017 (the entirety of which is hereby incorporated by reference herein discloses systems and methods for the transvascular prosthetic chordae tendinae implantation. One aspect involves advancing a catheter into the left atrium, through the mitral valve, and into the left ventricle; deploying a ventricular anchor from the catheter and into a wall of the left ventricle, leaving a ventricular suture attached to the ventricular anchor and extending proximally through the catheter; and advancing a leaflet anchor into a mitral valve leaflet to secure the mitral valve leaflet to a leaflet suture, with the leaflet suture extending proximally through the catheter, and extending the leaflet suture over the top of the coaptive edge and securing the leaflet suture to the ventricular suture to limit a range of travel of the leaflet in the direction of the left atrium. Certain aspects are developed further herein.

The approach to the mitral valve can be accomplished through a standard transseptal approach to provide access to the left atrium. With this access, a first step can include securing a leaflet capture catheter to the leaflet of the mitral valve in the location determined to best correct regurgitation. Probing the surface of the leaflet from the superior atrium surface can advantageously provide immediate feedback as to the optimal location to add an additional mitral valve chord. In another implementation of the disclosure, the ventricular anchor is deployed first, followed by deployment of the leaflet anchor.

Figure 1:
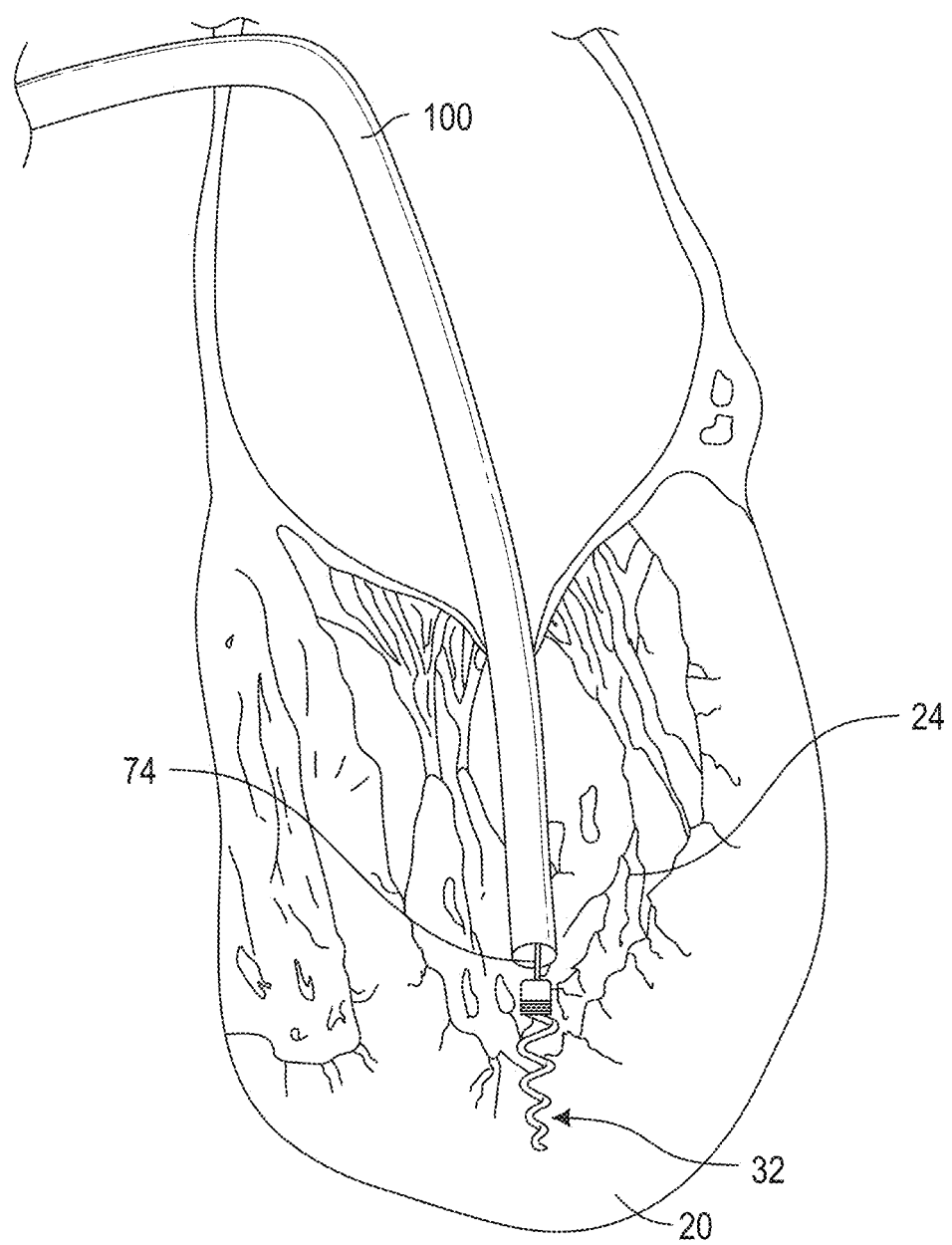
FIG. 1 illustrates placement of a ventricular anchor via transceptal approach to the mitral valve, in accordance with an embodiment.

Referring to FIG. 1, a ventricular anchor such as a helical anchor 32 has been deployed near the apex 20 of the left ventricle 24. While the helical anchor 32 is shown positioned near the apex 20 in the following Figures, the anchor 32 can be attached at a point that is offset from the thin tissue of the apex, and can be instead implanted in the generally thicker adjacent wall of the ventricle, such as between the two papillary muscles. This allows the implanted neo chord construct (suture, optional neo papillary muscle, and/or the helical anchor) to be aligned along a longitudinal axis substantially parallel to or concentric with the original path of the native chord. In certain embodiments, the implanted neo chord construct is aligned along a longitudinal axis that is within 5 degrees, 10 degrees, or 15 degrees of being parallel with the original path of the native chord and/or the path of the adjacent native chord. In addition, while a helical anchor is illustrated the anchor can have a different structure for engaging tissue of the heart and thus other tissue anchor structures can be used instead of a helical structure including various piercing, hook or radially expandable structures known for engaging tissue.

Figure 2A:
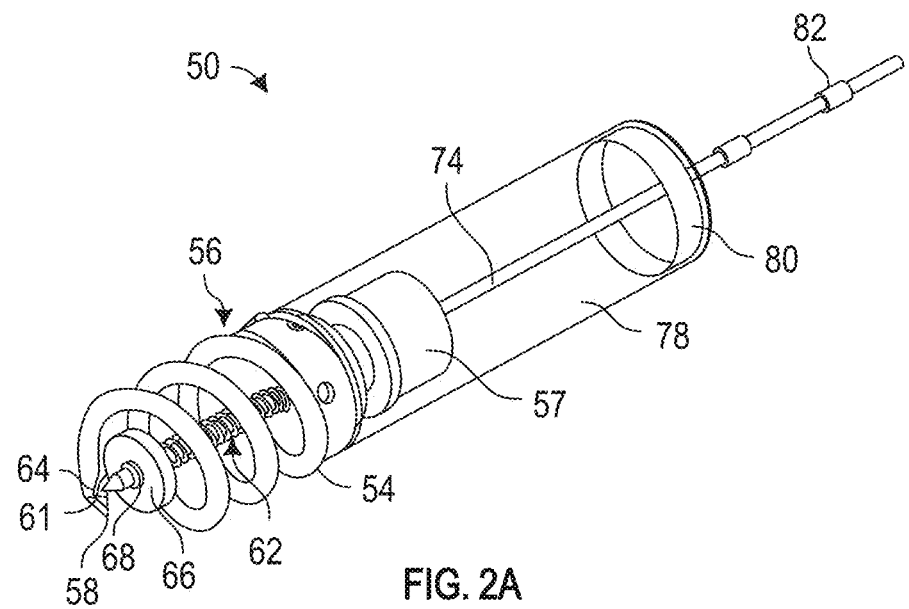
FIGS. 2A and 2B illustrate a ventricular anchor, in accordance with an embodiment.
Figure 2B:
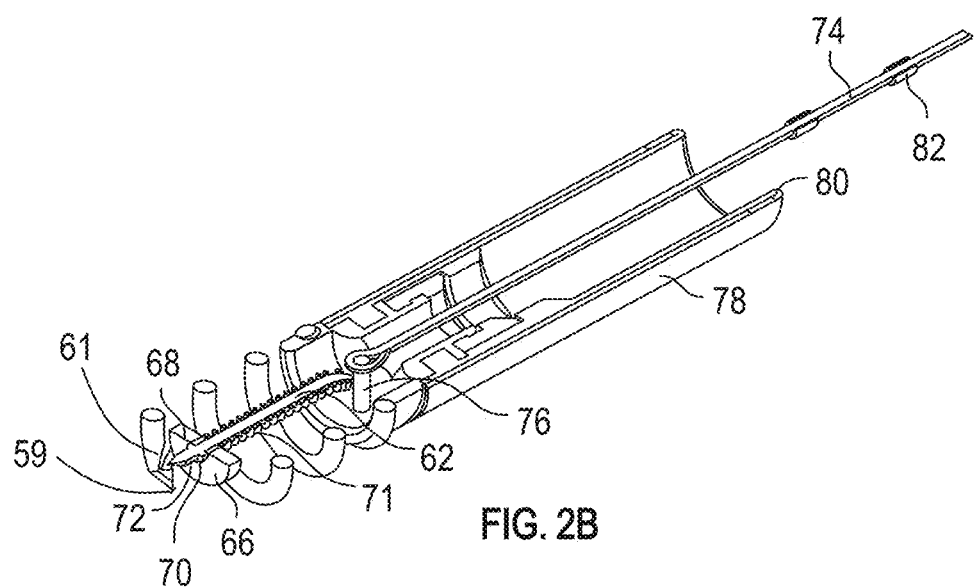

Referring to FIGS. 2A and 2B, there is illustrated one implementation of a tissue anchor suitable for use as a ventricular anchor in accordance with an aspect of the present disclosure. The anchor assembly 50 will be described primarily in the context of the present chordae repair application, however the anchor may be utilized in any of a wide variety of other applications where a soft tissue or bone anchor may be desired.

The anchor assembly 50 generally comprises a coil 54 which may comprise any of a variety of materials such as stainless steel or Nitinol. The coil 54 extends helically between a proximal end 56 and a distal end 58. Distal end 58 is provided with a sharpened tip or tissue piercing point 59, and also carries a retention barb 61, configured to resist reverse rotation of the coil and detachment from tissue. The proximal end 56 of the coil 54 is carried by (attached to or formed integrally with) a hub 57 discussed in additional detail below.

Extending distally from the hub 57 and within the coil 54 is an elongate core wire 62 having a sharp, tissue piercing distal end 64. The distal end 64 is positioned distally of the distal end 58 of the coil 54. This enables the sharp distal end 64 to pierce tissue upon contact, and prior to beginning rotation of the coil 54 to embed the coil 54 within the target tissue. Engaging the tip 64 prior to rotation of the anchor stabilizes the anchor against sideways movement allowing a single placement of the anchor 50 against tissue, and rotation of the coil 54 to engage tissue, without 'walking' of the anchor away from the desired target site as will be understood by those of skill in the art. A proximal end of the core wire 62 may be attached to the hub in any of a variety of ways, such as by soldering, brazing, adhesives and/or mechanical interference such as by entering an aperture in a sidewall or other surface of the hub 57.

A radiopaque depth marker 66 is provided with an aperture 68 and is axially movably carried on the core wire 62. A distal stop 70 such as a radially outwardly extending protrusion or annular ridge is carried by the core wire 62, and spaced proximally of the sharpened distal end 64 to provide a core wire leading segment 72 on the distal side of the stop 70 so that the marker 66 cannot interfere with the tissue anchoring function of the distal tip 64. The stop 70 functions to limit distal travel of the marker 66. The marker 66 may be an annular structure such as a circular disc with a central aperture to receive the core wire 62.

A coil spring 71 is concentrically carried over the core wire 62 and biases the radiopaque marker 66 in the distal direction. The radiopaque marker 66 is thus held in position against a proximal surface of the stop 70. In use, the marker 66 rides on the surface of tissue at the target attachment site. As the helical coil anchor 54 is rotated and advances distally into tissue, the marker 66 rides proximally on the core wire 62 along with the tissue surface, compressing the coil spring 71 until the marker 66 is retracted proximally to the hub when the tissue anchor is fully embedded. This enables fluoroscopic visualization of the progress of the coil into tissue and of the fully engaged end point of embedding the coil 54 into the target tissue, by observing the changing distance between marker 66 and a reference such as the hub 57 or other radiopaque marker.

The hub 57 comprises a proximal connector for engagement with a rotational driver as discussed elsewhere herein. In one implementation, the connector comprises an aperture such as a hexagonal aperture for removably engaging a complementary surface structure on the distal end of the driver. A suture 74 is secured to the anchor assembly 50, for example secured to the hub 57, coil 54 or core wire 62. In the illustrated embodiment, the suture 74 is attached to a cross pin 76 which may be inserted through one or two apertures in the sidewall of the hub and across a central hub lumen. The suture may additionally carry one or two or more radiopaque markers 82 spaced apart from the hub 57, and may extend proximally through the proximal connector and a central lumen in the rotational driver.

A suture lock guide such as a tubular sleeve 78 extends proximally from the hub 57 for at least about 2 mm or 4 mm or 8 mm but generally no more than about 5 cm or 2 cm depending upon desired performance. In certain example embodiments, a suture lock guide such as a tubular sleeve 78 extends proximally from the hub 57 for at least 2 mm or 4 mm or 8 mm but generally no more than 5 cm or 2 cm depending upon desired performance. The guide sleeve 78 may comprise a flexible material such as ePTFE. A radiopaque marker band 80 may be carried by the proximal end of sleeve 78 and spaced axially apart from the marker 82 on suture 74, to facilitate fluoroscopic visualization of the suture lock as it is advanced distally over the suture 74. The marker band 80 may be positioned in between an inner layer and an outer layer of ePTFE sleeve, such as may result from placing the band over the sleeve and inverting the sleeve over itself to entrap the ring.

The suture lock guide may comprise any of a variety of structures such as a sleeve as illustrated or an alignment pin extending proximally from the hub and received within a lumen in the suture lock, for maintaining the orientation of the suture lock following detachment from the deployment catheter. Since the tension on the suture is optimized while the suture lock is held in place by the deployment catheter, any change in the orientation of the suture lock following release from the catheter would affect tension on the leaflet and potentially negatively affect the therapeutic value of the implant. The suture lock guide helps maintain constant the maximum distance between the ventricular anchor and the leaflet anchor both pre and post deployment from the catheter. In this manner the maximum tension on the leaflet suture (during systole) remains unchanged after the suture lock has been locked, both before and after detachment of the catheter.

Figure 2C:
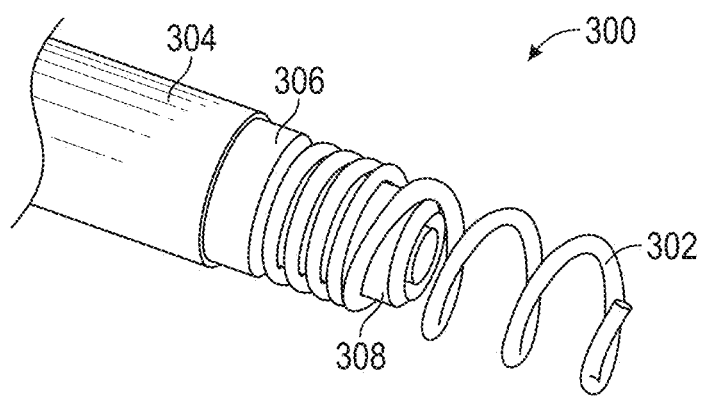
FIG. 2C is a perspective view of a ventricular anchor on the distal end of a ventricular anchor deployment tool, in accordance with an embodiment.
Figure 2D:
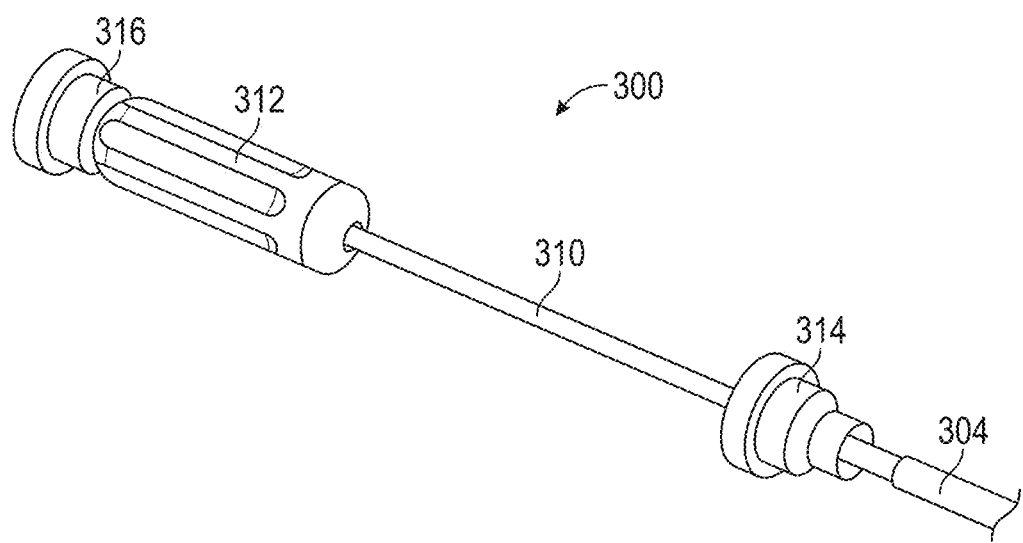
FIG. 2D is a perspective view of the proximal end of a ventricular anchor deployment tool, in accordance with an embodiment.
Figure 2E:
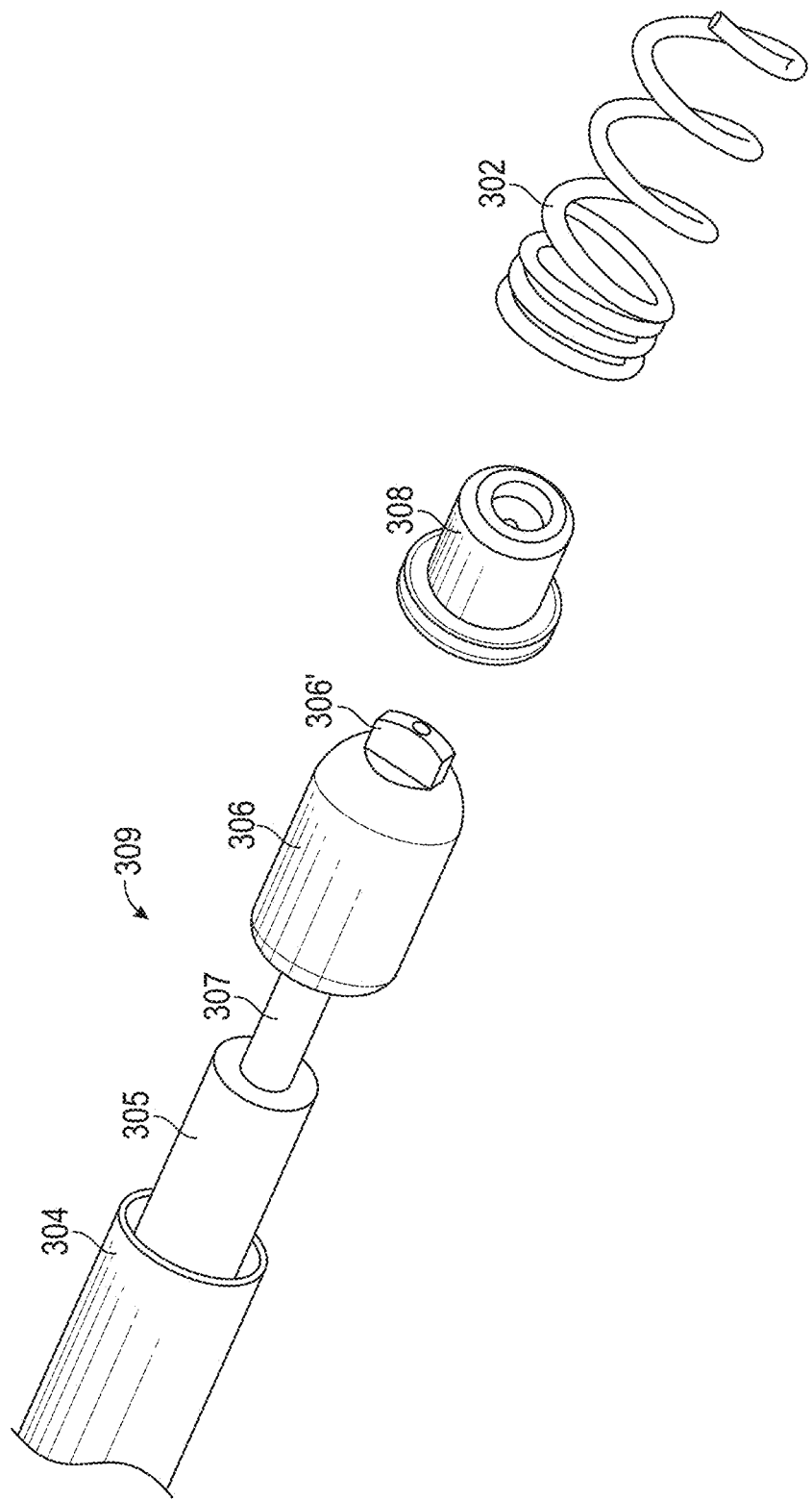
FIG. 2E is a partially exploded perspective view of a ventricular anchor and the distal end of a ventricular anchor deployment tool, in accordance with an embodiment.

The helical anchor assembly 50 may be delivered by a ventricular anchor delivery subsystem 300. FIGS. 2C-2E illustrate various views of a ventricular anchor delivery subsystem 300 and its components. FIG. 2C depicts a perspective view of a distal end of the subsystem 300. FIG. 2D depicts a perspective view of a proximal end of the subsystem 300. FIG. 2E depicts a partially exploded view of a distal end of the subsystem 300.

The subsystem 300 may be delivered through the delivery catheter 100. The delivery catheter 100 may access the left atrium through conventional techniques, such as through an atrial trans-septal puncture. The delivery catheter 100 may be maintained in a substantially constant location throughout the procedure as various subsystems are placed and removed from the delivery catheter 100. For instance, the distal end of the delivery catheter 100 may be positioned in the left atrium. In other implementations, the distal end of the delivery catheter 100 may be positioned in the left ventricle throughout the duration of the procedure.

As shown in FIGS. 2C-2E, the ventricular anchor delivery subsystem 300 may comprise an outer sheath 304, a driver (comprising shaft 307 and head 306), an anchor hub 308, and an anchor 302. The anchor may be a helical anchor 302 and the drive head 306 can be configured to rotate the helical anchor 302. The helical anchor 302 may comprise an inner diameter configured to be received over the outer diameter of an anchor hub 308. The helical anchor 302 may be securely fixed secured to the anchor hub 308 by an interference fit or other frictional engagement, soldering or other known attachment technique. The anchor hub 308 may be left implanted along with the helical anchor 302.

The anchor hub 308 may comprise a lumen positioned substantially along a central axis of the anchor hub 308 for receiving a suture 74 (FIG. 2A) and attaching the suture 74 to the helical anchor 302. In some embodiments, the suture 74 may comprise an attachment element (e.g. a knot or a washer) with a diameter sized to prevent the suture 74 from being pulled proximally through the anchor hub 308 lumen. For example, the suture 74 may be knotted on a distal side of the lumen. In some embodiments, the suture 74 may be tied to the anchor hub 308 (e.g., passed through the lumen, wrapped around a structure such as the outer surface or a cross pin 76 as shown in FIG. 2B, and tied to itself).

The helical anchor 302 may comprise a distal section of windings and a proximal section of windings. The proximal section of windings may be spaced closer together than the distal section of windings and may be configured for securing the helical anchor 302 to the anchor hub 308. The distal section of windings may be spaced further apart than the proximal section of windings and may be configured for insertion into the ventricular tissue. The anchor hub 308 may comprise an enlarged cross-section at its proximal end configured to abut the helical anchor 302 and/or prevent the helical anchor 302 from advancing proximally over the proximal end of the anchor hub 308. Other helical anchors, such as those described elsewhere herein, may be configured to be used with the ventricular anchor delivery subsystem 300 described herein as well.

The proximal face of the helical anchor 308 may comprise a recess for receiving an extending portion 306' of the driver head 306. The recess may be non-circular (e.g., oblong or polygonal such as hexagonal) such that it is configured to transfer torque from the driver to the anchor hub 308 upon rotation of the driver. The recess may be positioned around the central lumen of the anchor hub 308.

In other embodiments, the anchor hub 308 may comprise an extending portion and the driver 306 may have a complementary recess. The driver head 306 may be generally cylindrical, with a distally facing post or aperture with a complementary configuration to rotationally engage the corresponding component on the anchor. The driver head 306 may be fixedly coupled to a drive shaft 307. The driver may comprise a central lumen through the driver head 306 and drive shaft 307 configured to receive the suture 74. The central lumen of the driver may be configured to be aligned with the central lumen of the anchor hub 308. The drive shaft 307 may be received within a guide shaft 305. The diameter of the driver head 306 may be larger than the inner diameter of the guide shaft 305. The outer sheath 304 may be sized to receive the guide shaft 305 as well as the driver head 306, the anchor hub 308, and the helical anchor 302.

The outer sheath 304 may be delivered into the left ventricle and proximal to the ventricular attachment site via the delivery catheter 100. In some embodiments, the outer sheath 304 may be delivered without a delivery catheter. In some implementations, the helical anchor 302 may be concealed within the outer sheath 304 until the outer sheath 304 is positioned proximal to the ventricular attachment site then pushed distally through the outer sheath 304 or the outer sheath 304 is proximally retracted so that the helical anchor 302 is exposed. The helical anchor 302 may be placed into contact with the ventricular tissue. Rotation of the drive shaft 307 may cause the driver head 306, the anchor hub 308, and the helical anchor 302 to rotate thereby screwing the ventricular anchor 302 into the ventricular tissue. Rotation of the driver 309 may axially advance the driver 309, anchor hub 308, and helical screw 302 in a distal direction with respect to the outer sheath 304.

The drive shaft 307 may be rotated manually by a user using a drive handle 312, as shown in FIG. 2D. The proximal end of the ventricular anchor delivery subsystem 300, as illustrated in FIG. 2D, may comprise first and second hemostasis valves 314, 316. The first hemostasis valve 314 may be positioned distal to the drive handle 312 and may provide access to the guide shaft 305. The second hemostasis valve 316 may be positioned proximal to the drive handle 312 and may provide access to the central lumen of the driver. The ventricular anchor suture (not shown) may extend through the second hemostasis valve 316.

In some implementations, the inserting portion 306' of the driver head 306 and the recess of the anchor hub 308 may have a frictional engagement that transiently holds the two components together. The frictional engagement may be overcome upon proximal retraction of the driver by a counter force from the ventricular tissue once the helical anchor 302 is inserted. In some implementations, proximal tension on the suture 74 may provide an engagement force between the proximal hub 308 and the driver head 306, which can be released upon retraction of the driver 309. The driver head 306 may be proximally withdrawn into the outer sheath 304 before the outer sheath 304 is withdrawn into the delivery catheter 100.

The non-implanted components of the ventricular anchor delivery subsystem 300 may be removed from the delivery catheter 100 and subsequent subsystems may be placed in the delivery catheter 100 for completing implantation of the neo chordae. In a modified embodiment, the ventricular anchor delivery subsystem 300 and subsequent subsystems such as the leaflet anchor delivery subsystem 330 may be positioned within the delivery catheter 100 at the same time and in certain arrangements the tissue and leaflet anchors can both be preloaded into the delivery catheter. In alternative embodiments, the implantation of the ventricular anchor may be performed in a different order (e.g., after the implantation of the leaflet anchor). The ventricular anchor delivery components may be proximally retracted over a proximal end of the suture 74, which may remain extending through the delivery catheter 100 to the ventricular anchor 302.

In certain implementations of the present disclosure, it may be desirable to provide a secondary anchor to prevent the helical coil 54 of the ventricular anchor 32 from reverse rotation post implantation which can cause the helical coil 54 to become disengaged from the attachment site. In general, the secondary anchor can be advanceable from a first configuration such as for transluminal navigation and attachment of the primary, helical anchor, to a second, deployed configuration for engaging tissue and inhibiting unscrewing of the helical anchor 54 from the attachment site.

In certain embodiments, the secondary anchor may be deployed into the second configuration automatically in response to full engagement of the primary helical anchor. Alternatively, the secondary anchor may be deployed by manual manipulation of a control or distal advance of a pusher by the attending clinician. The pusher may be in the form of a tubular body axially movably carried over the anchor driver. Alternatively, the pusher may comprise the anchor driver. In such implementations, the anchor driver may be provided with an engagement surface structure such as a ratchet which cooperates with a complementary surface structure on a radially inwardly facing surface of the secondary anchor assembly. The anchor driver may be proximally retracted without affecting the secondary anchor, but subsequent distal advance of the anchor driver deploys the secondary anchor. The pusher may alternatively comprise the suture lock catheter, as discussed further below.

Embodiments of the secondary anchor described above and with respect to FIGS. 2F and 2G can be used independently and/or in combination with features and aspects of the ventricular anchor 32 described herein and with respect to the embodiments described with respect to FIGS. 2A-2E.

Figure 2F:
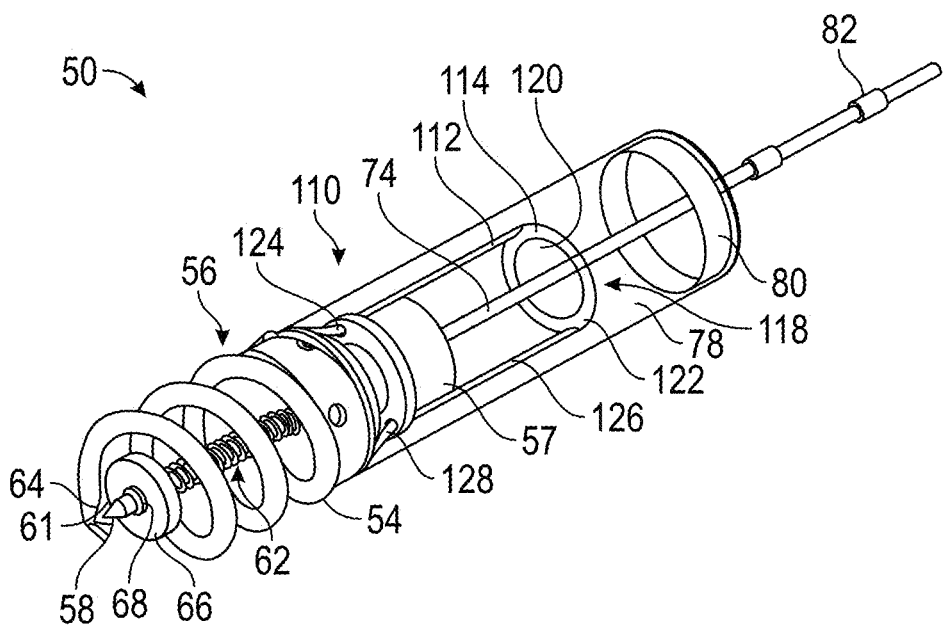
FIG. 2F illustrates a ventricular anchor with a secondary anchor in a first configuration, in accordance with an embodiment.
Figure 2G:
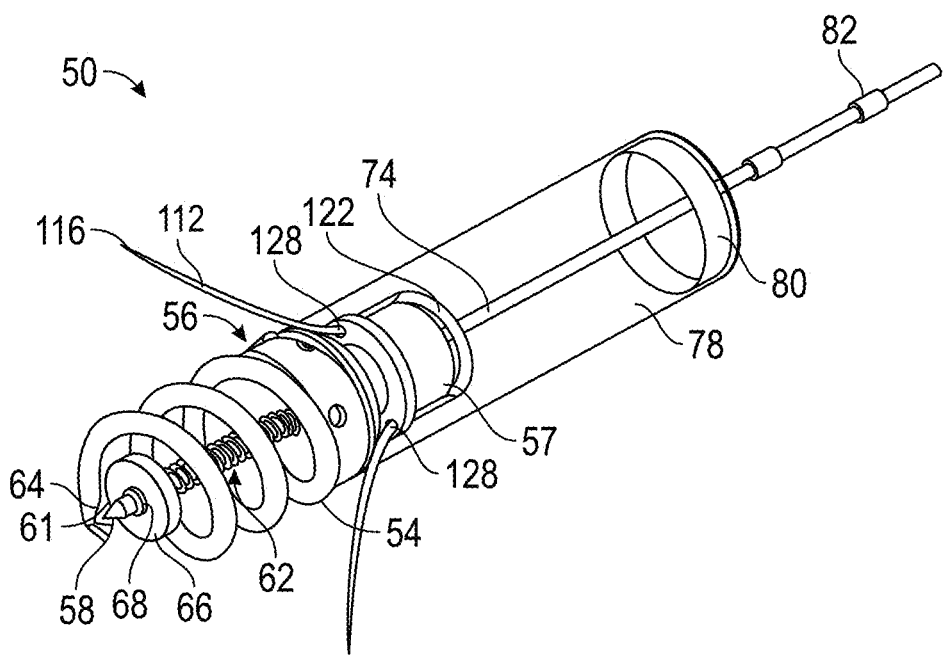
FIG. 2G illustrates the ventricular anchor of FIG. 2F with the secondary anchor in a second, deployed configuration, in accordance with an embodiment.

FIGS. 2F and 2G illustrate an embodiment of the ventricular anchor 32 that can include a secondary anchor 110. In the illustrated embodiment, the secondary anchor 110 comprises at least a first tine 112 extending between a proximal end 114 and a distal sharpened end 116. The tine 112 may be carried by a support 118, such as by connection to proximal end 114. Support 118 can facilitate axial advancement of the tine 112. In the illustrated embodiment, the support 118 comprises an annular structure having an aperture 120, such as a ring 122. The aperture 120 is configured to axially movably receive the anchor driver (not illustrated), or other tubular structure or component that may be a part of the anchor deployment system.

The hub 57 is provided with at least a first tine guide 124, such as an aperture or lumen, for axially movably receiving the first tine 112 therethrough. The first tine guide 124 may include a deflection surface for deflecting the tine 112 into a launch angle that inclines radially outwardly in the distal direction. The launch angle measured at the exit from the tine guide 124 may be within the range of from about 30 degrees to about 45 degrees, and in some implementations within the range of from about 35 degrees to about 40 degrees from the central longitudinal axis of the anchor. In certain example embodiments, the launch angle measured at the exit from the tine guide 124 may be within the range of from 30 degrees to 45 degrees, and in some implementations within the range of from 35 degrees to 40 degrees from the central longitudinal axis of the anchor.

As an alternative or in addition to the deflection surface, the tine may be pre biased radially outwardly, so that it ramps outwardly as it is advanced out of the tine guide 124. Distal advance of the first tine 112 advances the tine through the first tine guide, distal of which the tine 112 extends radially outwardly in a distal direction to expose a length of tine of at least about 1 mm or 2 mm or 3 mm or 4 mm or more, depending upon the desired performance. In certain example embodiments, distal advance of the first tine 112 advances the tine through the first tine guide, distal of which the tine 112 extends radially outwardly in a distal direction to expose a length of tine of at least 1 mm or 2 mm or 3 mm or 4 mm or more, depending upon the desired performance. Measured perpendicular to the longitudinal axis, the distal tip 116 of the fully deployed tine is at least about 1 mm or 2 mm or 3 mm or 4 mm or more from the outer surface of the helical coil 54. In certain example embodiments, measured perpendicular to the longitudinal axis, the distal tip 116 of the fully deployed tine is at least 1 mm or 2 mm or 3 mm or 4 mm or more from the outer surface of the helical coil 54. The distal tip 116 upon full deployment may be spaced laterally from the helical coil by at least about 50% or 75% or 100% or more of the outside diameter of the helical coil. In certain example embodiments, the distal tip 116 upon full deployment may be spaced laterally from the helical coil by at least 50% or 75% or 100% or more of the outside diameter of the helical coil.

The tine 112 may comprise any of a variety of materials such as stainless steel or Nitinol, having sufficient structural integrity to resist rotation and/or be capable of holding a bias. The tine 112 may comprise a flat ribbon or round wire, and in one implementation, comprises 0.016" stainless steel round wire.

Distal advancement of the first tine 112 may be accomplished by applying distal pressure on the support 118, such as by a secondary anchor deployment pusher or catheter advanced over the suture 74 and/or anchor driver discussed elsewhere herein. Alternatively, the secondary anchor 110 may be deployed by advancing the suture lock distally over the sutures and into contact with the support 118, and further to advance the support 118 distally to entrap the support 118 in between the distal end of the suture lock and the hub 57. In this manner, the suture lock can serve as a secondary anchor lock to preventing or inhibit the secondary anchor from backing away from the deployment site.

A second tine 126 may be provided, extending through a second tine guide 128 and connecting to the support ring 122. Three or four or more tines may be provided, depending upon desired performance of the secondary anchoring system. In the illustrated embodiment, two tines are shown, spaced at approximately 180 degrees apart around the circumference of the helical anchor. In a three tine embodiment, the tines may be equidistantly spaced at approximately 120 degree intervals.

As illustrated, the tine guides 124, 128 can direct the tines 112, 126 through the fabric of the tubular suture anchor guide. The fabric may be provided with an aperture aligned with the path of the tine, or the tine may pierce the fabric during deployment. The exit path of the tines can be moved distally if desired, such that the tines extend axially through the hub and into the helical coil, and exit laterally between two spaced apart adjacent windings of the coil. The tines and/or the support 118 may comprise a radiopaque marker or material to enable fluoroscopic confirmation of full deployment.

The use one or more secondary anchors 110 can increase the anchor torque resistance of the helical coil 54 to inhibit or prevent the helical coil 54 of the ventricular anchor 32 from reverse rotation post implantation. Such reverse rotation after implantation can cause the helical coil 54 to become disengaged or loosen from the attachment site. In some embodiments, the secondary anchors 110 can increase the torque resistance of the ventricle anchor 32 by at least a factor of 2, 4, 6, 8 or 10 compared to the use of the ventricular anchor 32 without the secondary anchor 110. In certain embodiments, the addition of one or more of the secondary anchor 110 can increase the torque resistance by a factor of 2 to 10 as compared to the use of a ventricular anchor 32 by itself and in certain embodiments the one or more of the secondary anchor can increase torque resistance by a factor of 2 to 5. In such embodiments, more than one tine of the secondary anchor can be used and in certain embodiments 2, 3, 4, or 5 the secondary anchor can be used, which can be in the form of tines 112, 126 as described above. In some embodiments, the torque resistance with the one or more secondary anchor 110 can be greater than 2 N/cm. In some example, the torque resistance with the addition of one or more tines of the secondary anchor 110 can be at least between 2 N/cm to 5 N/cm.

Additionally, the use of one or more of the secondary anchor 110 can increase the torque stiffness of the helical coil 54 to prevent and or inhibit wobbling or shifting, which can also prevent the helical coil 54 of the ventricular anchor from becoming disengaged from the attachment site. For example, the secondary anchor 110 can increase the torque stiffness by at least a factor of 2, 4, 6, 8 or 10 compared to the use of the ventricular anchor without the secondary anchor 110 and in certain embodiments the secondary anchor can increase the torque stiffness by a factor of between 2 to 10 as compared to the ventricular anchor without the secondary anchor 110 and in certain embodiment by a factor of 3 to 8. In such embodiments, more than one secondary anchor can be used and in certain embodiments 2, 3, 4, or 5 secondary anchors 110 are used and in certain embodiments the secondary anchors can be in the form of tines 112, 126 as described above. In certain embodiment, the torque resistance with the one or more the secondary anchor 110 can be greater than 0.02 N-cm/deg. In some example, the torque resistance with the one or more secondary anchors 110 can be between 0.01 N-cm/deg to 0.03 N-cm/deg.

In some examples, the one or more tines of the secondary anchors 110 can each be at least 5 mm in length as measured from the hub 57. In some examples, the one or more tines of the secondary anchors 110 can each be between 1 mm to 8 mm in length, in certain embodiments between 4 and 7 mm in length and in certain embodiments 5 mm in length. The width between any two tines of the secondary anchor 110 can be approximately 12 mm. In some examples, the width between any two tines can be between 5 mm to 15 mm. The length and width of the tines advantageously allows the tines of the secondary anchor 110 to extend into the pericardial space without perforating through the ventricle wall, while still providing adequate torque resistance and stiffness.

The thickness of each tine can be approximately 0.3 mm. In some examples, the thickness of each tine can be between 0.1 mm to 0.5 mm. This thickness of the tines can provide adequate bend or yield as the tines are advanced.

Further, the angle of each tine from the centerline of the helical coil 54 can be approximately 40 degrees. In some examples, the angle of each tine from the centerline of the helical coil 54 can be between 25 degrees to 60 degrees. This angle can advantageously be extend to provide the desired torque resistance and stiffness while not perforating the ventricle wall. This can also provide the desired orientation of each tine pointing towards the mitral valve when the anchor is positioned at an angle in the ventricle wall.

The end of each tine can be optionally coined along its length. This can prevent the secondary anchor from pulling back too far into the hub 57 by catching the coined portion distal to the respective tine guide 124 or holes in the hub 57 that the tines pass through.

Figure 3:
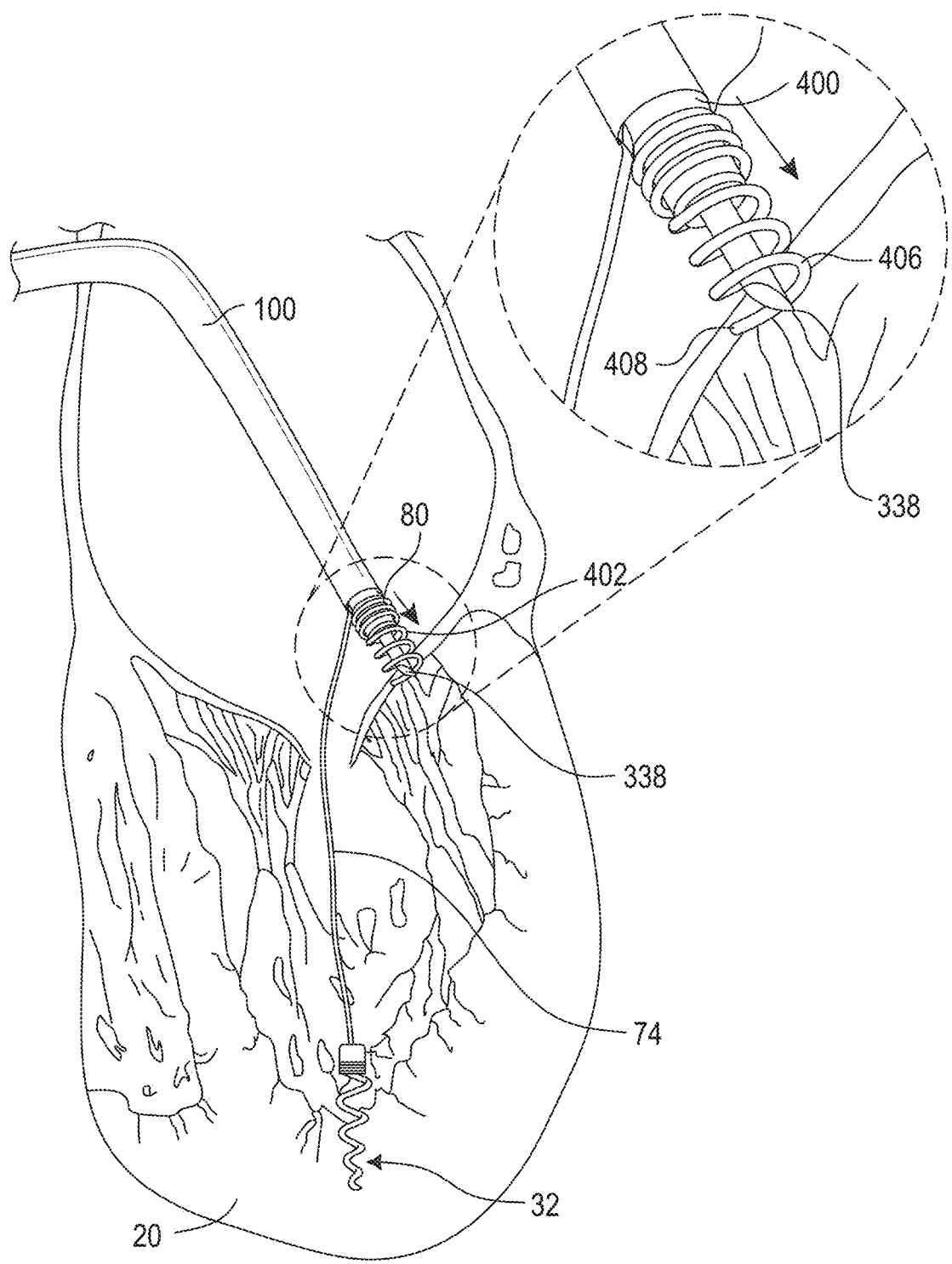
FIG. 3 illustrates the deployment end of a catheter positioned to engage a leaflet of the mitral valve, in accordance with an embodiment.

FIGS. 3-6 depict the deployment of the leaflet anchor. Referring to FIG. 3, the ventricular anchor 32 has been deployed and is tethered to the catheter 100 by a ventricular anchor suture 74 and the ventricular anchor subsystem has been removed. The leaflet anchor is carried within a needle 338, shown aimed at a target site on the atrial side of the leaflet. The needle 338 is axially reciprocally carried within the catheter 100, such as within a tubular sleeve or leaflet anchor catheter 332 advanceable through the catheter 100. Additional details of the needle and needle driver are discussed below.

Figure 4:
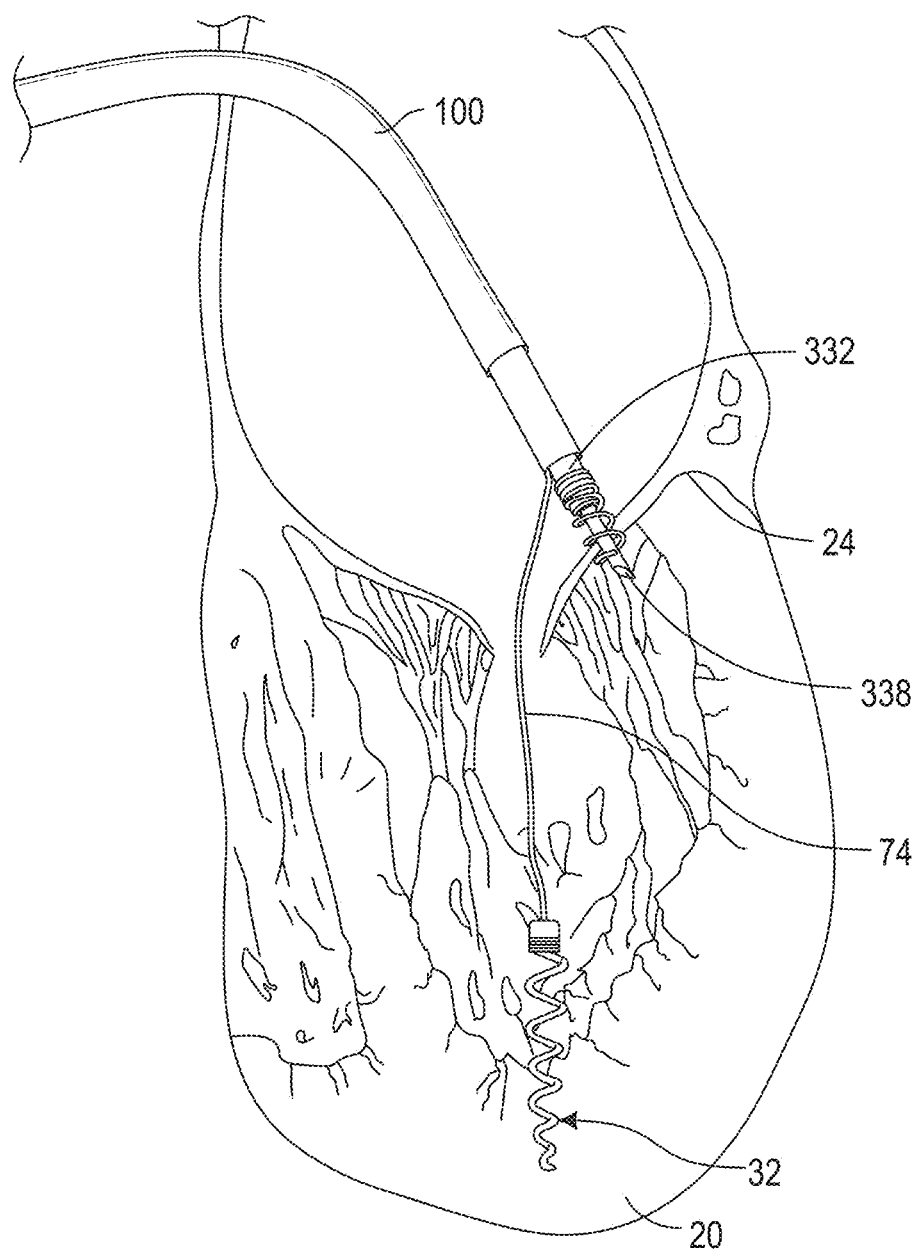
FIG. 4 illustrates the leaflet captured by the helical leaflet anchor, and a needle crossing through the leaflet from the atrium to the ventricle, in accordance with an embodiment.

As shown in FIG. 3, in the illustrated arrangement, the needle can cross through the leaflet from the atrium to the ventricle and a preloaded suture can then be advanced into the ventricle. The suture can then be used to collapse the pledget against the ventricular side of the leaflet to anchor the suture to the leaflet as shown in FIG. 4. Thus the pledget forms a radially enlargeable leaflet anchor. In certain embodiments, other forms of a radially enlargeable leaflet anchor can be used.

Figure 5:
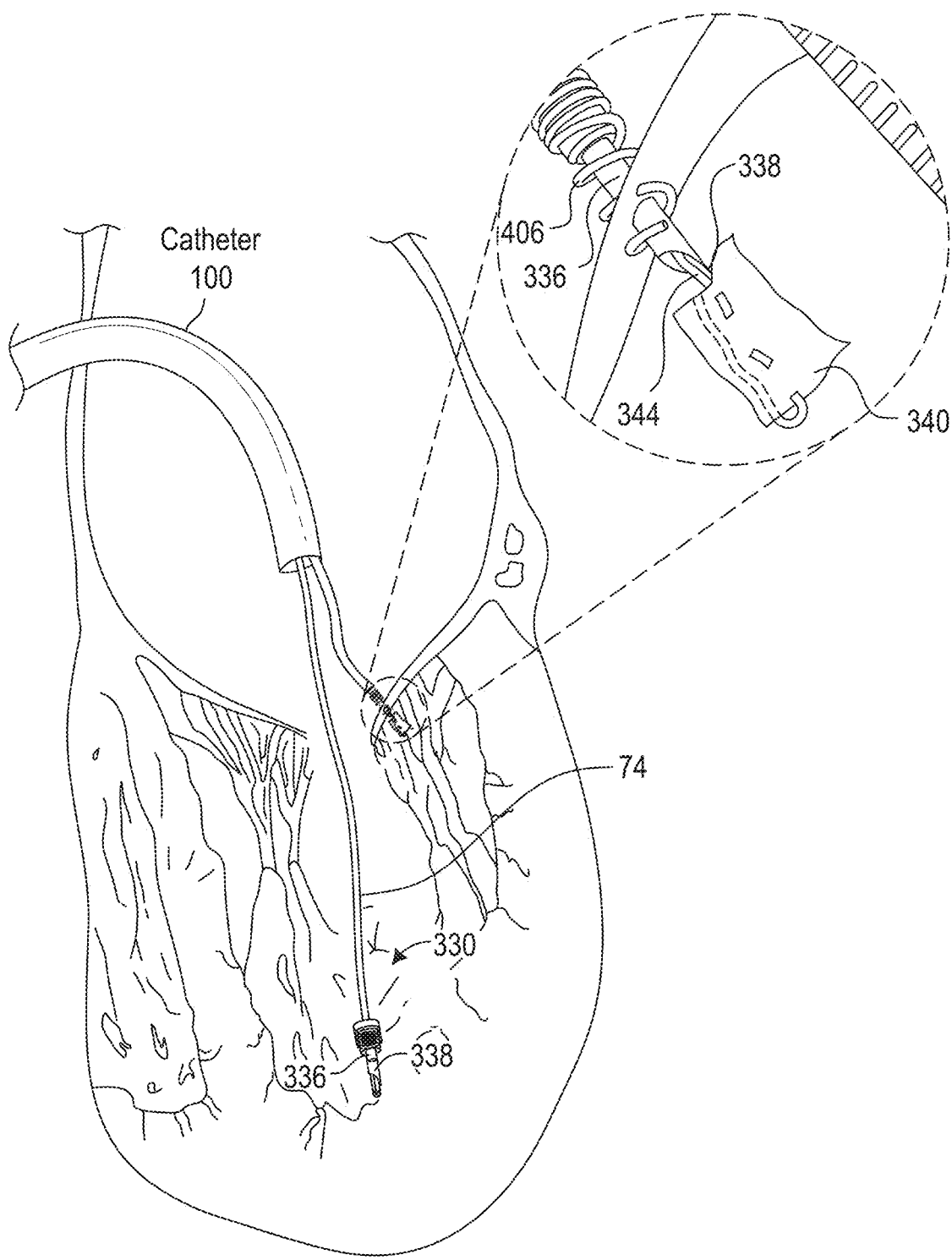
FIG. 5 illustrates a pledget type leaflet anchor deployed from the needle and into the ventricle, in accordance with an embodiment.

The leaflet anchor and suture can then be used in combination with a ventricular anchor, suture and suture lock to effectively create a new mitral chord as shown in FIG. 5. As noted above, the leaflet anchor and suture can be used in combination with the systems and methods for the transvascular prosthetic chordae tendinae implantation disclosed in the U.S. patent application Ser. No. 15/858,671 (the entirety of which is incorporated by reference herein) and the various embodiments of ventricular anchors, sutures and suture locks disclosed therein.

The leaflet anchor deployment subassembly may be provided with a temporary anchor for capturing and stabilizing the leaflet while the needle tip 338 is advanced therethrough at a target side. As illustrated in FIG. 3 and FIG. 4, a distal end 400 of delivery tube 332 or other system component carries a temporary tissue anchor such as a helical tissue anchor 402. Anchor 402 may be similar to ventricular anchor 54 except that temporary anchor 402 does not have a distal barb since it is intended to be only momentarily in engagement with the leaflet. The anchor 402 thus comprises a helical element 406 which terminates in a distal tip 408.

In use, the distal tip 408 is positioned at a target site on the surface of the leaflet, and the helical element 406 is rotated about or around its axis to engage and penetrate the leaflet. The needle tip 338 may be optionally engaged with the leaflet prior to rotation of the helical element 406, and utilized to stabilize the anchor against moving away from the target site in response to rotation, in a manner similar to that discussed in connection with the ventricular anchor and FIGS. 2A and 2B.

Following engagement of the helical element 406 to capture the leaflet from the atrial side and secure the leaflet to the catheter, the needle may be advanced distally through the central lumen defined by the helical element 406 and completely through the leaflet so that the needle tip 338 exits the ventricular side of the leaflet as seen in FIG. 4. An anchor deployment actuator such as a pusher extending through the needle may be utilized to deploy the anchor from the needle and into the ventricle.

Figure 7:
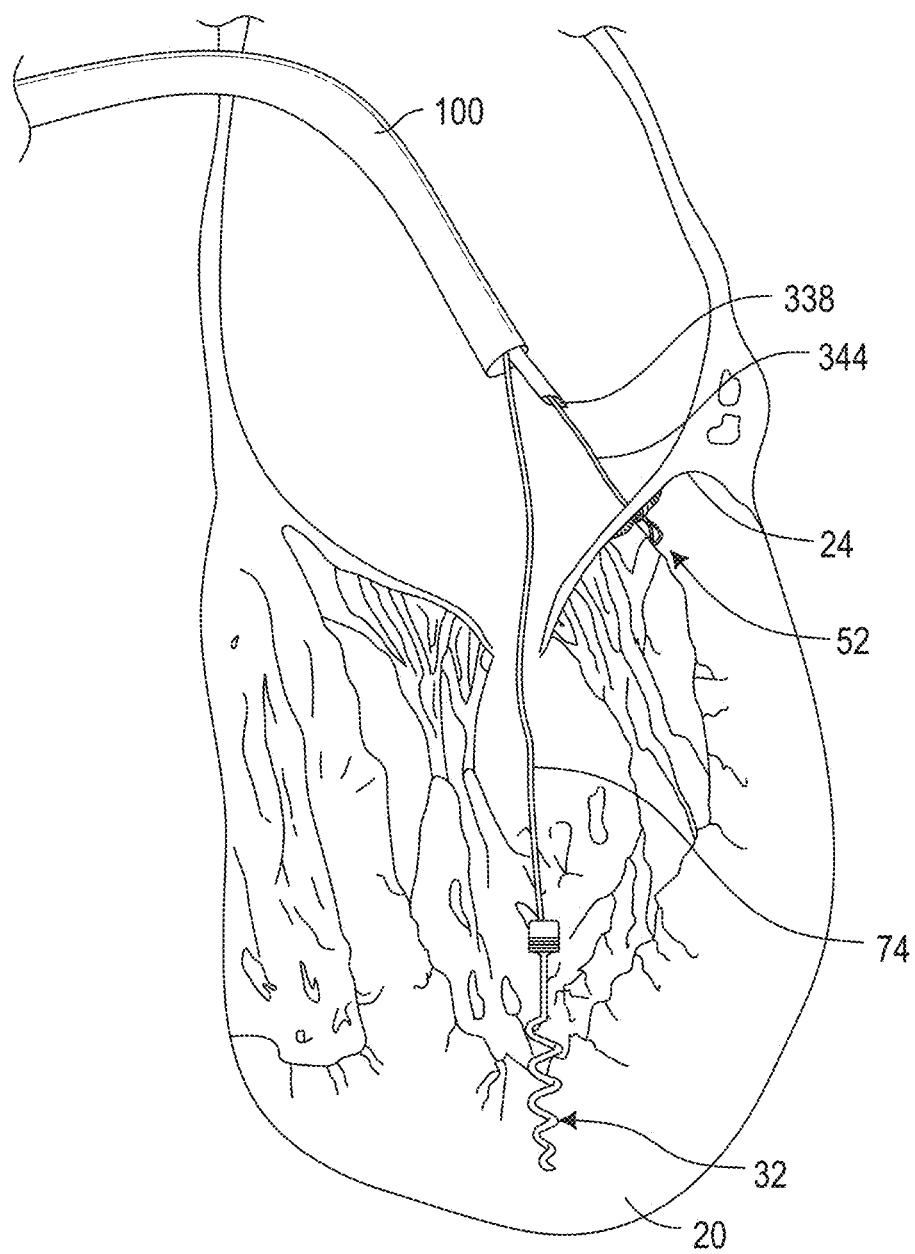
FIG. 7 illustrates a deployed leaflet anchor and suture and a deployed ventricular anchor and suture ready for tensioning and attachment of a suture lock, in accordance with an embodiment.
Figure 8:
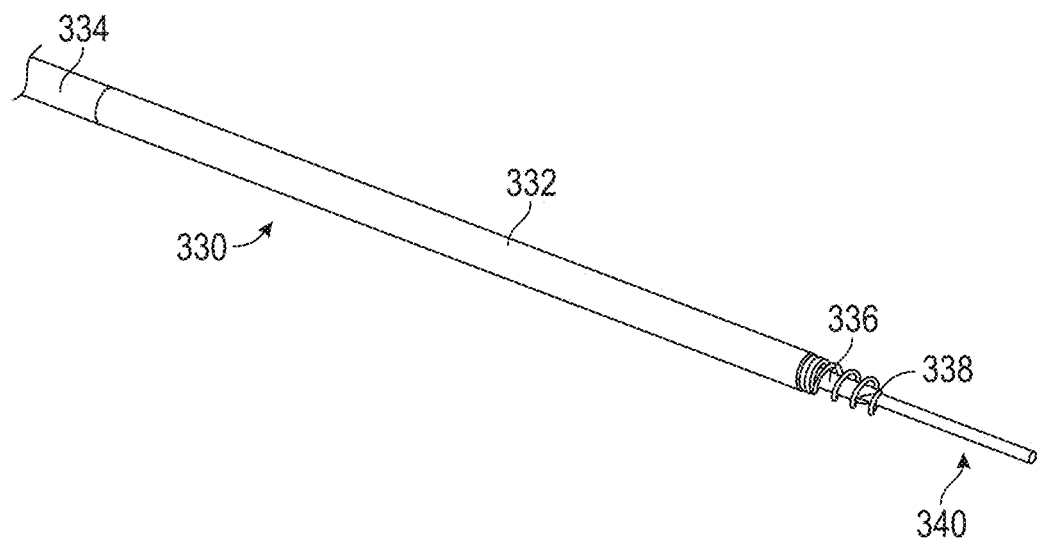
FIG. 8 illustrates a perspective view of a distal end of the leaflet anchor delivery subsystem, in accordance with an embodiment.
Figure 10:
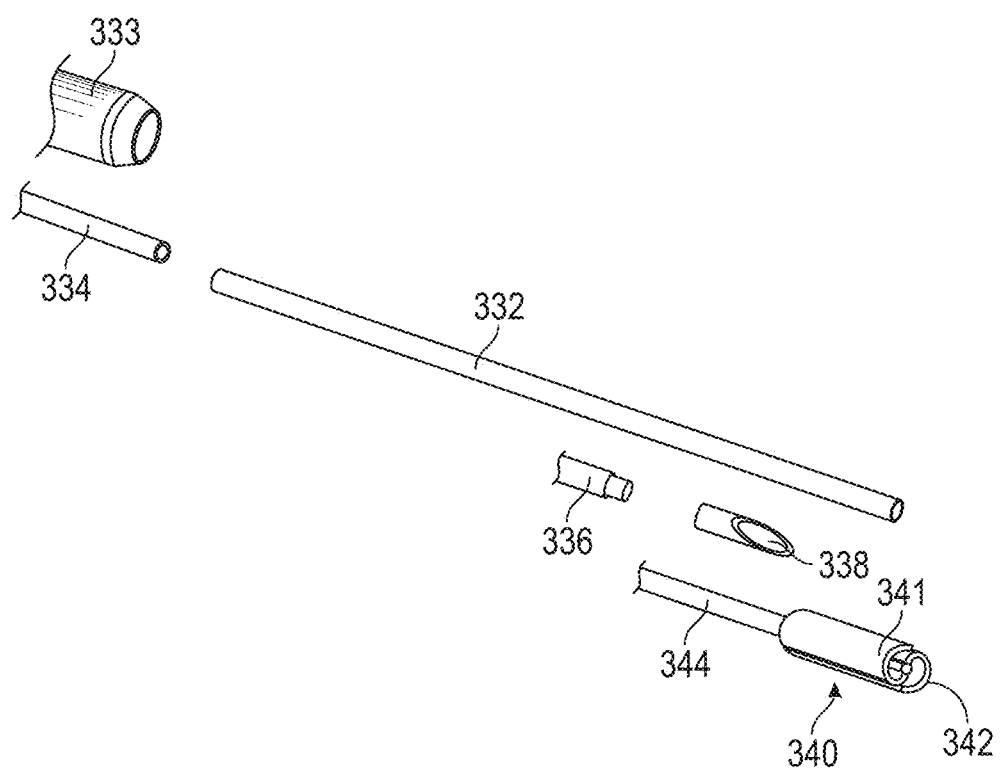
FIG. 10 illustrates an exploded view of the distal end of the leaflet anchor delivery subsystem, in accordance with an embodiment.

Referring to FIG. 5, the leaflet anchor may be a pledget 340 similar to those described elsewhere herein. The pledget 340 may be coupled or attached to the distal end of a leaflet anchor suture 344. The pledget may comprise a soft and/or flexible material such as a fabric. The suture 344 may extend through the needle 336. The pledget 340 may be folded or compressed in a conformation comprising a reduced radial cross section such that it may be disposed within the needle 336 for delivery, as shown in FIGS. 8 and 10 discussed below. The pledget 340 may expand from a reduced cross section to assume a larger radial cross section upon deployment from the distal end of the needle tip 338, as shown in FIG. 5. In some embodiments, the pledget 340 may be pushed through the needle 336 via a push wire or release wire (not shown). Upon delivery through the needle tip 338, proximal retraction of the leaflet suture 344 as shown in FIG. 6 may cause the leaflet anchor to assume an axially collapsed, radially enlarged conformation which prevents the leaflet anchor from being retracted through the puncture in the leaflet and thereby anchors the leaflet suture 344 to the leaflet, as shown in FIG. 7.

Figure 6A:
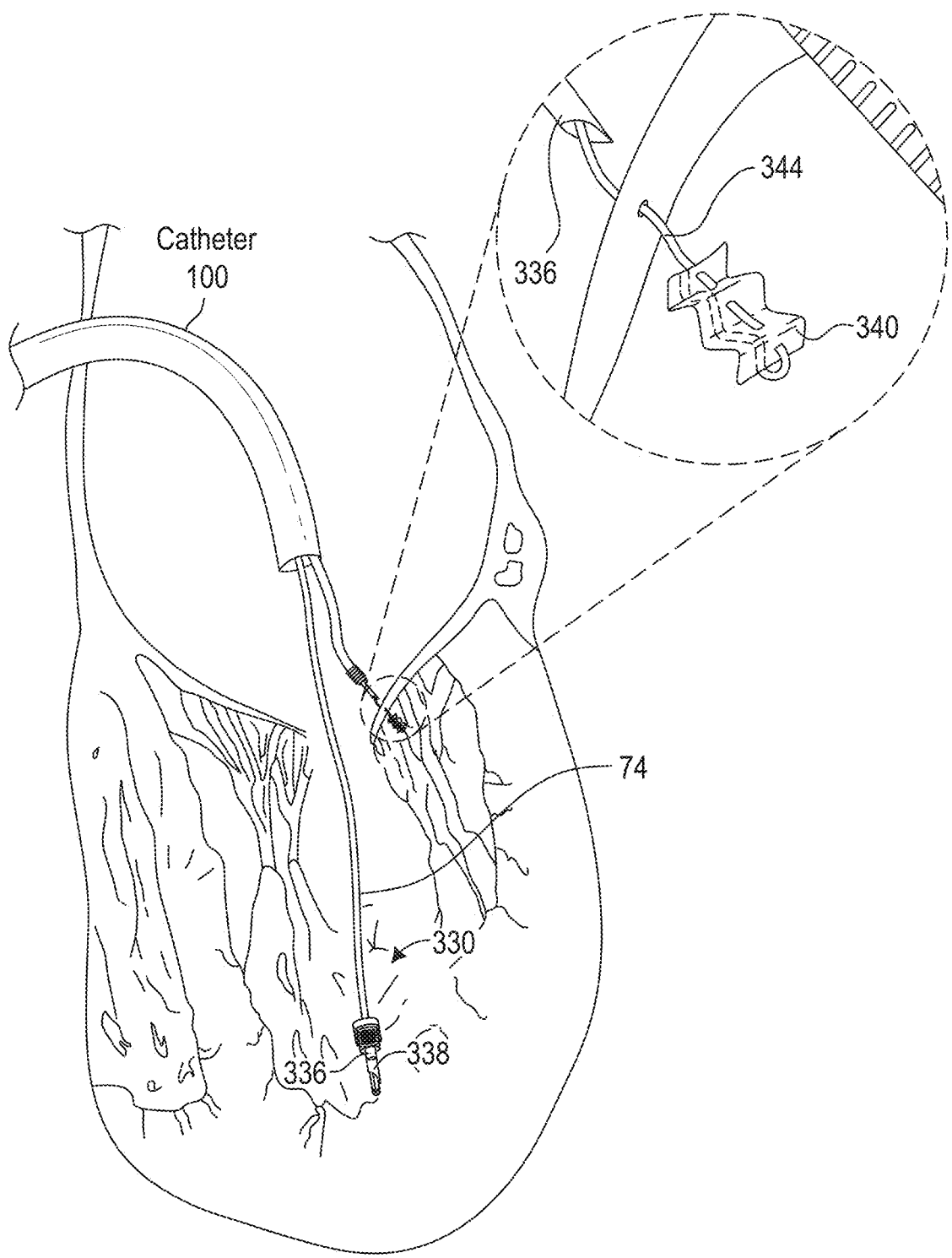
FIG. 6A illustrates proximal traction on a leaflet suture to collapse the pledget against the ventricular side of the leaflet, in accordance with an embodiment.

FIGS. 6A-6D schematically depict a pledget 340 connected to the distal end of a leaflet suture 344. The pledget 340 may comprise two wings 341, 342, which may be rolled/folded (e.g., both in a clockwise or counterclockwise direction) around a longitudinal axis of the pledget 340 to form a reduced cross section conformation. In some embodiments, the leaflet suture 344 may be integrally formed with the pledget 340. In order to produce a foldable or collapsible configuration, the suture 344 may extend distally through the pledget, loop around the distal end of the pledget and return proximally and threaded back through one or more apertures (e.g., two apertures, three apertures, four apertures, etc.) formed in the pledget 340, as shown in FIG. 6A. In some embodiments, the apertures may be aligned along a center of the pledget 340.

The apertures may extend through the pledget 340 and through the portion of the embedded portion of the suture 344 which is integral with the pledget 340. The embedded portion of the suture 344 may be at least partially flatted within the pledget 340. In some embodiments, the apertures may be placed substantially near the center of the pledget (e.g., immediately to the left or right of the embedded suture 344 or alternating between the left and right side of the suture 344). When deployed the suture 344 may be effectively joined to a distal end of the pledget 340 (e.g., the suture 344 may loop back to where it inserts between the pledget sheets).

Figure 6B:
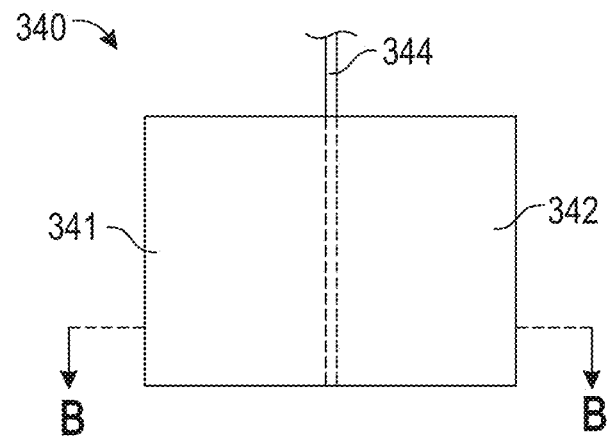
FIGS. 6B-6D illustrate details of a pledget type leaflet anchor, in accordance with an embodiment.
Figure 6C:
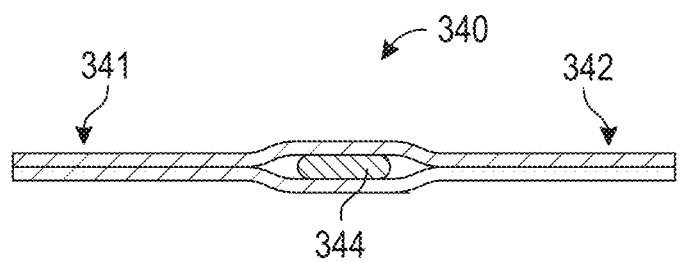
Figure 6D:
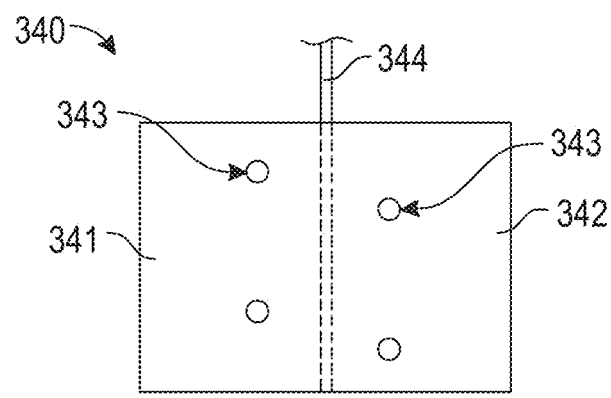

FIGS. 6B-6D schematically depict an example of a pledget as described elsewhere herein. FIG. 6B schematically depicts a pledget 340 formed by affixing a distal end (shown in dashed lines) of the suture 344 between two flat sheets, such that the sheets for left and right wings 341, 342. FIG. 6C shows a cross-section of the pledget 340 along the axis of B-B illustrated in FIG. 6B. In some embodiments, the suture 344 may be inserted between two sheets (e.g., substantially down the middle of the sheets) and pressed and/or laminated to join the three components together (e.g., under heat and/or pressure). At least one of the layers may be partially sintered. The suture 344 may be flattened and/or densified to improve resistance to suture tear out. The sheets may be flat polytetrafluoroethylene (PTFE) sheets (e.g., thin uncured expanded PTFE (ePTFE) sheets) or any other suitable material. In some implementations, the leaflet suture 344 may be disposed between the sheets in alternative configurations, such as a zig-zag or s-shaped configuration. FIG. 6D shows the pledget 340 of FIG. 6B comprising a plurality of apertures 343 through which the proximal tail end of the suture 344 may be threaded through.

In some embodiments, one or more apertures 343 may be formed through the pledget, in various configurations, to form a collapsible structure, as described elsewhere herein, which is configured to anchor the suture 344 against the mitral leaflet. FIG. 6D shows apertures 343 alternating around opposing sides of the suture 344. In some embodiments, the apertures 343 may be formed on the same side of the suture 344 (e.g., in wing 341 or wing 342). In some embodiments, the apertures 343 may be formed through the suture 344. The apertures 343 may be aligned along a center of the pledget 340. The apertures 343 may be aligned along the length of the suture 344 (e.g., may form a straight line). The suture 344 may be at least partially flattened between the two opposing sheets, which may facilitate the placement of apertures 343 through the suture 344. Various combinations of apertures 343, including the positioning described above, may be used.

The pledget 340 may be formed such that the wings 341, 342 are approximately the same size or they may be formed to be different sizes. Upon proximal retraction of the leaflet suture 344, the pledget 340 may be folded to assume an accordion-like conformation, as depicted in FIG. 6A. The pledget 340 may assume a conformation comprising a substantially planar proximal surface which is approximately perpendicular to the longitudinal axis of the leaflet suture 344. This conformation may facilitate anchoring the suture 344 in the leaflet. Upon anchoring the leaflet suture 344 in the leaflet, the leaflet anchor delivery subsystem 340 may be withdrawn from the delivery catheter 100. The leaflet anchor delivery components may be proximally retracted over a proximal end of the suture 344, which may remain extending through the delivery catheter 100 to the leaflet anchor 340, alongside the ventricular anchor suture 74.

Figure 9:
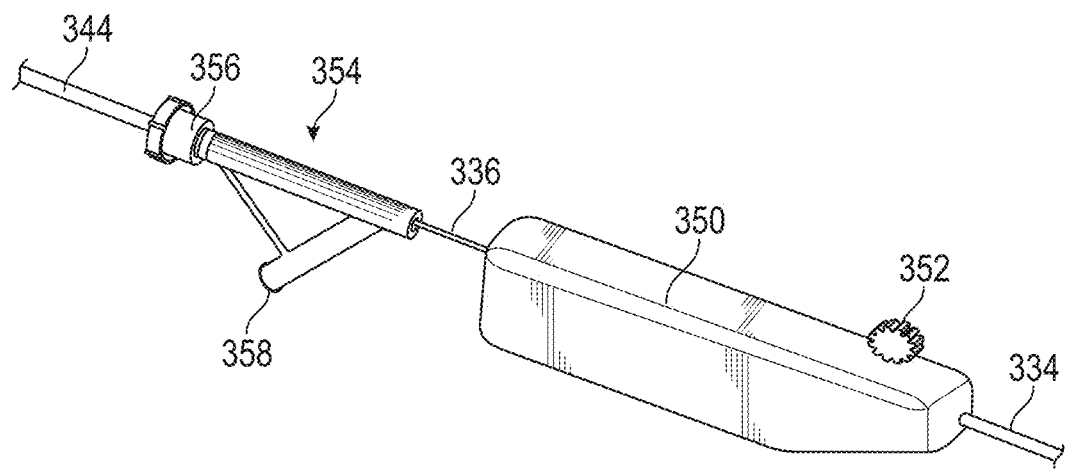
FIG. 9 illustrates a perspective view of a proximal end of the leaflet anchor delivery subsystem, in accordance with an embodiment.

FIGS. 8-10 illustrate various views of the leaflet anchor delivery subsystem 330 and its components. FIG. 8 depicts a perspective view of a distal end of the subsystem 330. FIG. 9 depicts a perspective view of a proximal end of the subsystem 330. FIG. 10 depicts an exploded view of the distal end of the subsystem 330.

As shown in FIGS. 8 and 10, the leaflet anchor delivery subsystem 330 may comprise an outer delivery tube 332. The tube 332 may optionally include a deflection zone and may be configured to be steerable by an operator such as by proximal retraction of one or two or more pull wires (not shown) along various sides of the flex tube 332. The operator may control the flexion of the flex tube via a knob 352 or lever or other actuation mechanism positioned on a handle 350 at the proximal end of the leaflet anchor delivery subsystem 330, as shown in FIG. 9.

An internal tubular shaft or needle 336 terminating at a distal end with a needle point 338 may extend through the delivery tube 332. The internal needle 336 may comprise a hypotube, extrusion or braided tube or catheter which is flexible enough to conform to the shape of the optional flex tube 332. A needle tip 338 may be coupled to the distal end of the internal flexible shaft 336. A flexible jacket 333 may surround the flex tube 332 and a delivery shaft 334.

The proximal end of the internal tubular shaft 336 may be connected to a needle handle 354, as shown in FIG. 9. The needle handle 354 may comprise a hemostasis valve 356. The leaflet suture 344 may be inserted through valve 356. Valve 356 may be a tuohy-borst valve. The needle handle 354 may include additional ports 358 for accessing the lumen of the internal flexible shaft 336. The needle handle 354 may be positioned proximally to the handle 350 such that the internal flexible shaft 336 extends through the handle 350 and into the lumen of the delivery shaft 334. The handle 350 may comprise a hemostasis valve for receiving the internal flexible shaft 336 and sealing the internal components of the handle, including the opening to the delivery shaft 334, from the ambient environment.

The needle tip 338 may be extendable and retractable by extending the needle handle 354 toward the handle 350 or retracting the needle handle 354 from the handle 350, respectively. Distal advance of the needle 336 may be accomplished by manually advancing the handle 354. Alternatively, the distal advance of the needle may be assisted by a mechanical or electromechanical mechanism to produce a relatively high velocity, low stroke length distal advance.

Exertion of pressure on the leaflet when the needle tip 338 is extended distally beyond the tube 332 may cause the needle tip 338 to puncture the leaflet such that the needle tip 338 may extend through to the opposite side (e.g., the atrial side) of the leaflet, as shown in FIG. 4. This pressure may be exerted by extending the needle tip 338 and/or retracting the entire delivery device 330 in a proximal direction with the needle tip 338 in an extended position.

The ventricular anchor suture 74 and the leaflet anchor suture 344 may be coupled together in a tensioned fashion to form the neo chordae implant or to join two sections of the neo chordae implant together, such that the neo chordae extends between the ventricular anchor 302 and the leaflet anchor 340 across the atrial side of the coaptive edge of the leaflet. The overall length of the neo chordae may be adjusted by proximal traction of one or both sutures 74, 344 prior to engaging the suture lock 376 such that an appropriate tension is applied to the leaflet, with the tension subsequently maintained by the ventricular anchor 302. The sutures 74, 344 may remain extending proximally through the delivery catheter 100 to a location outside the body. In some embodiments, the proximal ends of the suture 74, 344 may be fed into a handle or proximal portion of a suture lock delivery system 370 to facilitate placement of the suture lock and cutting of the sutures 74, 344. In some embodiments, the proximal ends may remain free or coupled or secured by other means.

Figure 11:
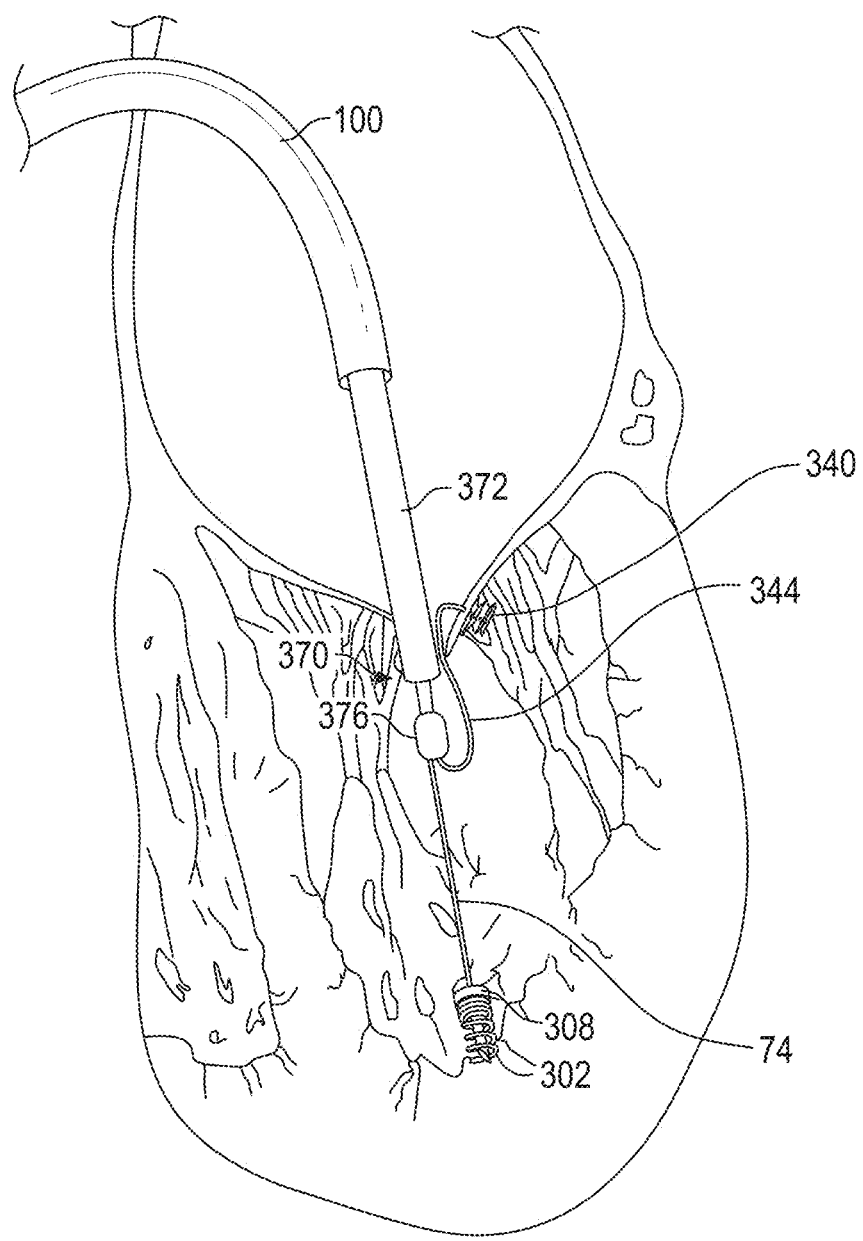
FIG. 11 depicts advancing a suture lock via a suture lock delivery subsystem over the leaflet anchor suture and ventricular anchor suture to connect the leaflet anchor to the ventricular anchor, in accordance with an embodiment.
Figure 12:
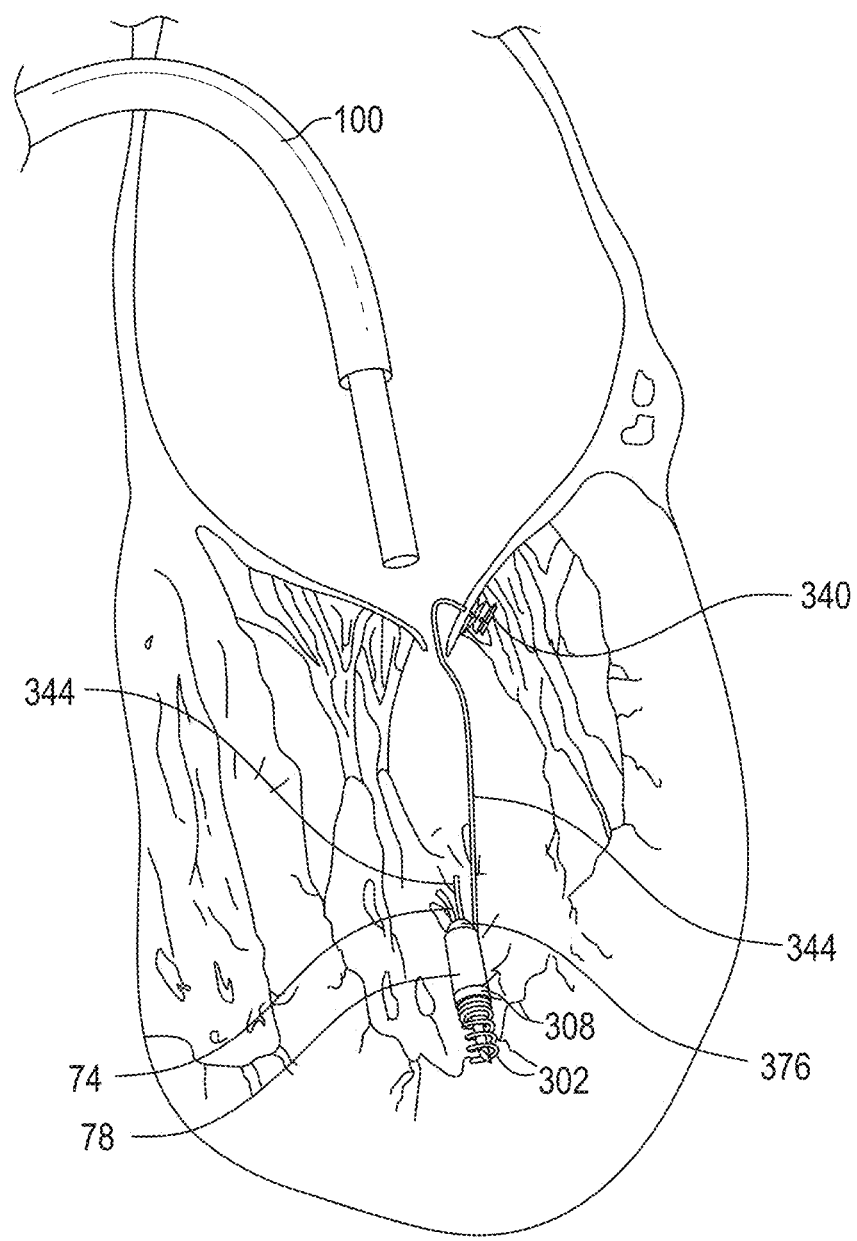
FIG. 12 depicts the suture lock in a locked position after the tension has been adjusted and the suture tails having been severed, in accordance with an embodiment.

FIG. 11 depicts the advancement of suture lock 376 over the ventricular anchor suture 74 and the leaflet suture 344. The suture lock delivery subsystem 370 may be advanced through the delivery catheter 100 and a tubular pusher catheter 372 may push a suture lock 376 along the distal direction of the sutures 74, 344. Once the suture lock 376 has reached the ventricle, it can continue to be pushed along the ventricle suture 74 with proximal traction on the suture 74 and while allowing the leaflet suture 344 to feed distally through the catheter if needed for the suture lock 376 to advance distally to the ventricular anchor. As discussed further below, FIG. 12 illustrates the final construct with the leaflet anchor and ventricular anchors tethered together to form an artificial chordae. The proximal tails of the two sutures has been severed and catheter proximally retracted from the ventricle through the mitral valve.

Figure 13:
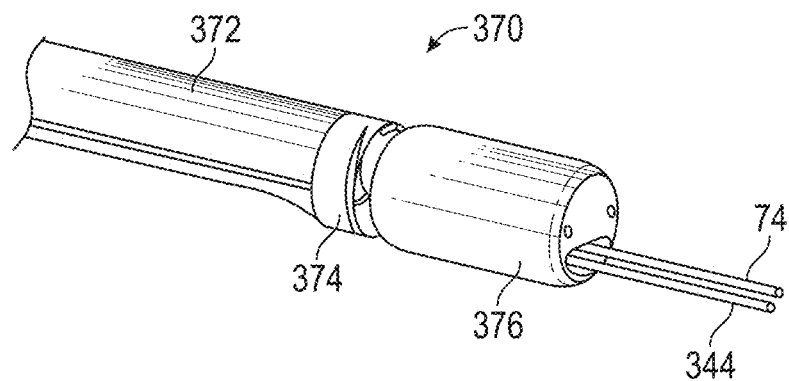
FIG. 13 depicts a perspective view of a distal end of the suture lock delivery subsystem, in accordance with an embodiment.
Figure 14:
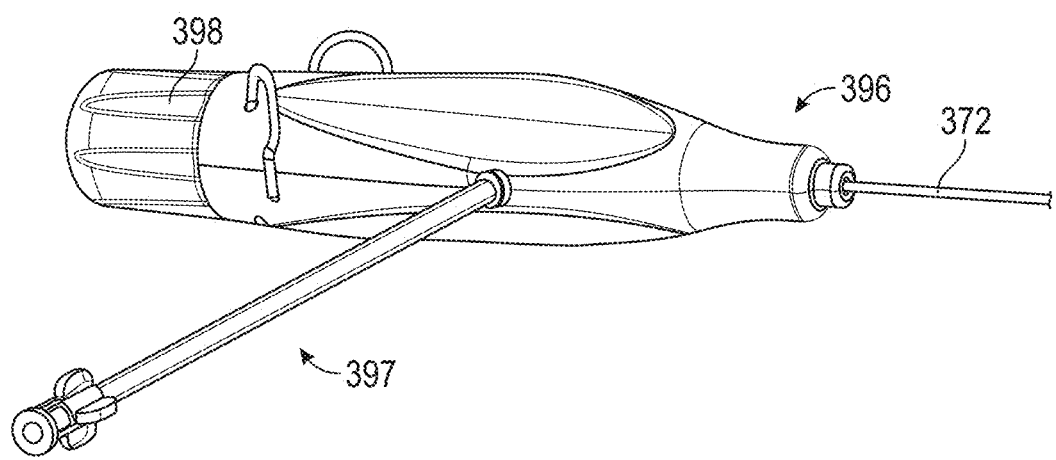
FIG. 14 depicts a perspective view of a proximal end of the suture lock delivery subsystem, in accordance with an embodiment.
Figure 15:
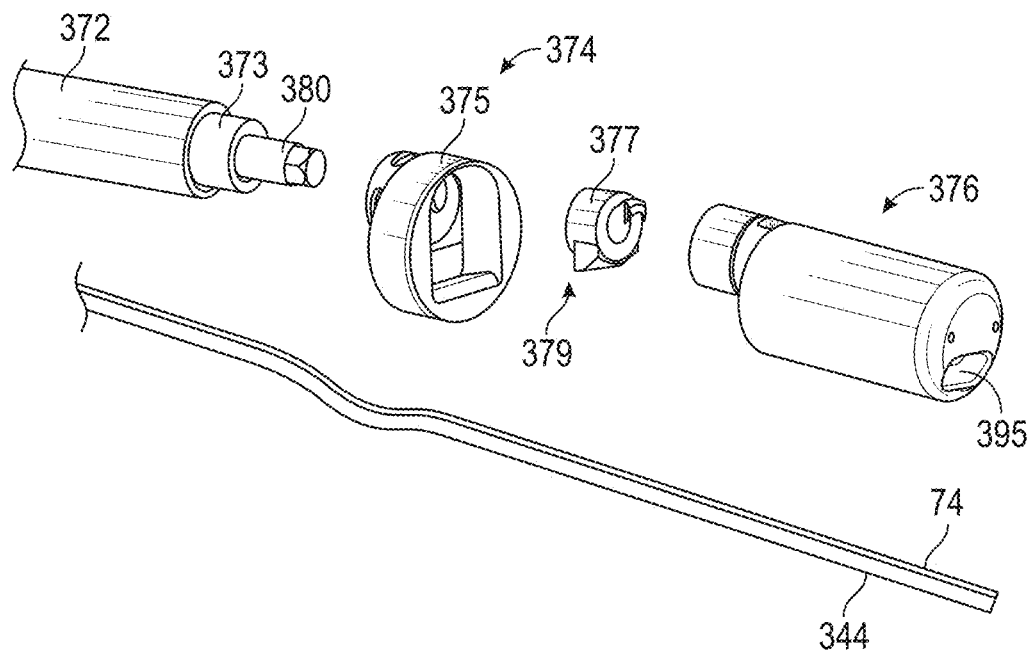
FIG. 15 depicts a partially exploded view of the distal end of the suture lock delivery subsystem, in accordance with an embodiment.
Figure 16:
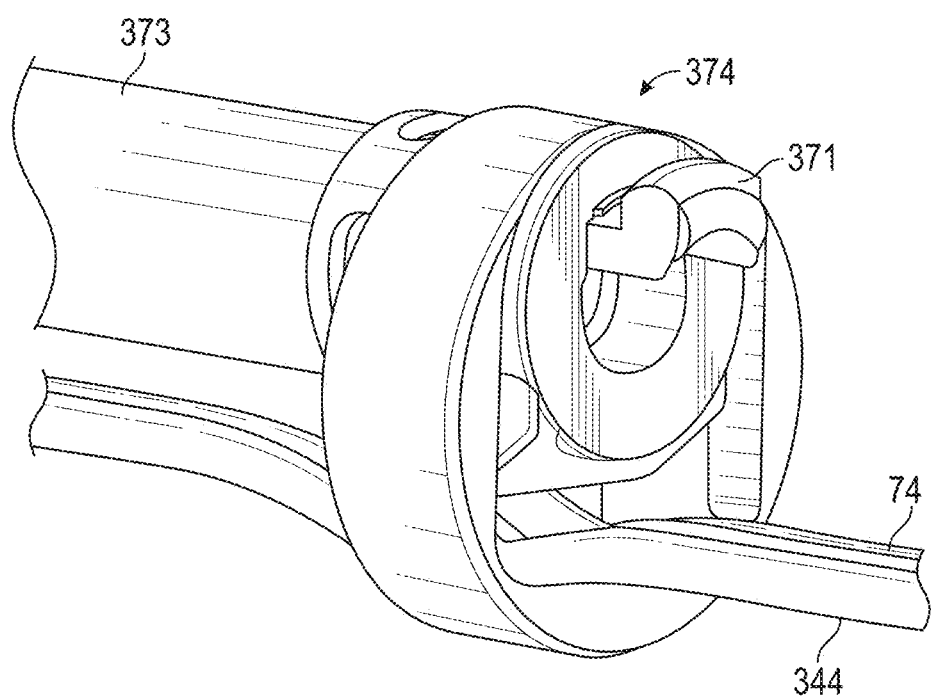
FIG. 16 depicts a perspective view of a distal end of a suture cutting assembly, in accordance with an embodiment.
Figure 17:
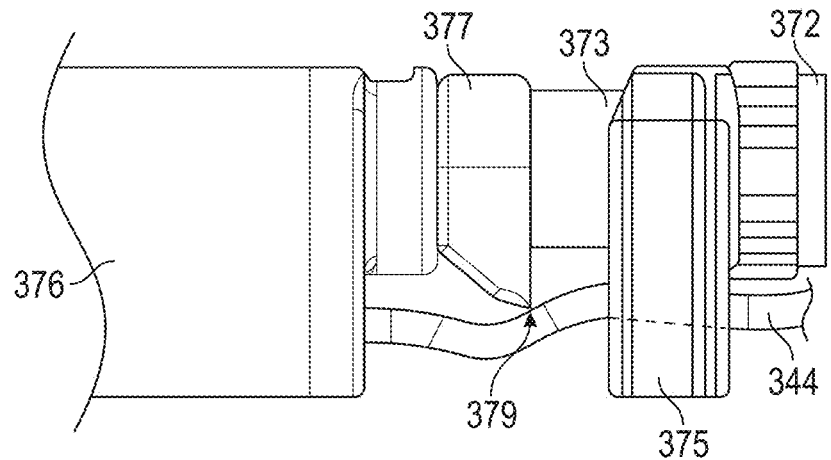
FIG. 17 depicts a side view of a cutting assembly portion of the suture lock delivery subsystem in a configuration where the cutting head is not yet advanced for holding the sutures prior to being severed, in accordance with an embodiment.
Figure 18:
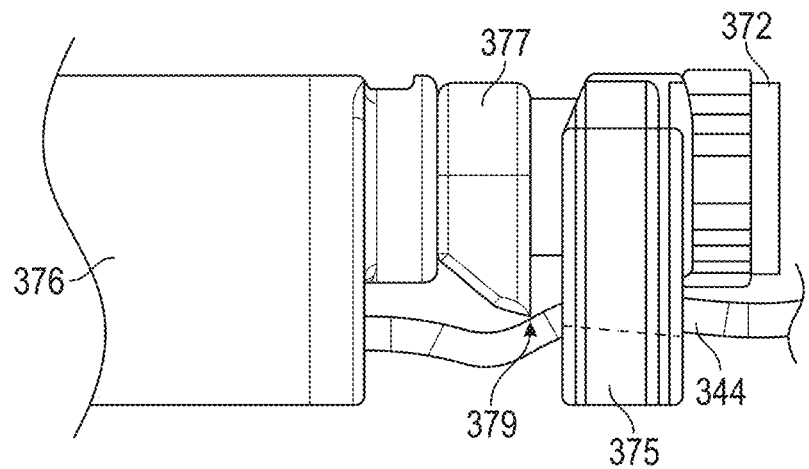
FIG. 18 depicts a side view of the cutting assembly portion of the suture lock delivery subsystem in a configuration where the cutting head has been advanced for severing the sutures, in accordance with an embodiment.
Figure 19:
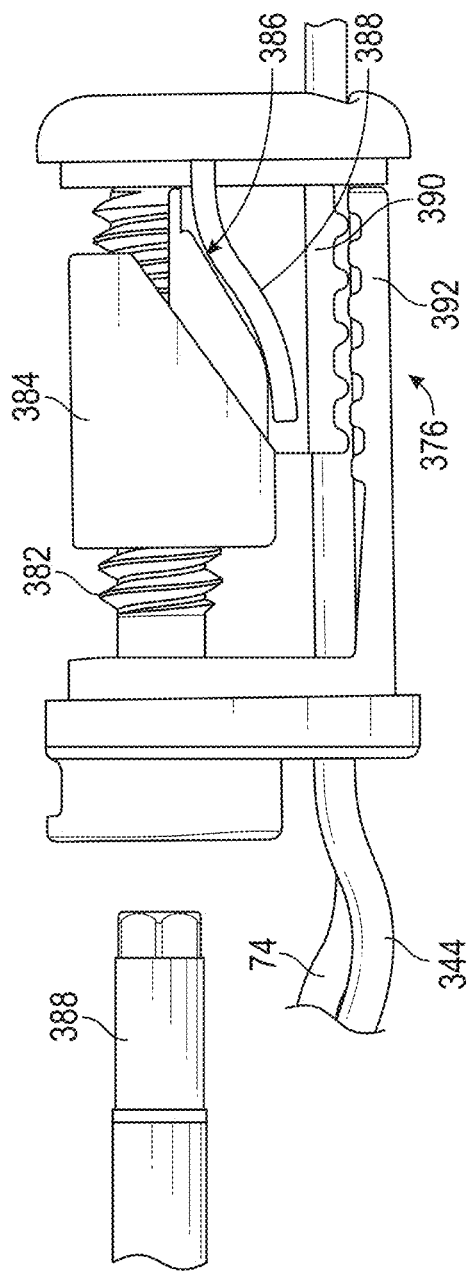
FIG. 19 depicts a side view of a suture lock and a distal end of a torque driver configured to engage the suture lock, in accordance with an embodiment.
Figure 20:
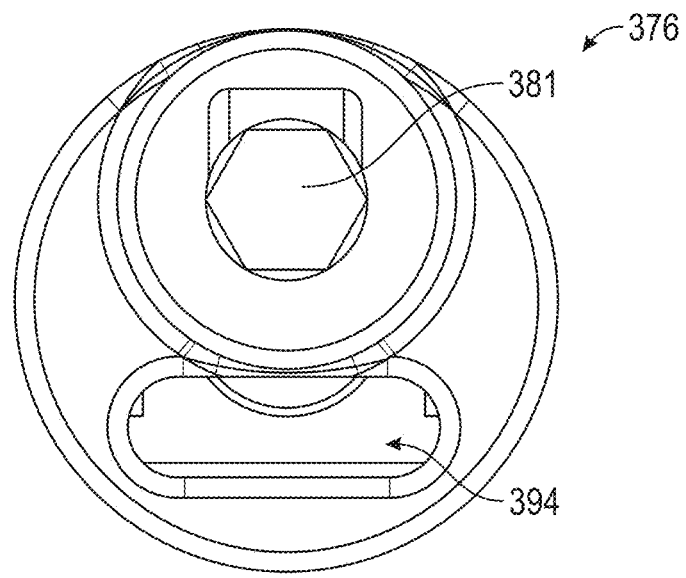
FIG. 20 depicts a proximal end view of a suture lock, in accordance with an embodiment.
Figure 21:
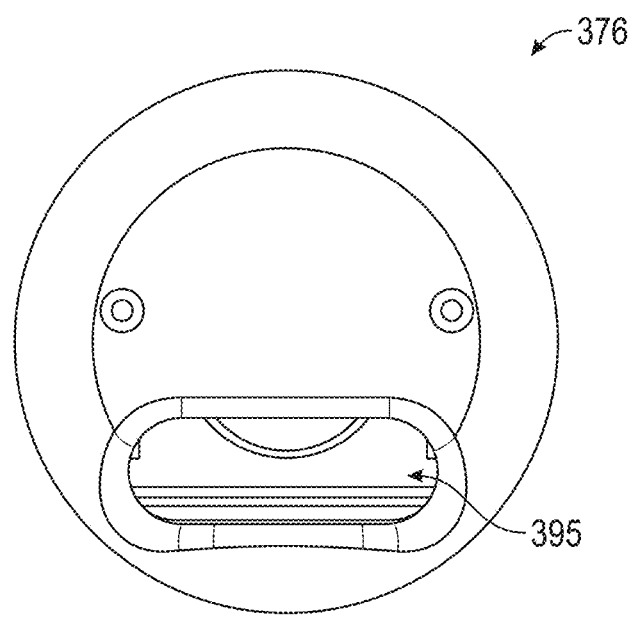
FIG. 21 depicts a distal end of view of a suture lock, in accordance with an embodiment.

FIGS. 13-14 illustrate various views of the suture lock delivery subsystem 370 and its components. FIG. 13 depicts a perspective view of a distal end of the subsystem 370. FIG. 14 depicts a perspective view of a proximal end of the subsystem 370. FIG. 15 depicts a partially exploded view of the distal end of the subsystem 370. FIG. 16 depicts a perspective view of a distal end of a cutting assembly. FIGS. 17 and 18 depict side views of a cutting assembly portion of the subsystem 370. FIG. 19 depicts a side view of a suture lock 376 and a distal end of a torque driver 388 configured to engage the suture lock 376. FIGS. 20 and 21 depict a proximal end view and a distal end view, respectively, of the suture lock 376.

The suture lock delivery subsystem 370 may be configured to advance (e.g., slide) a suture lock 376 over both the sutures 74, 344 (or even three or four or additional sutures) securing them together. The sutures 74, 344 may each be proximally retracted relative to the suture lock 376 to tension the sutures 74, 344 and modulate the length of each suture 74, 344 between the suture lock 376 and the respective tissue anchors 302, 340. Once the tension and length of the neo chordae implant is optimized, the suture lock 376 may be locked to fix the length of the sutures 74, 344 such that the sutures 74, 344 can no longer move with respect to the suture lock 376. The sutures 74, 344 may then be severed at a point proximal to the suture lock 376. The suture 74, 344 may be cut by the same suture lock delivery subsystem 370 which delivered the suture lock 376. In other embodiments, a separate cutting device may be inserted into the delivery catheter 100 after the suture lock has been locked in place.

The suture lock allows one or two or more sutures to be advanced therethrough and adjusted, and then locked with sufficient clamping efficiency that an ePTFE suture can be prevented from slipping from the suture lock under normal use conditions (e.g., withstand tension of at least about 60% or 80% or more of the suture breaking strength, without slipping). In certain example embodiments, the suture lock allows one or two or more sutures to be advanced therethrough and adjusted, and then locked with sufficient clamping efficiency that an ePTFE suture can be prevented from slipping from the suture lock under normal use conditions (e.g., withstand tension of at least 60% or 80% or more of the suture breaking strength, without slipping). The lock may be reopened to permit readjustment of the tension on the mitral leaflet, and retightened, until a desired result has been achieved. The tightening tool may then be removed, leaving the suture lock behind.

The suture lock 376 may be advanced along the sutures by a retainer catheter 373. The distal end of the retainer catheter 373 may be coupled to a retainer element 377 (FIG. 15). The retainer element may comprise a flange 371 or other mechanical feature configured to engage the suture lock 376. For example, the flange 371 may be inserted into a recess at a proximal end of the suture lock 376. In some embodiments, rotation of the retainer catheter 373 and/or translation substantially perpendicular to the axial direction of the retainer catheter 373 may be used to disengage the retainer catheter 373 from the suture lock 376.

The sutures 74, 344 may extend from their respective tissue anchors to pass through the suture lock 376, entering from a distal opening 395 in a distal face of the suture lock 376, shown in FIG. 21, and exiting at a proximal opening 394 to the suture path in a proximal face of the suture lock 376, shown in FIG. 20. The sutures 74, 344 may extend through a channel in a cutter head 375 proximal to the suture lock 376 and along the outside of the retainer catheter 373 and through the delivery catheter 100. The cutter head 375 may be coupled to the distal end of a cutter catheter 372. The retainer catheter 373 may extend through an internal lumen of the cutter catheter 372 such that the two catheters 372, 373 may be extendable or retractable relative to one another.

Once the sutures 74, 344 are locked (fixedly secured) within the suture lock 376, the proximal ends of the suture 74, 344 may be cut adjacent to the proximal face of the suture lock. The sutures 74, 344 may be cut by advancing the cutter catheter 372 coupled to the cutter head 375 toward the proximal face of the suture lock 376. As schematically illustrated in FIGS. 17-18, as the cutter head 375 advances along the retainer catheter 373 toward the retainer element 377, the cutter head brings the sutures 74, 344 into close proximity to a cutting blade 379 positioned on the retainer element 377. The cutter head 375 is configured to advance over the retainer element 377 in such a fashion that the channel in the cutter head 375 retaining the sutures 74, 344 becomes increasingly spatially occupied by the blade 379. As the blade 379 is forced into the channel of the cutter head 375, the blade 379 shears the sutures 74, 344. Application of proximal tension to the sutures 74, 344 may facilitate the cutting of the sutures 74, 344. In other embodiments, different actuations (e.g., rotation of a cutting catheter) can be configured to sever the sutures 74, 344.

In some implementations, more than two sutures may be employed and may be locked within the suture lock 376 and severed by the suture lock delivery subsystem 370 in the same fashion. In some embodiments, advancement of the cutter head 375 over the retainer element 377 may facilitate the disengagement of the retainer catheter 373 from the suture lock 376. For example, the cutter head 375 may advance to a distal position where it is configured to stabilize the suture lock 376, allowing the retainer catheter 373 to be axially and/or rotationally disengaged from the suture lock 376.

FIG. 19 illustrates a side view of an example of a suture lock 376 (shown with its outer casing/shell removed). The sutures may pass through the suture lock 376 from a distal end to a proximal end as described elsewhere herein. The suture lock 376 may comprise a screw 382 configured to distally advance or proximally retract a push wedge 384, depending on the direction of rotation of the screw. The screw 382 may be rotated by a torque shaft 388. The torque shaft 388 may comprise a driver head configured to mate with recess 381 (e.g., a polygonal recess or other non-circular shaped recess, as shown in FIG. 20) positioned at the proximal end of the suture lock 376 such that rotation of the torque shaft 388 causes rotation of the screw 382. The torque shaft 388 may extend through an internal lumen of the retainer catheter 373. The torque shaft 388 may be rotated at its proximal end by a knob 398 or other actuation mechanism positioned at a proximal end of the subsystem handle 396. The handle 396 may include a hemostasis valve 397. In some implementations, the sutures 311, 344 may pass through the hemostasis valve 397.

Advancement of the push wedge 384 by the torque shaft 388 may cause a ramp or angled surface 386 to gradually compress one or more springs, such as spring pins 388. The springs bias the clamp upward to open the suture path until forced closure by rotation of the torque shaft 388. Compression of the one or more springs 388 may force a clamp 390 downward on the sutures 311, 344, compressing the sutures 311, 344 between two opposing surfaces. In some embodiments, the clamp 390 and the opposing surface 392 may have notched surfaces configured to mate with each other at discrete increments. The mated notched surfaces may provide enhanced friction and, in some implementations, mechanical interference for retention of the sutures 311, 344 between the opposing surfaces such that they cannot be withdrawn, either proximally or distally, from the suture lock 376. In some embodiments, the tightening may be reversible by rotating the torque shaft in an opposite direction.

Once the suture lock is properly positioned over the sutures 74, 344 and locked into place, the sutures 74, 344 may be severed as described elsewhere herein. FIG. 12 depicts the retraction of the suture lock delivery subsystem 370 after the sutures 74, 344 have been cut. Once the suture lock delivery subsystem 370 has been removed from the delivery catheter 100, the delivery catheter 100 may be withdrawn from the body.

Collapsible Anchor Delivery Sheath

Depending on the configuration of the anchor assembly 50, coil 54 and/or tubular sleeve 78, in certain embodiments, the outer profile of the deployed anchor assembly 50 may be larger than the inner diameter of the delivery catheter 100 and/or introducer sheath. Thus, in certain embodiments, the ventricular anchor delivery subsystem 300 described above can be modified as shown in FIGS. 22A-E such that a ventricular anchor delivery subsystem 400 includes a collapsible anchor delivery sheath 404 that can provide protection and support for the anchor assembly 50, coil 54 and/or tubular sleeve 78 during delivery while also being collapsible to fit through the inner diameter of the delivery catheter 100. In this manner, the collapsible anchor delivery sheath 404 can be collapsed to a smaller diameter while the sheath 404 is withdrawn into the delivery catheter 100. Such a collapsible delivery sheath 404 can also be configured to secure the anchor assembly 50 during delivery such that the anchor assembly 50 will not be stripped out of the delivery sheath 404 by, for example, the beating ventricle or other motion or geometries encountered during introduction and placement. The delivery sheath 404 may also in certain embodiments be sufficiently kink resistant to resist movement of the beating ventricle once the coil 54 of the anchor assembly 50 is engaged with the heart wall. As will be described below, the sheath 404 can include a radiopaque tip for detection. The delivery sheath 404 in certain embodiments can have a sufficient inner diameter to retain the coil 54 and tubular sleeve 78 but small enough in outer diameter to fit within the delivery catheter 100 or introducer sheath. In certain embodiments, the anchor delivery sheath 404 is collapsible such that when the anchor assembly 50 is delivered, the sheath 404 may be drawn through the narrower constriction of the delivery catheter 100 without excessive force and without tearing. In certain embodiments, the anchor delivery sheath 404 is adapted to transition in diameter from the size inner diameter of the delivery catheter 100 (for example, in some embodiments, about 9 Fr) to a second, larger, size required to fit the anchor assembly 50 (for example, in some embodiments, about 19 Fr). In certain example embodiments, the anchor delivery sheath 404 is adapted to transition in diameter from the size inner diameter of the delivery catheter 100 (for example, in some embodiments, 9 Fr) to a second, larger, size required to fit the anchor assembly 50 (for example, in some embodiments, 19 Fr)

In one specific non-limiting, exemplary embodiment of the collapsible anchor sheath 404, the sheath comprises an approximately 0.005" wall thermoplastic elastomer material (such as, for example, Pebax) configured into tubes of three different diameters. For example, two relatively shorter pieces can be used to transition the diameter from a smaller diameter catheter (9 French in an embodiment) to a larger diameter for accommodating the anchor assembly 50 (19 French diameter in an embodiment). The third tube can form the collapsible portion of the sheath itself. All three pieces can be formed over a tapered mandrel using a thermal bonding or other suitable forming process. In a further embodiment, a radiopaque marker, such as a polymer radiopaque marker band made from, for example, a thermoplastic elastomer with 60% wt Tungsten that be incorporated with the sheath and thermally or otherwise suitably bonded to the sheath.

FIGS. 22A-F illustrate the ventricular anchor delivery subsystem 400 with the collapsible sheath 404. The ventricular anchor delivery subsystem 400 can be used in the methods and steps described above and with the drive shaft 307, driver head 306 and other components described above for rotating and delivering the anchor assembly 50. The ventricular anchor delivery subsystem 400 can include a sheath 405 having a proximal portion 410, an intermediate portion 412 and a distal portion 414 that can include the collapsible sheath 404. The proximal portion 410 can include a hemostasis valve 416 with a side port 418. In the illustrated embodiment the proximal portion 410 and the intermediate portion 412 of the sheath 405 can be formed from a tube such as a stainless steel hypotube which can have an outer diameter of 9 French. The collapsible sheath 404 can be formed form a separate material that is bonded or otherwise attached to the smaller diameter tube.

Figure 22A:
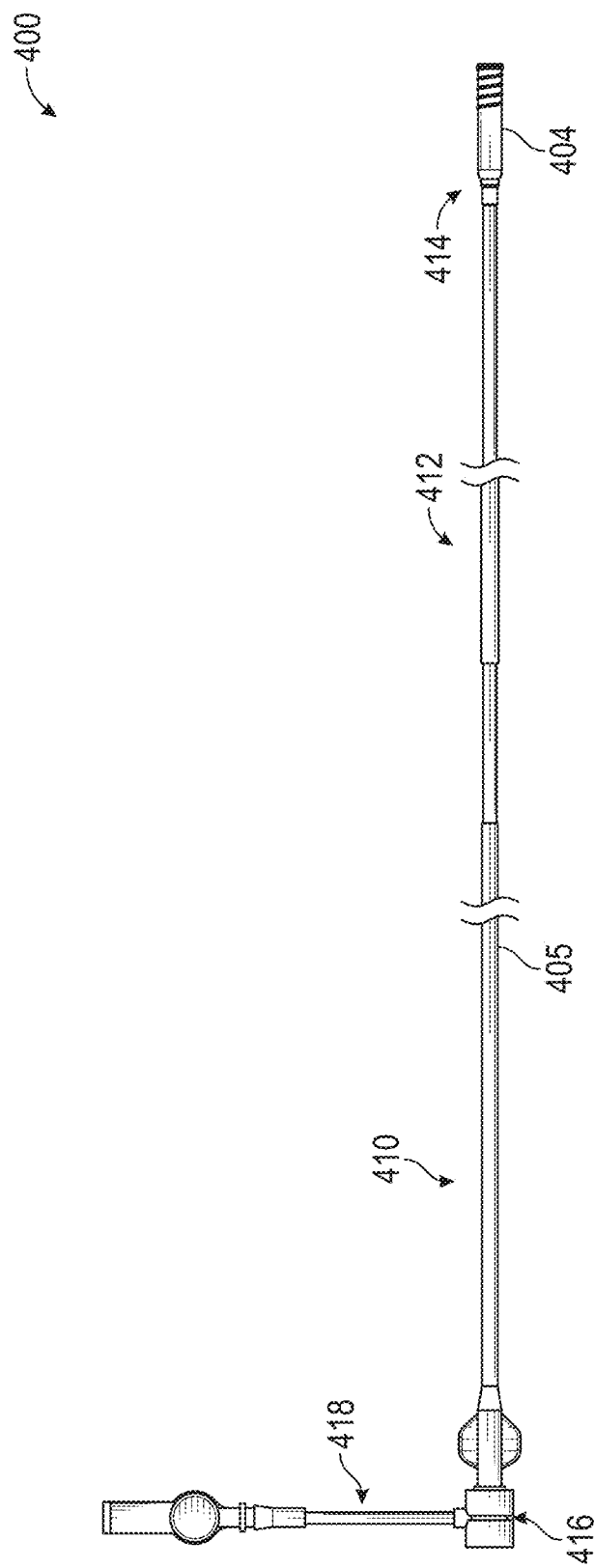
FIG. 22A is a side view of a ventricular anchor delivery subsystem according to aspects of the disclosure, in accordance with an embodiment.
Figure 22B:
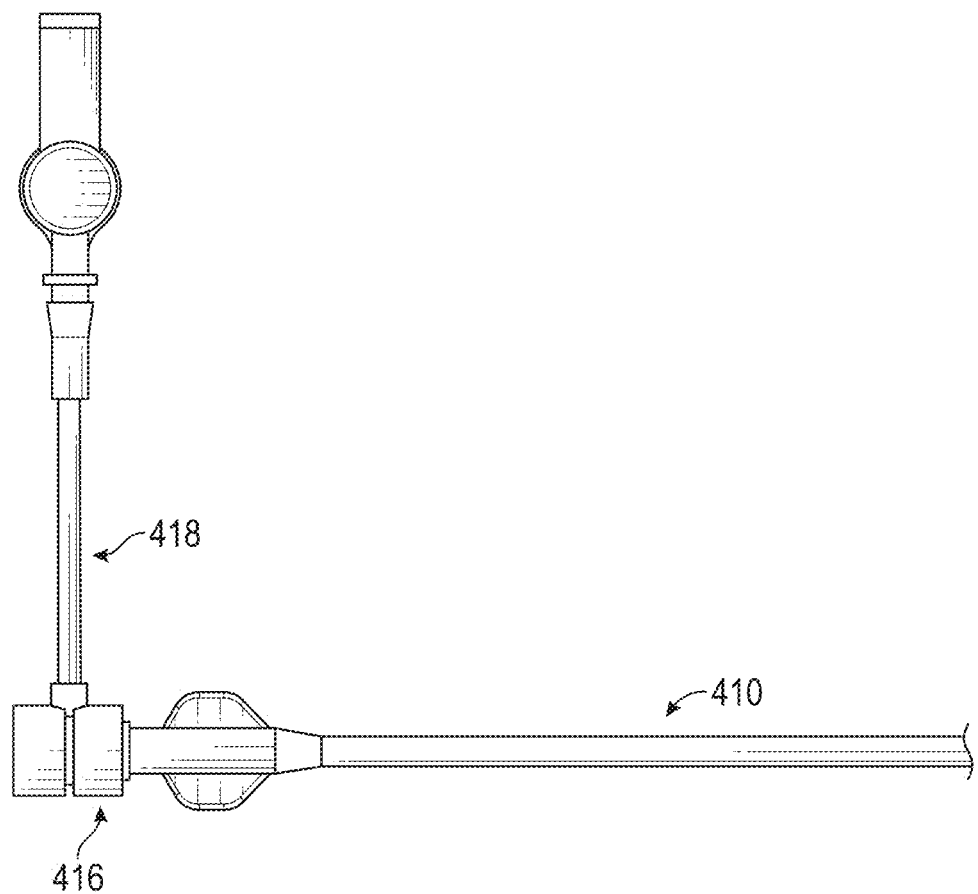
FIG. 22B is a side view of a proximal portion of the ventricular anchor delivery subsystem shown in FIG. 22A, in accordance with an embodiment.
Figure 22C:
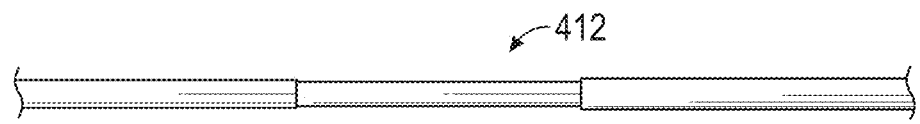
FIG. 22C is a side view of an intermediate portion of the ventricular anchor delivery subsystem shown in FIG. 22A, in accordance with an embodiment.
Figure 22D:
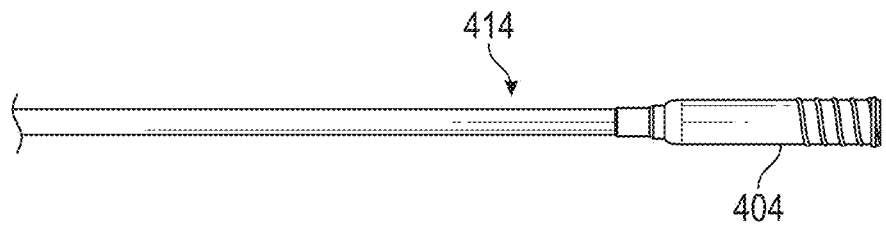
FIG. 22D is a side view of a distal portion of the ventricular anchor delivery subsystem shown in FIG. 22A, in accordance with an embodiment.
Figure 22E:
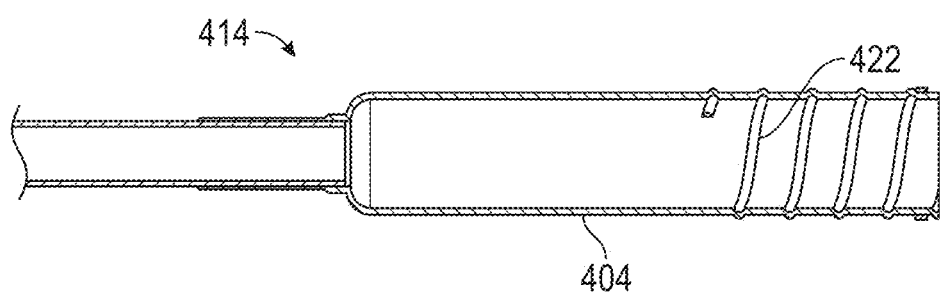
FIG. 22E is a longitudinal cross-sectional view taken through a portion of FIG. 22D, in accordance with an embodiment.

As seen in FIGS. 22D and 22E, a distal end of the collapsible sheath 404 can have an larger diameter than the intermediate portion 412. FIG. 22E is a longitudinal cross-sectional view of FIG. 22D. Threads 422 can be formed on the inner surface of the distal end of the collapsible sheath 404 to retain the anchor assembly 50 within collapsible sheath 404. Thus, in one arrangement, the coil 54 of the anchor assembly 50 can engage the threads 422 in the collapsible sheath 404 such that the anchor assembly 50 is retained within the sheath 404. Rotation of the anchor assembly 50 can drive the anchor assembly 50 forward through the sheath 404. In this manner, the sheath 404 can support the anchor assembly 50 during delivery such that the anchor assembly 50 will not be stripped out of the delivery sheath 404 during delivery. The distal larger diameter end of the sheath 404 is also collapsible to fit through the inner diameter of the delivery catheter 100 such that the collapsible anchor delivery sheath 404 can be withdrawn into the delivery catheter 100. In modified arrangements, the sheath 404 can include grooves, protrusions or other elements for engaging the anchor assembly 50.

In general, the sheath 404 may be provided with any of a variety of interference elements which releasably engage an implantable device such as a helical tissue anchor and resist axial pull out of the helical anchor once positioned within the sheath. Rotation of the anchor in a first direction relative to the sheath causes the anchor to move axially distally as the helix unthreads from the sheath. The interference element may be a helical (radially outwardly extending) channel or (radially inwardly extending) ridge, extending at least about one or two or four or more complete revolutions about the inner circumference of the sheath. In certain example embodiments, the interference element may be a helical (radially outwardly extending) channel or (radially inwardly extending) ridge, extending at least one or two or four or more complete revolutions about or around the inner circumference of the sheath.

Alternatively, at least about one or two or six or more radially inwardly extending tabs may be provided, each extending less than a full revolution around the circumference of the sheath. In certain example embodiments, at least one or two or six or more radially inwardly extending tabs may be provided, each extending less than a full revolution around the circumference of the sheath. Engagement tabs may have a length in the circumferential direction of no more than about 90 degrees, and in some implementations no more than about 45 degrees or 20 degrees or 10 degrees or less around the inside surface of the sheath. In certain example embodiments, engagement tabs may have a length in the circumferential direction of no more than 90 degrees, and in some implementations no more than 45 degrees or 20 degrees or 10 degrees or less around the inside surface of the sheath. Depending upon the desired performance, the implant can be disengaged from the catheter by a plurality of complete rotations, or by a rotation through, for example, less than a full rotation such as less than about a half or a quarter turn relative to the catheter. In certain example embodiments, depending upon the desired performance, the implant can be disengaged from the catheter by a plurality of complete rotations, or by a rotation through, for example, less than a full rotation such as less than a half or a quarter turn relative to the catheter.

Either the catheter side wall, the rotational anchor driver or both may be provided with torque transmission elements such as a spiral wound or braided side wall to facilitate rotation of the driver and inhibit rotation of the deployment catheter.

The sheath extends between a distal open end and a proximal end attached to the catheter shaft. The proximal end may have an angled engagement surface, for slidably engaging the distal opening on a delivery catheter so that the sheath is transformable from the radially enlarged configuration to the radially reduced configuration in response to proximal retraction into the delivery catheter.

The sheath may have an axial length that corresponds to the intended implant, generally less than about 15 cm and in many implementations no more than about 10 cm or 5 cm or 3 cm or less. In certain example embodiments, the sheath may have an axial length that corresponds to the intended implant, generally less than 15 cm and in many implementations no more than 10 cm or 5 cm or 3 cm or less.

The rotational interlock feature described above can be implemented on the inside surface of a flexible (collapsible) sidewall as described above, or on a fixed (non collapsible) sidewall catheter, in an embodiment where the OD of the device is smaller than the ID of the lumen in the deployment catheter. In a collapsible sheath implementation, the sheath may be collapsed following deployment of the device, by proximal retraction into the delivery catheter, which may have an ID which is smaller than the OD of the sheath when in the radially enlarged configuration for containing the implantable device.

FIG. 22F illustrates a method of forming the collapsible sheath 404. A mandrel 426 having a first diameter 430 and a second smaller diameter 432 can be provided. FIG. 22F is a longitudinal cross-sectional view of the mandrel similar to the cross-section view of FIG. 2E. The small diameter portion 432 of the mandrel 426 can be positioned within distal end of the intermediate portion 412. The mandrel 426 can include a transition zone 427 between the first and second portions 430 and 432 of the mandrel 426. A coil 450 can be positioned on an outer surface of the larger diameter portion 430 of the mandrel 426. A sheath 452 which will form the collapsible sheath 404 can be positioned over the mandrel 426 and the distal end of the tube intermediate portion 412. In an embodiment, the sheath 452 can comprise an approximately 0.005" wall thermoplastic elastomer (such as Pebax). The sheath 452 can be heat treated while on the mandrel 426 such that the proximal end of the sheath 452 is reduced in diameter and bonded to intermediate portion 412 and the distal end of the sheath 452 takes on the form of the coil 450 to form internal threads on the sheath 404. As noted above, the sheath 404 can include a radiopaque marker, such as a polymer radiopaque marker band made from, for example, a thermoplastic elastomer with 60% wt Tungsten that be incorporated with the sheath and thermally or otherwise suitably bonded to the sheath 404. In an embodiment, the marker is positioned on a distal end of the sheath.

Figure 22G:
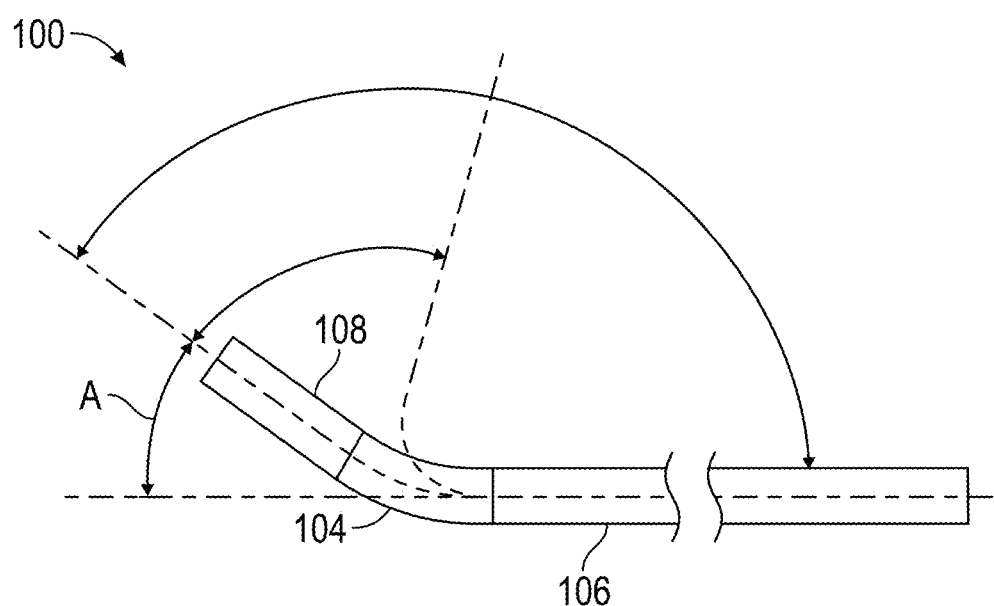
FIG. 22G is a side view of an embodiment of a distal end of delivery catheter articulated into a first bend, in accordance with an embodiment.

FIG. 22G illustrates a side view of a steering zone near a distal end of the delivery catheter 100 that can be articulated or bent in a first direction with respect to a central axis of the delivery catheter 100. The delivery catheter 100, as described herein, can be used to deliver a variety of subsystems. As such, the delivery catheter 100 can be configured to be positioned in the left atrium (such as shown in FIG. 3-6A) or the left ventricle (such as shown in FIG. 1). To achieve this position, the delivery catheter 100 can include a steering zone or first bend 102 such that the distal portion 108 of the catheter 100 is angled away from the proximal portion 106 of the catheter 100. In this manner, the steering zone of the delivery catheter 100 can be actively deflectable to form a delivery catheter curve that resides in a delivery catheter curve plane (also referred to herein as a first plane or X-Y plane). As shown in FIG. 22G, the delivery catheter 100 can bend in a range of angles. For example, the delivery catheter 100 can be articulated to include the first bend 102 such that the longitudinal central axis of a portion of the delivery catheter 100 distal to the bend forms an angle A with respect to a longitudinal central axis of a portion of the delivery catheter proximal to the bend 102. The angle A can be between 10 to 150 degrees and in certain embodiments the angle A can be between 30 and 80 degrees and in certain embodiments between 35 and 70 degrees. In some examples, the first bend 102 may be gradual such that the radius of curvature is at least 0.9 inches. In some examples, the first bend 102 can have a radius of curvature between 0.5 to 1.0 inches. The delivery catheter 100 can include various device and mechanisms for articulating the steering zone such as, for example, various combinations of pull wires that can be used to steer the catheter 100.

Figure 22H:
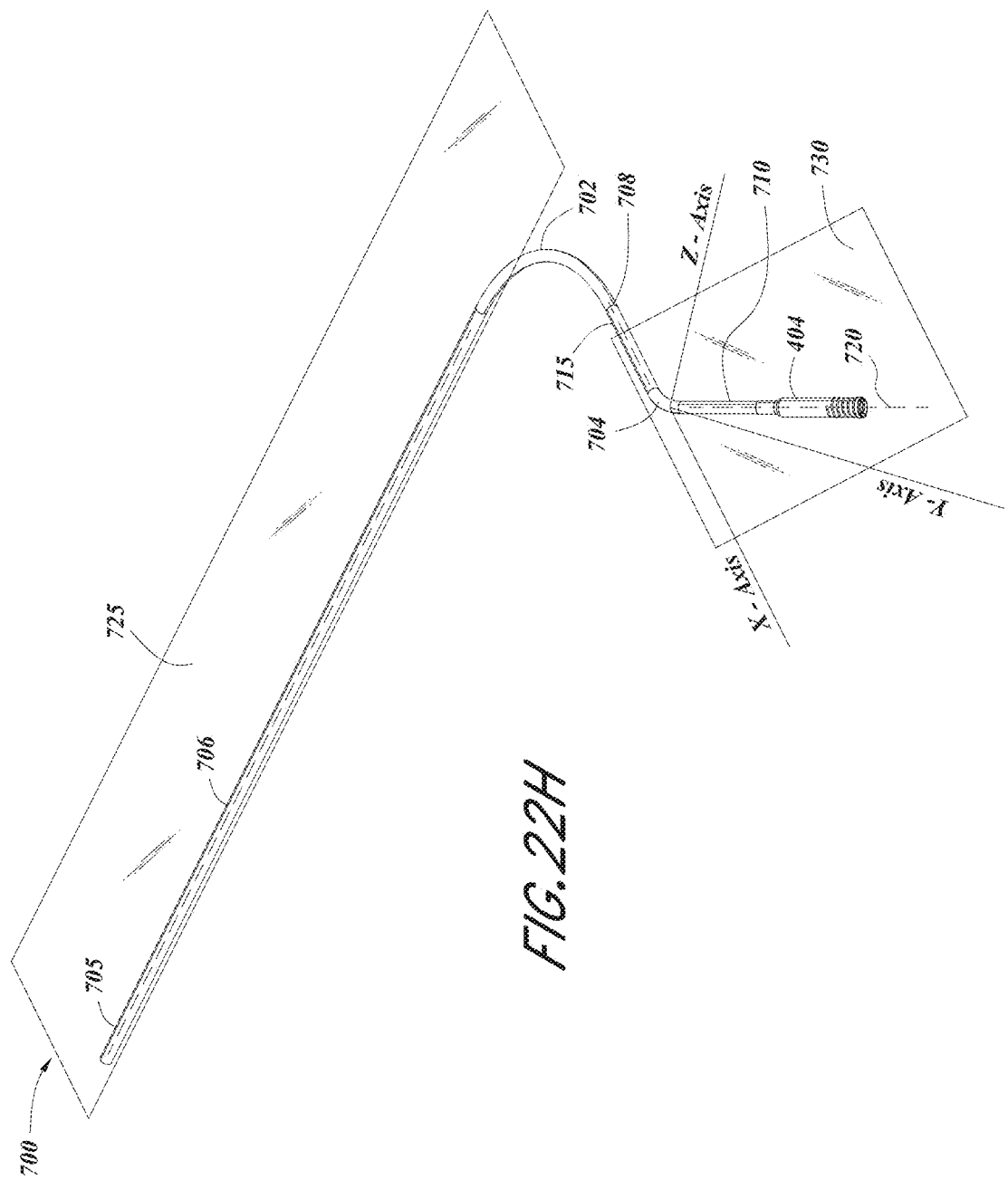
FIG. 22H is a perspective view of an embodiment of a ventricular anchor sheath preset with a first bend and a second bend, in accordance with an embodiment.

FIG. 22H is a perspective view of an embodiment of the ventricular anchor delivery sheath 700 that can include an elongate, flexible tubular body having a proximal end, a distal end, and a longitudinal axis. The ventricular anchor delivery sheath 700 can include a proximal preset curve 702 and a distal preset curve 704 and can be axially advanced through the delivery catheter 100. An access system can include the delivery catheter 100 and ventricular anchor sheath 700 for directing a ventricular anchor sheath at a target site in a left ventricle. The ventricular anchor sheath 700 can have a proximal portion 706, an intermediate portion 708 and a distal portion 710. As shown, the ventricular anchor sheath 700 can include a collapsible sheath 404 at the distal end of the distal portion 710 which can be configured as described above with the distal end of the collapsible sheath 404 forming a distal end of the ventricular anchor sheath 700. The collapsible sheath 404 can be a distal anchor compartment having a collapsible side wall. The proximal preset curve 702 can be positioned between the proximal portion 706 and the intermediate portion 708. The distal preset curve 704 can be positioned between the intermediate portion 708 and the distal portion 710. The ventricular anchor sheath 700 can be pre-formed or preset with the proximal preset curve 702 and the distal preset curve 704 such that the ventricular anchor sheath 700 takes on the form illustrated in FIG. 22H when it is unconstrained by an outer sheath such as the delivery sheath 100 discussed above. The proximal preset curve 702 can be proximal to the distal preset curve 704. The distal preset curve 704 can be distal to the proximal preset curve 702. In certain embodiments, the ventricular anchor sheath 700 is heat set into the shape shown in FIG. 22H to form the proximal and distal preset curves 702, 704 by placing the vertical anchor sheath 700 over a mandrel with the desired shape and then heat treating the sheath 700 to apply a pre-formed shape to the sheath 700. In some examples, the ventricular anchor sheath 700 can be shaped by applying heat and manually bending the ventricular anchor sheath 700 around a fixture to achieve the desired geometry. In other examples, the ventricular anchor sheath 700 can also be shaped by loading the ventricular anchor sheath 700 into a cassette with a preset geometry and applying heat to set the ventricular anchor sheath 700 in the desired geometry.

The proximal preset curve 702 of the ventricular anchor sheath 700 can be bent within the proximal preset curve plane (also referred to as the X-Y plane or first plane) to produce a range of angles B between a central longitudinal axis 705 of the proximal portion 706 and a central longitudinal axis 715 of the intermediate portion 708. For example, the angle B can be between 70 to 100 degrees and in certain embodiments can be between 85 and 95 degrees and in certain embodiments can be 90 degrees. In some examples, the proximal preset curve 702 may be gradual such that the radius of curvature is 2.0 inches. In some examples, the proximal preset curve 702 can have a radius of curvature between 0.5 to 3.0 inches. As will be explained below, the proximal preset curve 702 can help or orientate the ventricular sheath 700 within the delivery catheter 100. For example, the proximal preset curve 702 can have radius corresponding or similar to the radius of the first bend 102 of the delivery catheter 100. Accordingly as the ventricular sheath 700 is advanced through the delivery catheter 100, the proximal preset curve 702 causes the ventricular sheath 700 to take a specific rotational orientation within the delivery catheter 100 such that as a distal portion 710 of the ventricular sheath 700 exists the delivery catheter 100 it exists at a specific rotational orientation. Accordingly, the distal portion 710 of the ventricular sheath 700 can be pointed in a specific direction as it exists the delivery catheter 100. If the ventricle sheath 700 is not in the correct rotational orientation, the user can receive tactile feedback in the form of resistance to axial advancement of the sheath 700 through the delivery catheter 100. Rotation of the sheath 700 into the proper rotational orientation will reduce this resistance providing feedback to the use that the sheath 700 is correctly orientated. As shown in FIG. 22H, the proximal preset curve 702 can reside in the first plane 725 which can be referred to herein as a X-Y plane or the proximal preset curve plane 725.

As shown in FIG. 22H, the ventricular anchor sheath 700 can be bent so that portions of the sheath 700 can extend in two different planes. The proximal portion 706, proximal preset curve 702, and the intermediate portion 708 can be within the first plane 725, which can be referred as the X-Z plane or proximal preset curve plane as noted above. A y-axis can be perpendicular to the first plane 725 as shown in FIG. 22H. A central longitudinal axis 720 of the distal portion 710 can be within the second plane 730. The proximal preset curve 702 can angle the intermediate portion 708 away from the proximal portion 706 within the first plane 725 as described. The distal preset curve 704, in turn, can angle the distal portion 710 away from the intermediate portion 708 into the second plane 730 which can also be referred to as the distal preset curve plane or second plane. The distal preset curve 704 of the ventricular anchor sheath 700 can form an angle defined between the central longitudinal axis 715 of the intermediate portion 708 and the central longitudinal axis 720 of the distal portion 710. The angle between the central longitudinal axis 715 of the intermediate portion 708 and the central longitudinal axis 720 of the distal portion 710 can have two components: an angle α within the X-Z plane and shown in FIG. 22I and an angle β in the Z-Y plane shown in FIG. 22J such that that the distal portion 710 lies in a different plane than the intermediate 708 and proximal portion 710 of the sheath 800 and which is angled with respect to the X-Y plane. The intermediate portion 708 can have a length between 20 mm to 50 mm, such as approximately 32 mm, and the distal portion 710 can have a length between 20 mm to 50 mm, such as approximately 31 mm The length of the intermediate portion 708 can be used to control the ventricular implant location in the ventricle such that in certain embodiments the ventricular implant can be positioned at the base of the papillaries. The length of the distal portion 710 can be used to control distance from the centerline of the heart to the wall of the heart. As explained below, the intermediate portion 708 can center the distal portion 710 of the ventricle sheath over the mitral valve. The distal preset curve 704 can direct the distal portion 710 of the sheath 700 from above the mitral valve to a position through the mitral valve and towards the ventricle such that a ventricular anchor as described above can be placed.

In the illustrated embodiment, the distance between the distal end of the ventricular anchor sheath 700 and a longitudinal center or mid-point of the distal preset curve 704 can be within the range of 30 to 90 millimeters in an embodiment and within the range of 50 to 70 millimeters in another embodiment and about 60 millimeters in another embodiment. In certain example embodiments, the distance between the distal end of the ventricular anchor sheath 700 and a longitudinal center or mid-point of the distal preset curve 704 can be within the range of 30 to 90 millimeters in an embodiment and within the range of 50 to 70 millimeters in another embodiment and 60 millimeters in another embodiment. In the illustrated embodiment, the distance between the distal end of the ventricular anchor sheath 700 and a longitudinal center or mid-point of the proximal preset curve 702 can be within the range of 80 to 165 millimeters in an embodiment and within the range of 100 to 145 millimeters in another embodiment and about 125 millimeters in another embodiment. In certain example embodiments, the distance between the distal end of the ventricular anchor sheath 700 and a longitudinal center or mid-point of the proximal preset curve 702 can be within the range of 80 to 165 millimeters in an embodiment and within the range of 100 to 145 millimeters in another embodiment and 125 millimeters in another embodiment. In the illustrated embodiment, the distance a longitudinal center or mid-point of the distal preset curve 704 and a longitudinal center or mid-point of the proximal preset curve 702 can be within the range of 45 to 85 millimeters in an embodiment and within the range of 25 to 105 millimeters in another embodiment and about 65 millimeters in another embodiment. In certain example embodiments, the distance a longitudinal center or mid-point of the distal preset curve 704 and a longitudinal center or mid-point of the proximal preset curve 702 can be within the range of 45 to 85 millimeters in an embodiment and within the range of 25 to 105 millimeters in another embodiment and 65 millimeters in another embodiment.

Figure 22I:
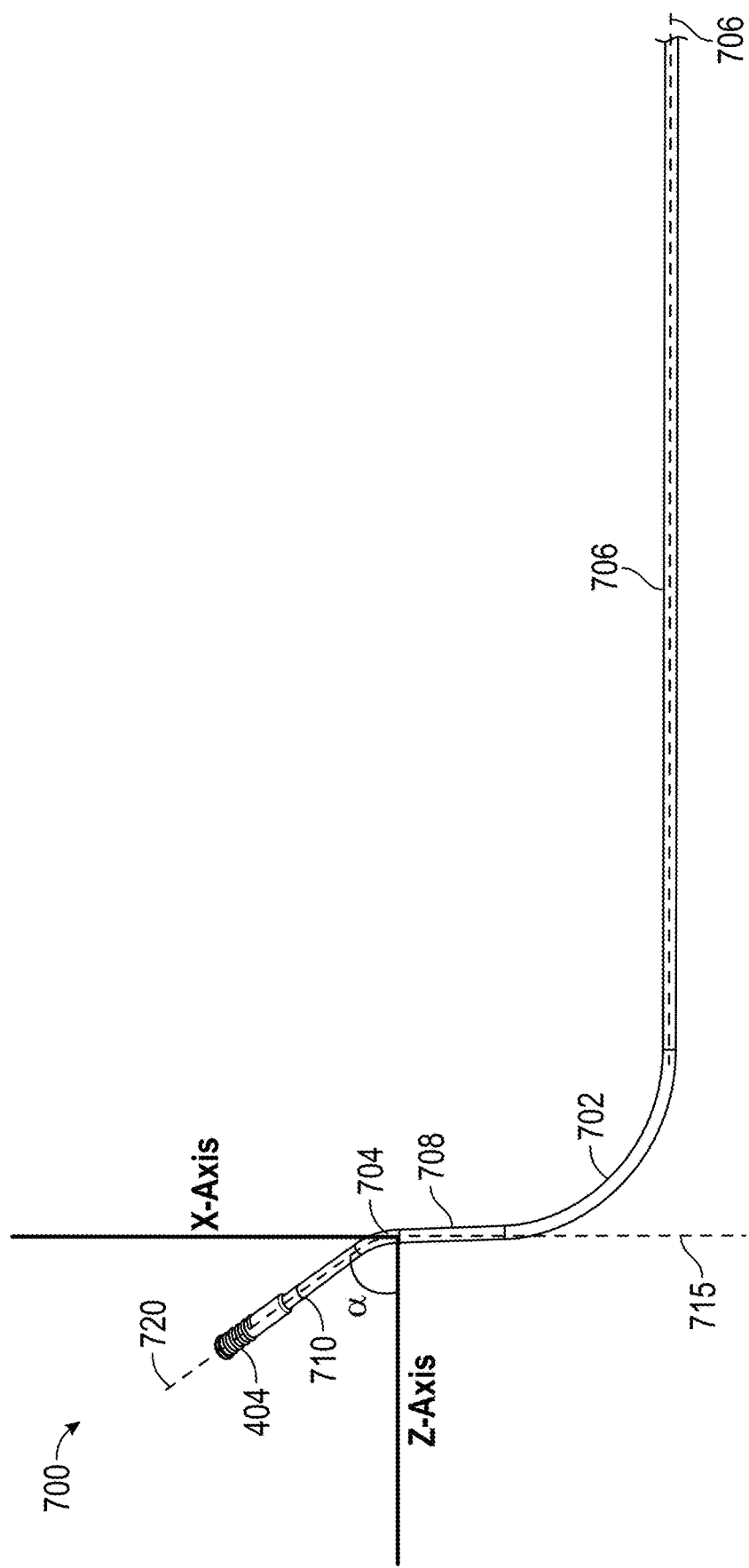
FIG. 22I is a top view of the ventricular anchor sheath of FIG. 22H, in accordance with an embodiment.

FIG. 22I is a top view of the ventricular anchor sheath 700 of FIGS. 22H-I to illustrate the angle, a in the X-Z plane. As shown in FIG. 22I, the distal portion 710 can incline at an angle, a, within a range of 5 degrees to 60 degrees with respect to the central longitudinal axis of the intermediate portion 708 in the X-Z plane. For example, the angle α of the distal preset curve 704 can be approximately 45 degrees in the with respect to the central longitudinal axis of the intermediate portion 708 in the X-Z plane.

Figure 22J:
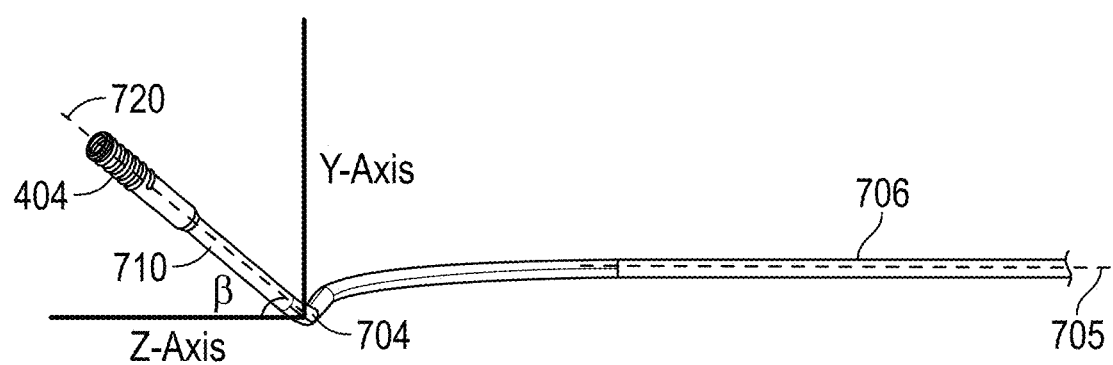
FIG. 22J is a side view of the ventricular anchor sheath of FIGS. 22H-I, in accordance with an embodiment.

FIG. 22J is a side view of the ventricular anchor sheath 700 of FIGS. 22H-I. As shown in FIG. 22J, the central longitudinal axis 720 of the distal portion 710 can be inclined at the angle, β with respect to the central longitudinal axis 705 of the proximal portion 706 or the Z-axis in the X-Z plane described above and the angle β can be within a range of 40 to 75 degrees. For example, the angle β formed by the distal preset curve 704 can be approximately 40 to 75 degrees in the y direction measured from the z-axis, which can be substantially parallel to the central longitudinal axis 705 of the proximal portion 706. In certain embodiments, the angle β can be 60 degrees. Accordingly, in the illustrated embodiment distal preset curve 704 can reside in a second plane also referred to herein as a distal preset curve plane that rotationally offset from the first plane (i.e. the X-Z plane or proximal preset curve plane) by an angle within the range of from 40 to 75 degrees and in certain embodiments 60 degrees.

Figure 22K:
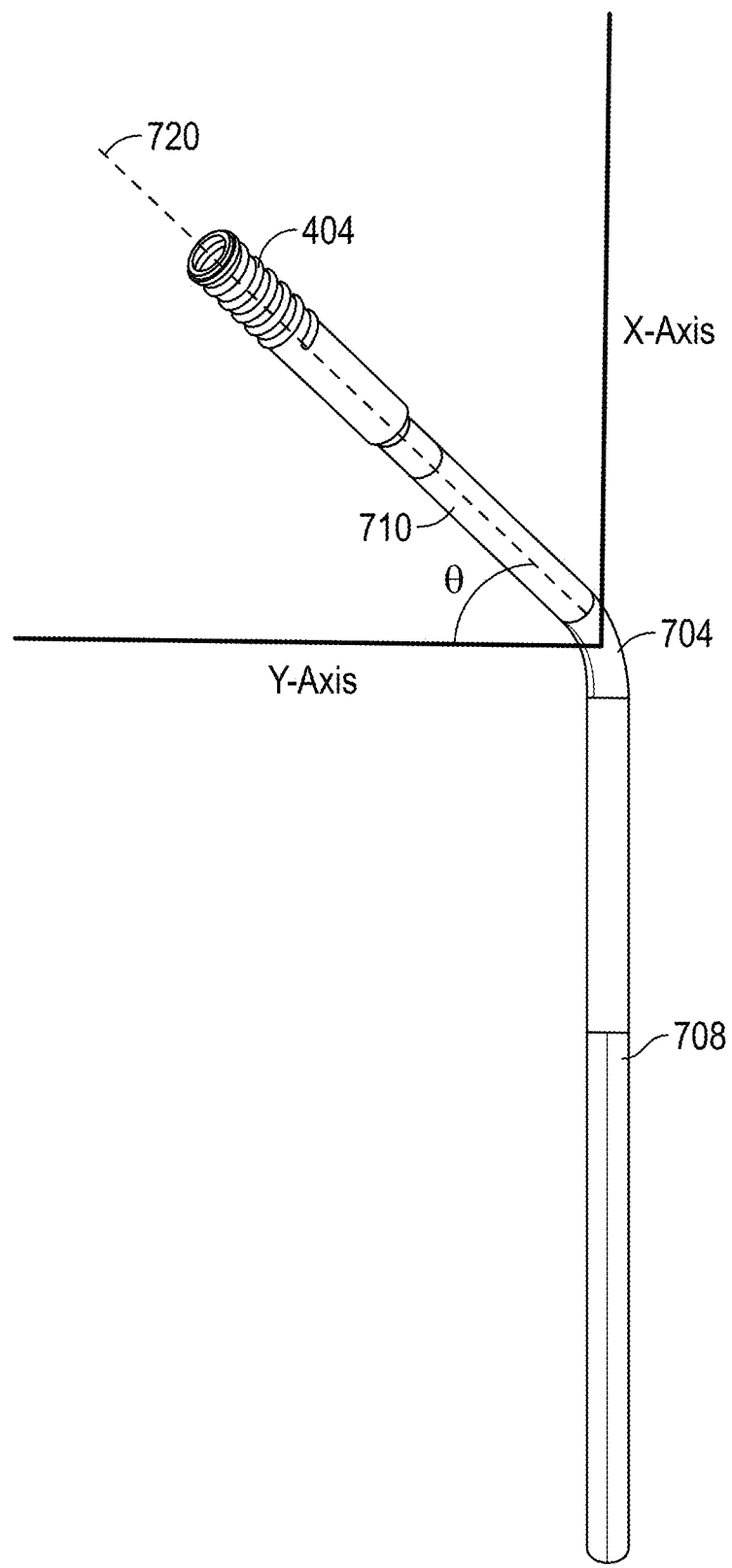
FIG. 22K is a front view of the ventricular anchor sheath of FIGS. 22H-J, in accordance with an embodiment.

FIG. 22K is a front view of the ventricular anchor sheath 700 of FIGS. 22H-J. As shown in FIG. 22K, the distal portion 710 can incline at an angle, θ, in the x direction measured from the y-axis. For example, the angle θ of the distal preset curve 704 can be approximately 30 to 60 degrees and in some embodiments 45 degrees in the x direction measured from the y-axis, which can be substantially perpendicular to the longitudinal axis 705 of the proximal portion 706.

In some examples, the distal preset curve 704 may be sharper than the proximal preset curve 702. For example, the distal preset curve 704 can have a radius of curvature of 0.45 inches. In some examples, the distal preset curve 704 can have a radius of curvature between 0.1 to 0.5 inches. In certain embodiments, an arc length of the distal preset curve is no more than about 50% of the arc length of the proximal preset curve and in certain embodiments, the arc length of the distal preset curve is no more than about 20% of the arc length of the proximal preset curve. In certain example embodiments, an arc length of the distal preset curve is no more than 50% of the arc length of the proximal preset curve and in certain embodiments, the arc length of the distal preset curve is no more than 20% of the arc length of the proximal preset curve.

Figure 22L:
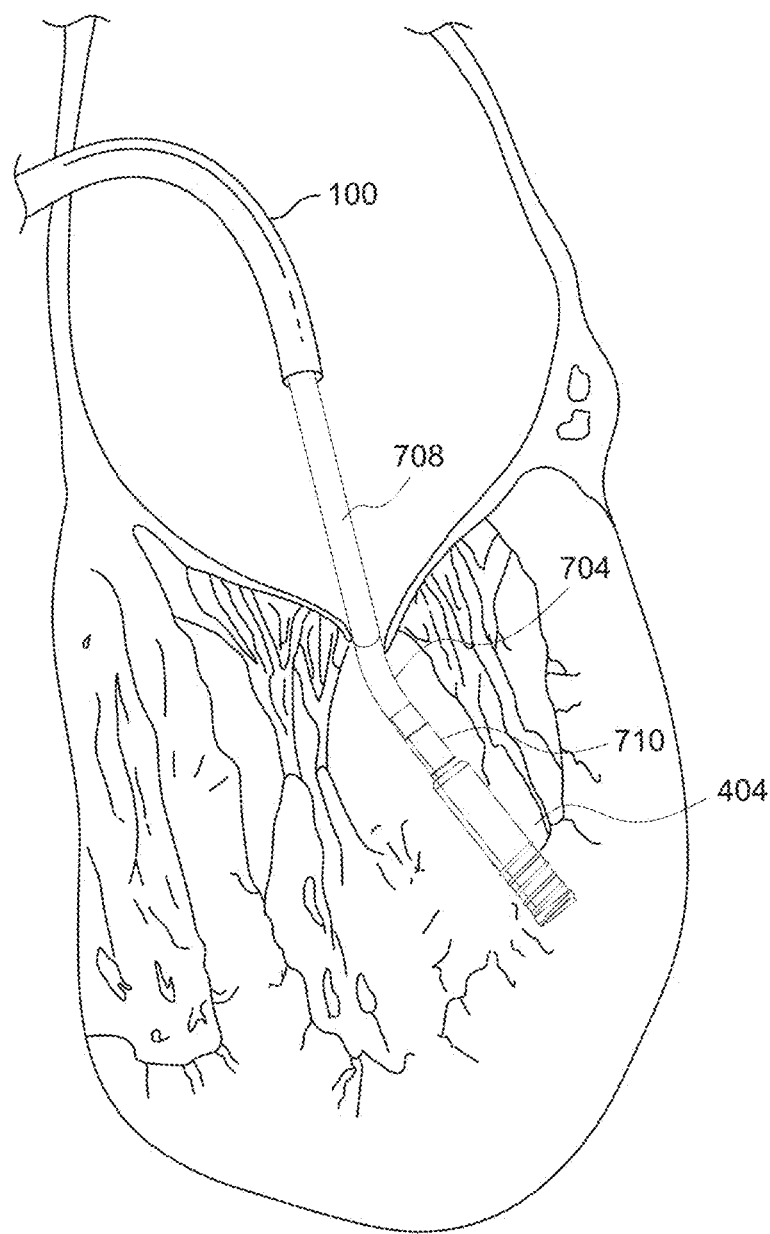
FIG. 22L illustrates placement of a ventricular anchor with the ventricular anchor sheath of FIGS. 22H-K and delivery catheter of FIG. 22G, in accordance with an embodiment.

FIG. 22L illustrates placement of a ventricular anchor 302 with the ventricular anchor sheath 700 of FIGS. 22H-K and the delivery sheath of FIG. 22G. The ventricular anchor sheath 700 can be used in the methods and steps described above (such as with the drive shaft 307, driver head 306 and other components described above for rotating and delivering the anchor assembly 50). For example, the ventricular anchor delivery sheath 700 can be inserted and pass through the catheter 100. The ventricular anchor delivery sheath 700 can deliver a ventricular anchor, such as a helical anchor 32.

The ventricular anchor sheath 700 can be advanced through the delivery catheter 100. When the ventricular anchor sheath 700 is fully inserted within the delivery catheter 100 such that the intermediate portion 708 and distal portion 710 are advanced out of the delivery catheter 100, the proximal preset curve 702 of the ventricular anchor sheath 700 can be aligned with the first bend 102 and delivery catheter curve of the delivery catheter 100. The proximal portion 106 of the delivery catheter 100 can be aligned with the proximal portion 706 of the ventricular anchor sheath 700. The intermediate portion 708 and the distal portion 710 of the ventricular anchor sheath 700 can extend beyond the distal portion 106 of the delivery catheter 100 as shown in FIG. 22L. The alignment of the first bend 102 of the delivery catheter 100 and the proximal preset curve 702 of the ventricular anchor sheath 700 can insure that the distal portion 710 of the ventricular anchor sheath 700 is oriented correctly when it exits the delivery catheter 100. For example, the delivery catheter 100 can have a first bend 102 in a delivery catheter curve to position and orient the distal portion 108 within the ventricular atrium. The ventricular anchor sheath 700 can be positioned within the delivery catheter 100 such that distal portion 710 of the ventricular anchor sheath 700 extends from the distal end of the delivery catheter 100 and is positioned in the left ventricle. The anchor sheath 700 is configured to rotate within the delivery catheter 100 to bias the proximal preset curve plane into alignment with the delivery catheter curve plane in response to axial alignment of the anchor sheath proximal preset curve within the delivery catheter curve. In certain embodiments, the proximal preset curve 702 and the delivery catheter curve 102 are configured to cooperate to provide tactile indicium of the rotational alignment of the anchor sheath 700 within the delivery catheter 100.

The ventricular anchor sheath 700 can be positioned such that the proximal preset curve 702 orients the intermediate portion 708 partially in the left atrium and across the valve and the distal preset curve 704 orients the distal portion 710 in the left ventricle. The delivery catheter 100 would be positioned in the left atrium, such as shown in FIGS. 11 and 12 and FIG. 22L. The ventricular anchor sheath 700 can be positioned within the delivery catheter 100 such that the first bend 102 of the delivery catheter 100 is aligned with the proximal preset curve 702 of the ventricular anchor sheath 700. The ventricular anchor, such as ventricular anchor 32, can then be inserted through the ventricular anchor sheath 700 for delivery. For example, the ventricular anchor 302 can be delivered to into heart tissue, e.g., near the apex of the left ventricle or near a papillary muscle.

The proximal preset curve 702 and the distal preset curve 704 of the ventricular anchor sheath 700 can be preset. As noted above, in some examples, the ventricular anchor sheath 700 can be made with a curved mandrel to heat set the angles of the bends of the ventricular anchor sheath 700. The ventricular anchor sheath 700 can be substantially flexible and bendable such that when the ventricular anchor sheath 700 is being inserted into the delivery catheter 100, the ventricular anchor sheath 700 can be substantially aligned with the delivery catheter 100. For example, if the delivery catheter 100 was substantially straight, the ventricular anchor sheath 700 can be substantially straight when positioned within the delivery catheter 100. When the distal preset curve 704 and the distal portion 710 is exposed and not constrained within the delivery catheter 100, the preset curve of the proximal preset curve 702 is aligned with the bend 102 of the delivery catheter 100 would orient the proximal preset curve 704 and the preset curve of the second bend 704 would orient the distal portion 710 in the desired orientation within the heart. The ventricular anchor sheath 700 can include a distal marker near the second bend 704 to indicate how far the inner ventricular anchor sheath 700 to be extended beyond the delivery catheter 100. An advantage of the two preset curves (proximal and distal) in the anchor catheter sheath 700 described herein is such that when the delivery catheter 100 is positioned centrally above the mitral valve in the atrium, simply advancing the anchor catheter sheath 700 distally from the end of the delivery catheter 100 will direct the tip of the anchor catheter sheath 700 to a target location, which can be between the base of the papillary muscles on the posterior left ventricle wall without any additional catheter manipulation.

As noted above, the above described embodiment with preset proximal and distal curves 702 and 704 can advantageously direct the distal end of the anchor sheath to a desired location for the anchor as the anchor sheath exits the delivery catheter. In a modified embodiment, the anchor sheath 700 can be steerable through the use of pull wires or other mechanisms for steering a catheter. In such embodiments, the steerable anchor sheath 700 can be configured to have proximal and distal steering zones that can be configured at the locations described above and can articulate through the angles described above for the preset proximal and distal curves 702, 704. In another embodiment, a present mandrel can be provided with preset proximal and distal curves 702, 704 arranged as described above. The preset mandrel can then be inserted through anchor sheath so that the anchor sheath takes on the shape of the preset mandrel.

Rotational Suture Cutter

FIGS. 23A-C, 24A-D, 25A-B and 26 illustrate another embodiment of a cutter catheter 500 that can be used to cut sutures 74, 344 in one more of the procedures and systems described above. For example, once the sutures 74, 344 are locked (fixedly secured) within the suture lock 376, the proximal ends of the sutures 74, 344 may be cut adjacent to the proximal face of the suture lock 376 with an embodiment of the suture cutter catheter 500 described herein.

Figure 23C:
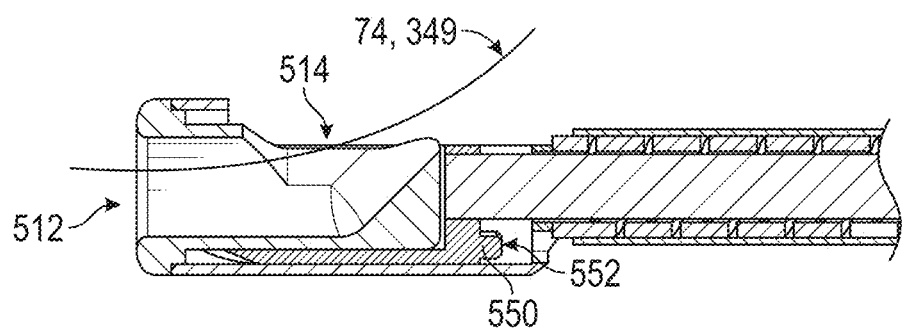
FIG. 23C is a cross-sectional view taken along line 23C-23C of FIG. 23A, in accordance with an embodiment.
Figure 24C:
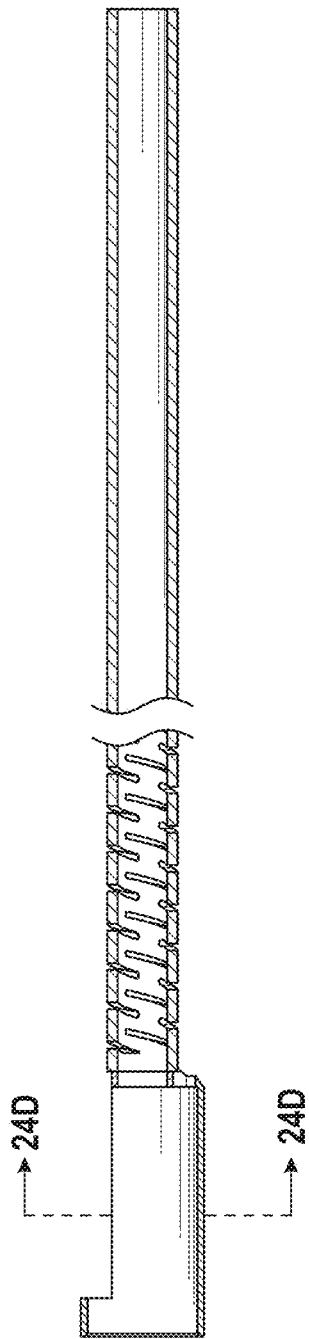
FIG. 24C is a cross-sectional side view of the cutter housing of FIG. 23B, in accordance with an embodiment.
Figure 24D:
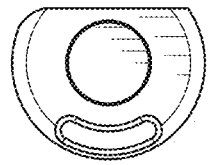
FIG. 24D is a view of the cutter housing taken from line 24D-24D of FIG. 24C, in accordance with an embodiment.

With initial reference to FIGS. 23A and 23B, the cutter catheter (also referred to as a endovascular suture cutter) 500 can include an outer sheath 504 extending through the delivery catheter 502 and an inner shaft 506 extending through the outer sheath 504. A proximal end of the outer sheath 504 can be coupled to a luer lock 503. With reference to FIG. 24, the outer sheath 504 is coupled to a cutter housing 510 at the distal end of the outer sheath 504. The cutter housing 510 can be in the shape of a barrel that forms cylindrical chamber. The distal end of the cutter housing 510 can have opening 512 through which sutures can extend from the opening 512 and then through a window 514 formed on a side of the cutter housing 510 to define a suture path extending through the cutter housing 510. In this manner, sutures 74, 344 can be advanced through the cutter housing 510 as shown in FIG. 23C.

Figure 26:
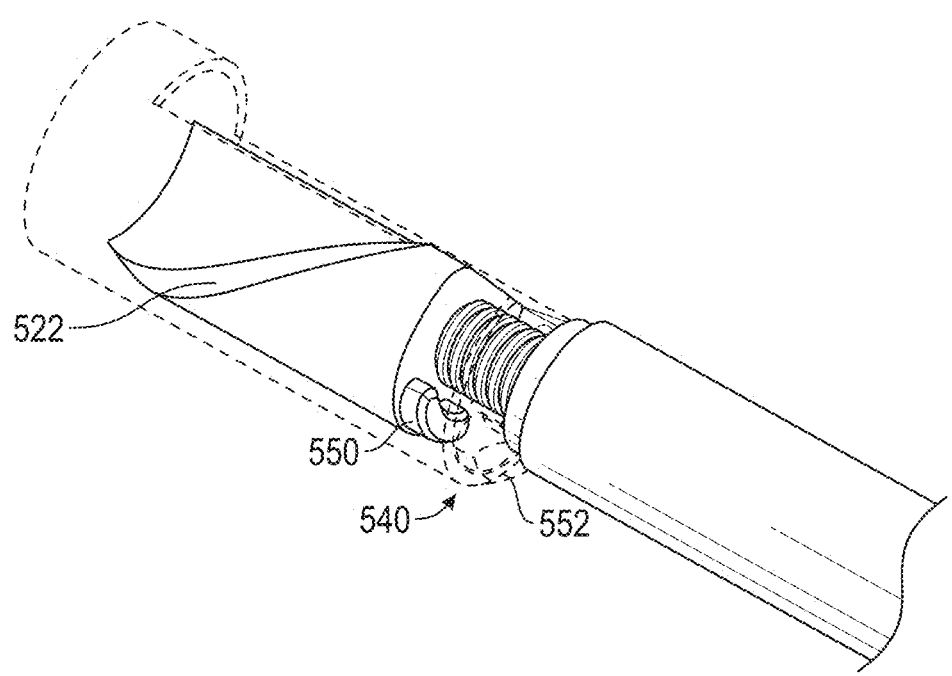
FIG. 26 is perspective side view of the cutter head positioned with the cutter housing with the cutter housing shown in phantom, in accordance with an embodiment.

With reference to FIGS. 25A, 25B and 26, a cutter head 520 can be rotationally positioned within the cutter housing 510. The cutter head 520 can have a hollow half-barrel or partial barrel shape that includes a cutting edge 522. The cutting edge 522 can have a helical path or curved shape as the edge 522 extends from the distal end to the proximal end of the cutter head 520. The cutting edge 522 can extend along a side surface of the cutter head 520 as shown in FIG. 26. Sutures extending through the distal opening 512 and the side window 514 can be cut by rotating the cutter head 520 within the cutter housing 510. Rotation will cause the sutures to be compressed between the cutting edge 522 and the inside surface of the cutter housing 510. Because of the profile of the cutting edge 522, the sutures can be sliced which can produce a more efficient and reliable cutting motion as compared to compressing or chopping motions.

Advantageously, when the endovascular suture cutter 500 is advanced into the heart the cutting edge 522 of the cutter head 520 is not exposed and covered by the surfaces of cutter housing 510. For example, as shown in FIG. 26, the cutting edge 522 is covered by the inside surfaces of the cutter housing 510. In the illustrated embodiment, the cutter catheter 500 also includes a lock 540 at the distal end of the endovascular suture cutter 500 to prevent rotation between the cutter head 520 and the cutter housing 510. In the illustrated embodiment, the lock 540 can comprise a protrusion 550 on the cutter head 520 that engages a corresponding recess 552 in the cutter housing 510. When engaged, the protrusion 550 and the recess 552 prevent rotation between the cutter head 520 and the cutter housing 510. In this manner, the cutting edges 522 can remain in a position in which they are not exposed and are covered by the inner surfaces of the cutter housing 510. The protrusion 520 and the recess 522 can be disengaged by axially advancing the rotational housing 520 with respect to the cutter housing 510. In the disengaged positon, the cutter head 520 can be rotated with respect to the cutter housing 510 to cut sutures as described above. The protrusion 520 and the recess 522 can be reversed in other arrangements and/or positioned on other portions of the cutter housing 510 and cutter head 520.

Figure 27:
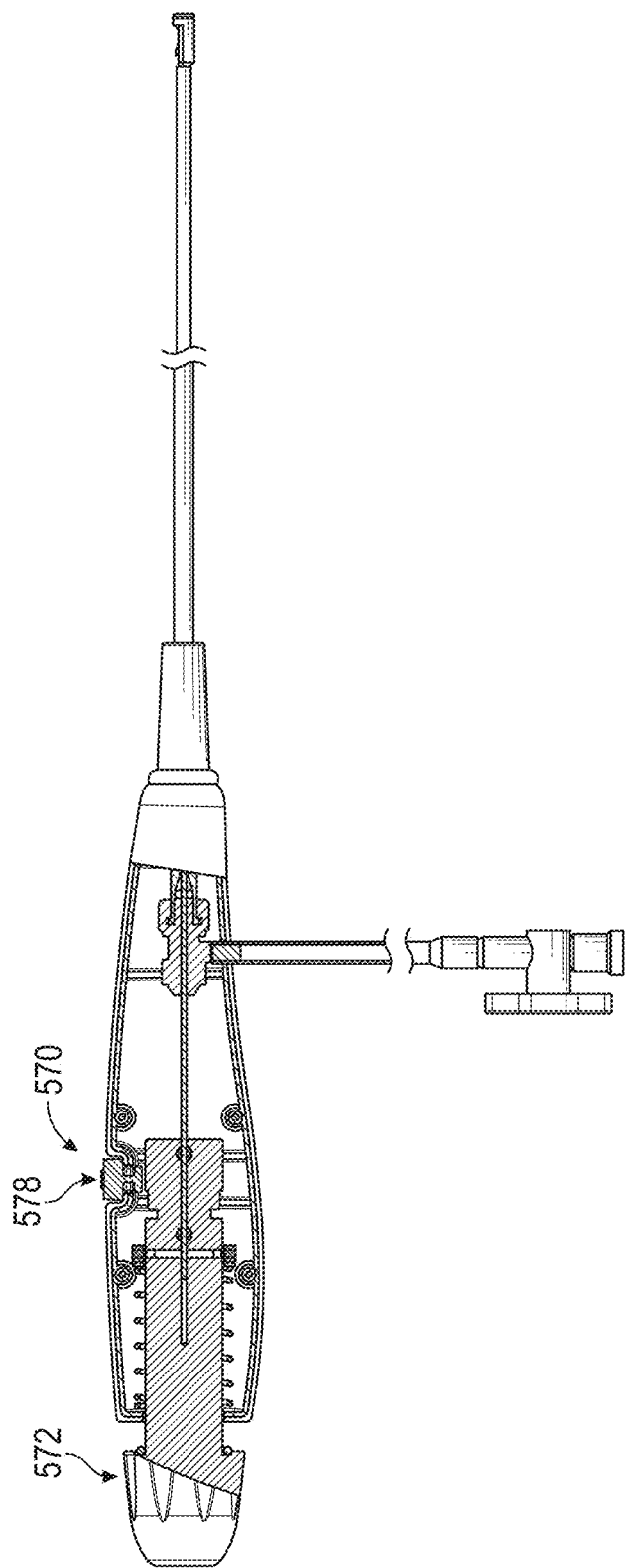
FIG. 27 is a cross-sectional side view of a handle of an embodiment of the cutter catheter, in accordance with an embodiment.

FIG. 27 illustrates a proximal handle 570 which can be formed around the luer lock 503. The handle 570 can be used to control the movement of the cutter head 520 and cutter housing 510. In this arrangement, the cutter head 510 can be fixed with respect to a handle 570. The cutter head 520 can be rotationally linked and coupled to a suture cutter handle 572 such that rotation of the suture cutter handle 572 will cause the cutter head 520 to rotate with respect to the cutter housing 510. As shown, the suture cutter handle 572 is positioned in retracted position with respect to the handle 570 in which the protrusion 550 and the recess 552 would be engaged to prevent rotation between the cutter head 520 and the cutter housing 510. A lock 578 can be provided on the handle 570. Releasing the lock 578, allows the cutter head handle 572 to move axially (e.g., distally in the illustrated embodiment) with respect to the handle 570. In this manner, the protrusion 550 and the recess 552 can be disengaged and the suture cutter handle 572 can be rotated with respect to the handle 570 to cut sutures.

Pledget with Radiopaque Marker

Figure 28:
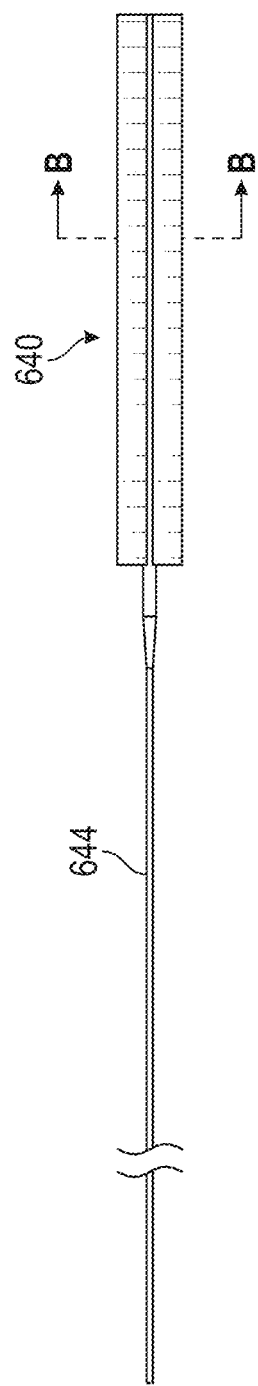
FIG. 28 is a top view of an embodiment of a suture and pledget that can form an embodiment of a leaflet anchor, in accordance with an embodiment.
Figure 29:
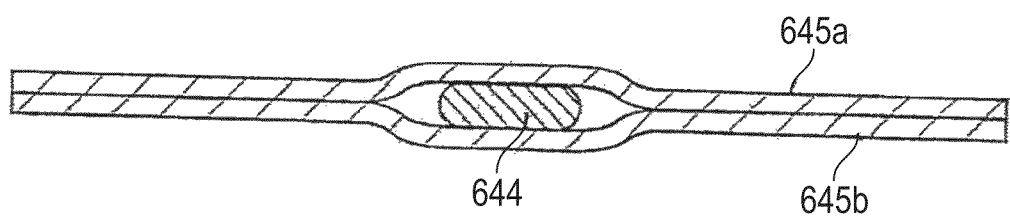
FIG. 29 is a cross-sectional view taken through line B-B of FIG. 28, in accordance with an embodiment.
Figure 30:
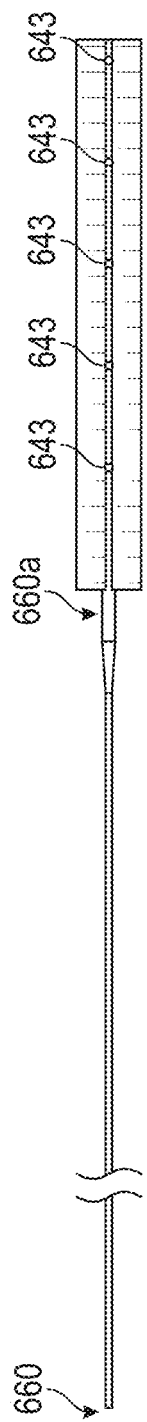
FIG. 30 is a top view of an embodiment of a suture and pledget with apertures that can form an embodiment of a leaflet anchor, in accordance with an embodiment.

FIGS. 28-31 illustrate an embodiment of a leaflet anchor 641 that can include a pledget 640 and can be use used with and in the systems and methods described herein. FIGS. 28 and 29 schematically depict an embodiment the pledget 640 that formed by affixing a distal end a suture 644 between two flat sheets 645a, 645b. FIG. 29 shows a cross-section of the pledget 640 along the axis of B-B illustrated in FIG. 28. In some embodiments, the suture 644 may be inserted between the two sheets 645a, 645b (e.g., substantially down the middle of the sheets) and pressed and/or laminated to join the three components together (e.g., under heat and/or pressure). At least one of the layers may be partially sintered. The suture 644 may be flattened and/or densified to improve resistance to suture tear out. The sheets may be flat polytetrafluoroethylene (PTFE) sheets (e.g., thin uncured expanded PTFE (ePTFE) sheets) or any other suitable material. In some implementations, the leaflet suture 644 may be disposed between the sheets in alternative configurations, such as a zig-zag or s-shaped configuration. FIG. 30 shows the pledget 640 of FIG. 28 comprising a plurality of apertures 643 through which a proximal tail end 660 of the suture 644 may be threaded through. In some embodiments, one or more apertures 643 may be formed through the pledget, in various configurations, to form a collapsible structure, as described elsewhere herein, which is configured to anchor the suture 644 against the mitral leaflet. FIG. 30 shows apertures 643 extending through the center of the pledget through the suture 644. In some embodiments, the apertures 643 can be alternating around opposing sides of the suture 644. In some embodiments, the apertures 643 may be formed on the same side of the suture 644 (e.g., in wing 641 or wing 642). In the illustrated arrangement, the apertures 643 can be formed through the suture 644. The apertures 643 can be aligned along a center of the pledget 640. The apertures 643 may be aligned along the length of the suture 644 (e.g., may form a straight line). The apertures 643 can extend from a first or proximal end to a distal or second end of the pledget 640. The suture 644 may be at least partially flattened between the two opposing sheets, which may facilitate the placement of apertures 643 through the suture 644. Various combinations of apertures 643, including the positioning described above, may be used.

Figure 31:
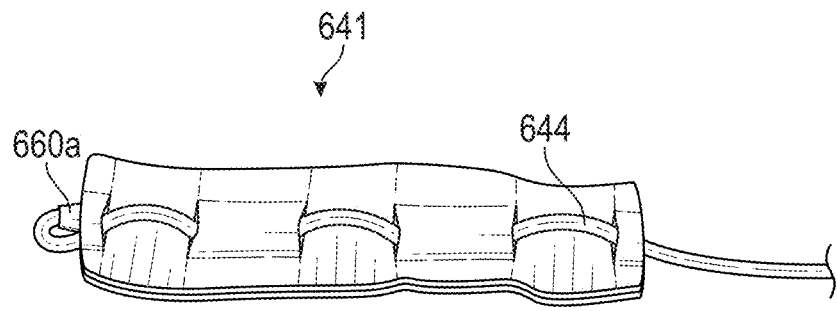
FIG. 31 illustrates an embodiment of the leaflet anchor of FIG. 30 with the suture extending through the apertures, in accordance with an embodiment.

A radiopaque marker may be added to the pledget 640. For example, in the illustrated embodiment of FIGS. 28-31, a marker band 660a can be positioned about or around the suture adjacent the second or distal end of the pledget 640. The marker band 660a can be crimped to the suture 644 in this position. The proximal end 660 of the suture 644 can then be threaded through the apertures 643 formed in the pledget 640 starting with an aperture 643 closest to the marker band 660a as shown in FIG. 31 thereby positioning the marker band 660a at the distal end of the pledget 640 when deployed. The pledget 640 may be transformable from an elongate strip configuration to a radially enlarged, axially shortened configuration by proximal retraction of the suture 644.

Flexible Pledget Delivery Needle

As noted above, in certain embodiments, a radially enlargeable leaflet anchor may be carried within a hollow needle having a sharpened end for piercing the leaflet. The radially enlargeable leaflet anchor may comprise a pledget. The pledget may be transformable from an elongate strip configuration to a radially enlarged, axially shortened configuration by proximal retraction of the suture.

Figure 32:
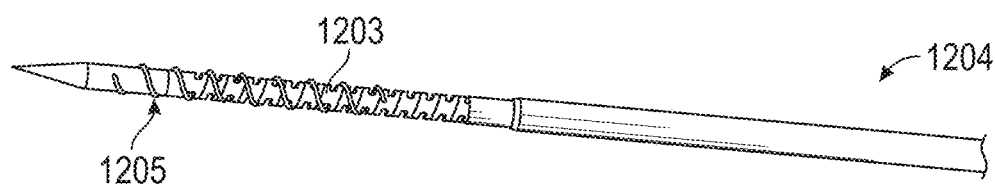
FIG. 32 is a side perspective view of needle according to certain aspects of the disclosure, in accordance with an embodiment.

In some embodiments, the hollow needle comprises an exterior surface having one or more helical grooves. In other embodiments, the hollow needle may comprise one or more raised helical coils, for example, a thin coil that is attached to the exterior of the hollow needle. FIG. 32 shows an embodiment wherein the hollow needle 1204 has a helical coil 1205 attached to an outer surface of the needle 1204. Since the leaflet may be in motion before, during and after the puncture process, the leaflet may have enough range of motion that a hollow needle without grooves or the raised helical coil may slip off of the leaflet. The grooved surface or raised helical coil can present several benefits. First, in the event that the hollow needle does not completely puncture the leaflet, i.e., the distal portion of the hollow needle does not allow delivery of the pledget or if the physician determines that the hollow needle may prematurely slip off of the leaflet during the procedure, the physician can provide a force onto the catheter or a mechanism within the catheter that transfers a rotational force to the needle, thereby screwing the hollow needle in further to the leaflet tissue and securing leaflet so that it does not move off of the needle. Secondly, once the pledget has been delivered, the physician can provide a force to the catheter or a mechanism within the catheter that transfers a rotation force to the hollow needle, thereby allowing the physician to remove the needle by unscrewing the hollow needle from the leaflet.

According to the catheter system used, the hollow needle can be directed to puncture the needle from the left atrial side of the heart to the left ventricular side. In other embodiments, the hollow needle can be directed to puncture the leaflet from the left ventricular side of the heart to the left atrial side. Since the entry points from the exterior of the patient to the heart can vary, it can be desirable that at least a portion of the hollow needle is flexible. Utilizing a flexible hollow needle can allow the hollow needle to travel around all of the curvature in order to access the leaflet and can allow the physician the ability to fine tune placement of the needle prior to puncturing the leaflet. FIG. 32 shows cut portions 1203 of the hollow needle which allow the hollow needle to flex as needed. In some embodiments, the cut portions 1203, of the hollow needle can be laser cut, can be machined, or other known methods can be used.

Figure 33:
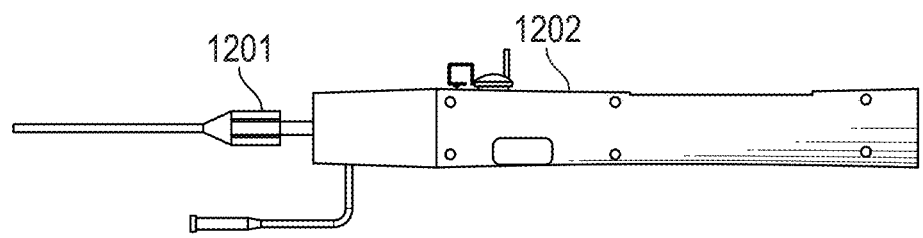
FIG. 33 is a perspective view of a pledget delivery handle according to certain aspects of the disclosure, in accordance with an embodiment.

The system can also comprise a hollow needle wherein the hollow needle punctures the leaflet via the release of a stored energy source. For example, the stored energy can be in the form of a spring, a liquid under pressure, a gas under pressure, an electrically activated piston or other known method. In some embodiments, the stored energy device is a spring. In still further embodiments, the spring is located in the pledget delivery handle 1202, shown in FIG. 33.

The amount of stored energy should provide enough force to the hollow needle in order to puncture the leaflet a sufficient distance or depth. As used herein, "sufficient distance or depth" can mean one or more of the following: wherein the distal end of the hollow needle completely punctures the leaflet without causing the hollow needle to contact or puncture any other structures within the heart; allows the needle to stay engaged with the leaflet while the leaflet is moving; and allows the physician to deliver the pledget. If the needle did not puncture through the leaflet a sufficient distance or depth, the physician can rotate the hollow needle in order to drive the hollow needle further through the leaflet tissue. If the needle did not puncture the leaflet in the correct location, the physician can rotate the hollow needle in an opposite direction thereby removing the hollow needle from the leaflet tissue. The system can then be re-armed, that is, re-energized with the stored energy, repositioned and actuated in order to properly place the hollow needle for delivery of the pledget. In some embodiments, the system comprises a control device wherein the physician is able to position the catheter (containing the retracted hollow needle) on or near the leaflet, check the positioning of the catheter relative to the leaflet to be sure that the catheter is in the correct location and actuate the release of the stored energy to puncture the leaflet. At least a portion of the distal end of the catheter, of the hollow needle or both may be radiopaque or include other visualization aids in order to allow the physician to check that the position of the puncture is correct prior to delivering the pledget, via the release of the stored energy.

Component Stabilization and Suture Management System

An aspect of the present disclosure that can be used alone or in combination with aspects of the disclosure described above is a stabilization system for a transvascular cardiac repair that can be used to stabilize and/or adjust the position of a proximal portion (e.g., a handle) of one or more of the subassembly components described (e.g., the delivery catheter 100 and/or one or more of the various subsystems that can be advanced into the delivery catheter). The stabilization system can also include a suture management system for adjusting the length and/or the tension on one or both of the ventricular anchor suture and at least one leaflet suture.

In certain aspects, the suture management system for transvascular cardiac repair can assist in maintaining a substantially fixed force, or tension, on the sutures while the physician is adjusting the suture lengths and setting the tension of the suture lock. It should be understood by one of skill in the art that the term "substantially fixed force" may include allowing for some small changes in tension to occur. For example, in one aspect a 10% change in tension can occur.

An advantage of using such a suture management system is that the leaflet can be allowed to continue moving during the repair procedure in its "natural" state in response to the beating of the heart, but each pledget can be maintained substantially in contact with the leaflet through application of substantially constant tension on the sutures. Additionally, suture tangling can be prevented or minimized through use of the apparatus. A further advantage is that the physician can individually adjust each suture for decreasing or increasing tension to tailor the final movement of the leaflet, as appropriate. The suture management system can be located in the operating room near the physician during surgery. After the anchor and leaflet sutures are deployed in the patient, the ends of the sutures that pass through the delivery catheter can be attached to the suture management system and held in the aforementioned substantially constant tension.

In certain aspects of the disclosure, aspects of the stabilization system can have advantages and be used independently and without aspects of the suture management system or device. In a similar manner, in certain aspects of the suture management system can have advantages and can be used independently and without aspects of the stabilization system. Nevertheless, as described herein, certain advantages can be achieved system utilizing combinations and sub-combinations various aspects of the stabilization and suture management systems described herein.

Figure 34A:
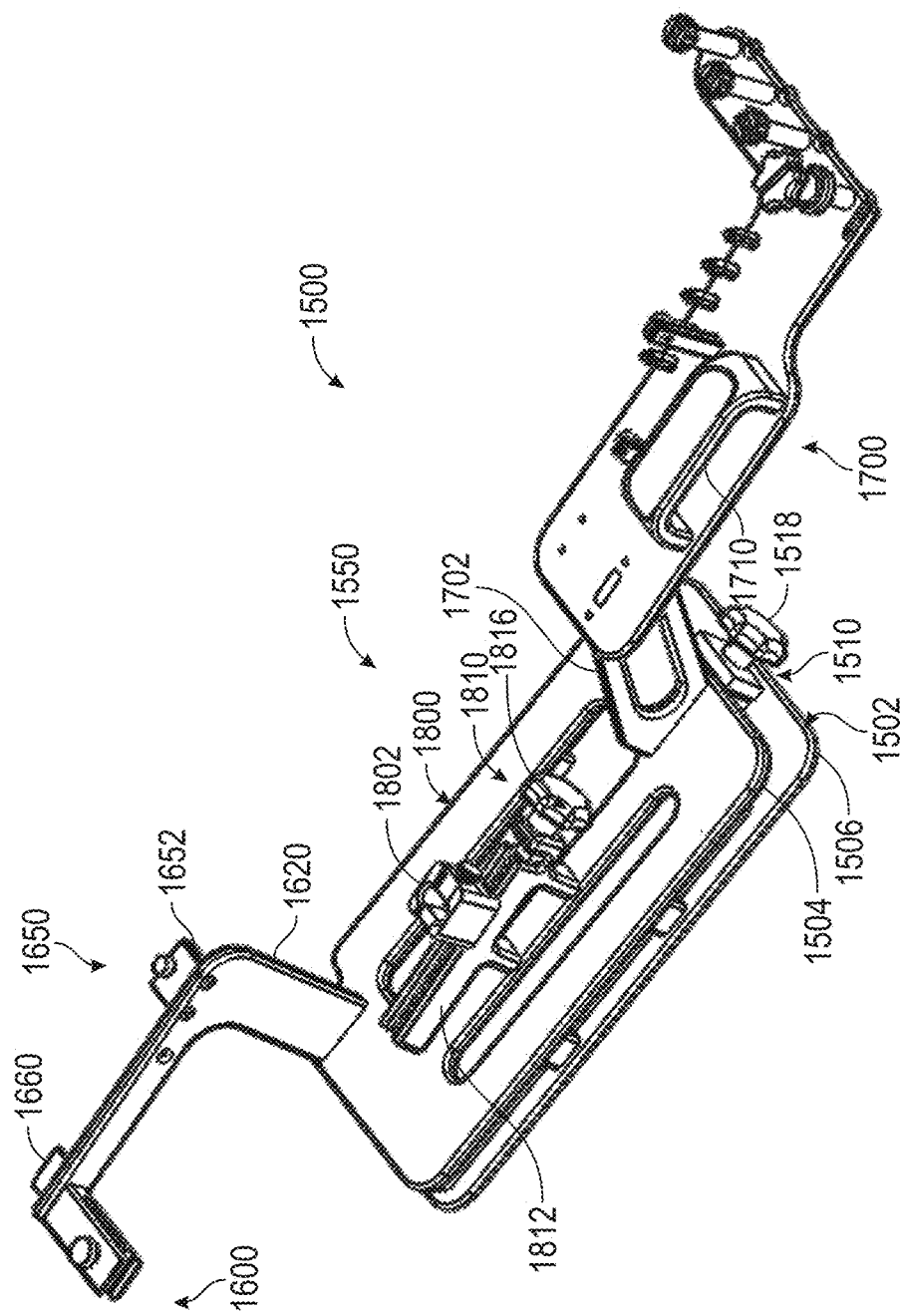
FIG. 34A is a top rear perspective view of a stabilization system and a suture management system in accordance with certain aspects of the present disclosure, in accordance with an embodiment.
Figure 34B:
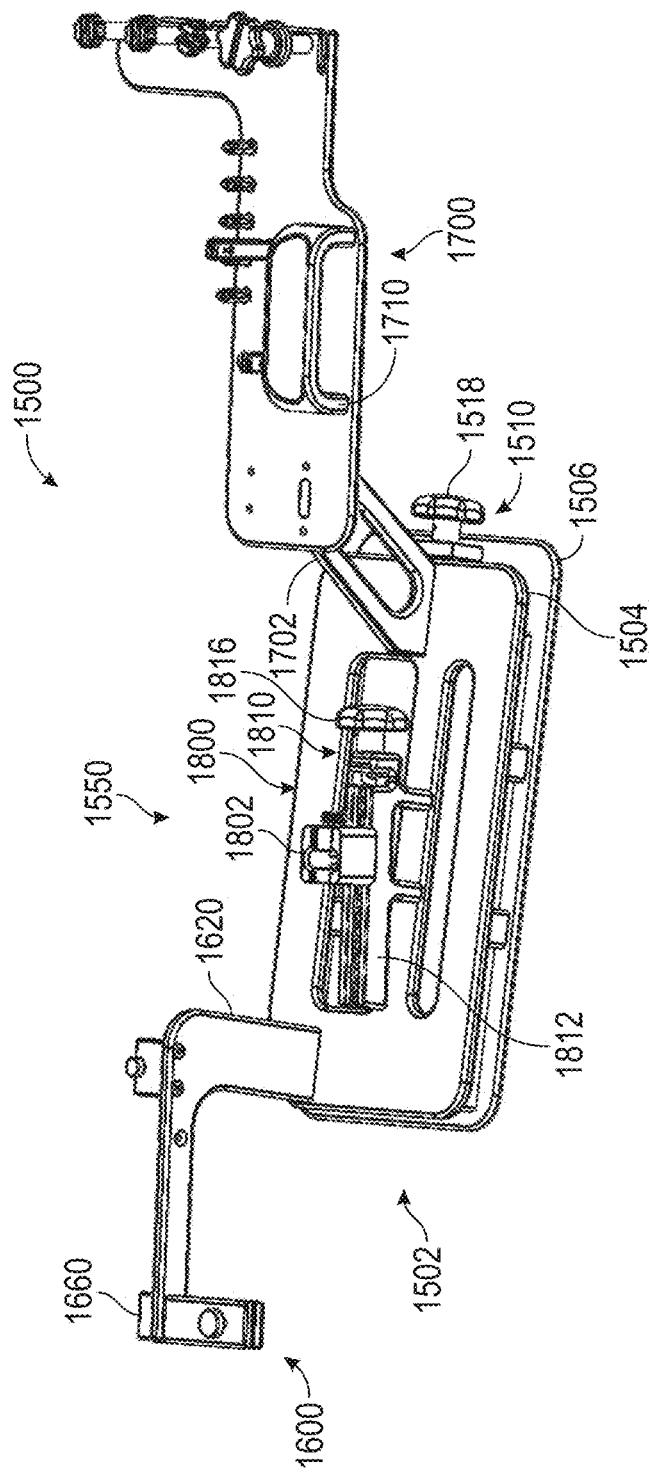
FIG. 34B is a top side perspective view of the stabilization system and the suture management system of FIG. 34A, in accordance with an embodiment.
Figure 35:
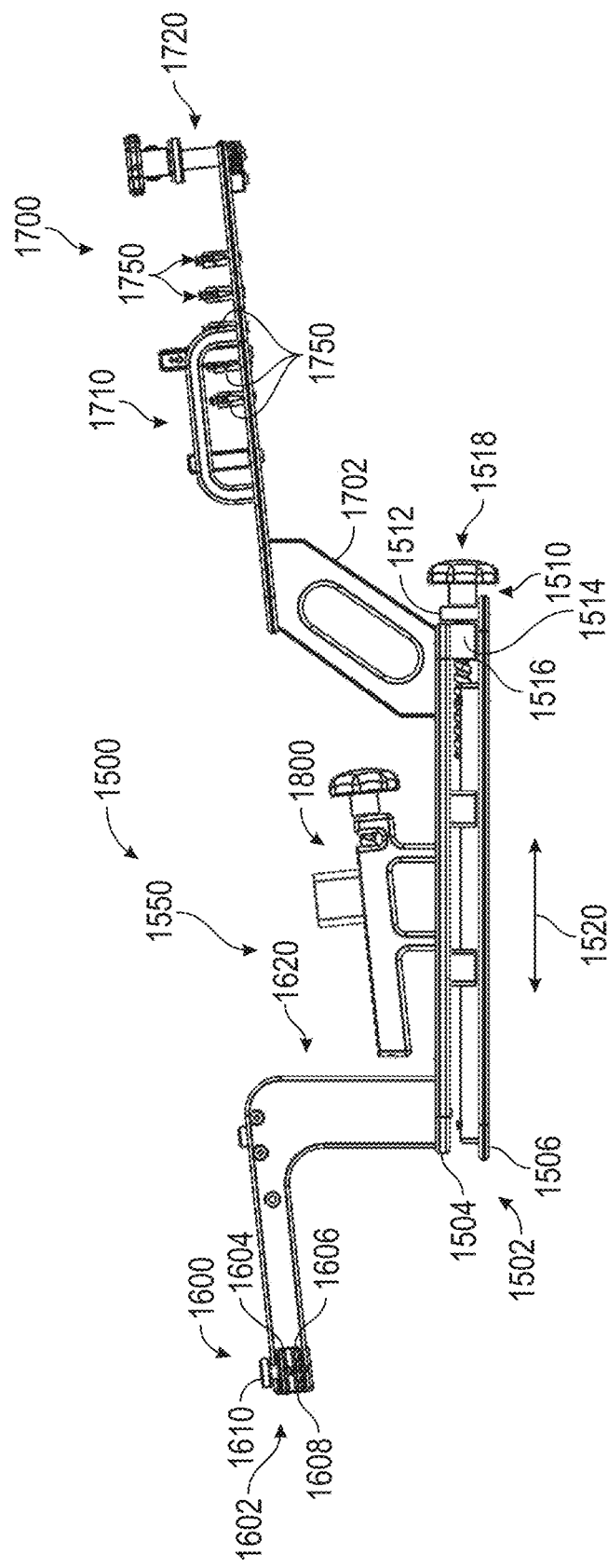
FIG. 35 is aside view of the stabilization system and the suture management system of FIG. 34A, in accordance with an embodiment.

FIGS. 34A and 34B illustrate an embodiment of a stabilization system (also referred to herein as "system") 1500. The system 1500 can comprises a base, or tray, 1502 which can be mounted to a stand or table (not shown) to avoid movement of the apparatus during a procedure. As shown in FIG. 35, the base can comprise an upper or top plate 1504 and a lower or bottom plate 1506. The upper and lower plates (also referred to herein as top and bottom plates) 1504, 1506 can be moveably connected to each other through an adjustable positioning mechanism 1510 (also referred to herein as "adjustment mechanism"), which in the illustrated embodiment can comprise a lower threaded boss 1512 that is coupled to a the lower plate 1506 and an upper threaded boss 1514 that is coupled to the upper plate 1504. A screw 1516 can extend through the lower and upper threaded bosses 1512, 1514. Axial motion of the screw 1516 (see FIG. 35) with respect to the lower plate 1506 can be limited such that rotation of a screw handle 1518 can cause the upper plate 1504 to move with respect to the lower plate 1506. In this manner, the adjustment mechanism 1510 can re-position in the upper plate 1504 (and components coupled thereto) with respect the direction of arrow 1520 to the lower plate 1506, which can be attached to the stand or table, as needed. The adjustment mechanism 1510 can include a lock to prevent movement between the upper and lower plates 1504, 1506. In several embodiments, other mechanisms can be used to similarly move the upper and lower plates reciprocally in axial direction with respect to each other such as sliding plates, complimentary rail and second channel or rollers.

A stabilization portion 1550 of the system 1500 can include several components that can be used to hold or stabilize components of the mitral valve chord repair devices described above. In particular, as will be described in detail below, the device can be used to hold or stabilize a proximal portion (e.g., a handle) of an introducer sheath, a delivery catheter 100, ventricular anchor delivery subsystem 300, a suture lock delivery subsystem 370, a pledget delivery subsystem or handle 1202, and/or proximal end or handle of a suture cutter catheter 500 and such components can be configured in accordance with the embodiments and aspects describe herein.

For example, the system can include a first docking platform 1600 that can be positioned on a distal portion of the system 1500 and can be referred to herein as the "distal docking platform 1600". The distal docking platform 1600 can be configured to hold or stabilize a handle or proximal portion of an introducer catheter through which various components of the delivery subsystems described herein can be advanced. With reference to FIG. 35, the distal docking platform 1600 can include a first stabilization device 1602 which can be in the form of a clamp 1602. The first stabilization device 1602 can be configured to clamp around a tubular portion of catheter such as an introducer or access sheath. In the illustrated embodiment, the clamp 1602 comprise pair of clamp plates, 1604, 1606 that can be moved towards and away from each other by a threaded post 1608 coupled to a handle 1610. Accordingly, in the illustrated arrangement manipulation of a control such as rotation of the handle 1610 can bring the plates 1604, 1606 together to clamp the introducer sheath (not shown) to the system 1500. In several embodiments, other mechanisms can be used in the first stabilization device 1600 to stabilize a catheter or introducer sheath such as friction fit devices, collets, or devices that positively connect to engagement features on a handle of the introducer sheath.

As shown in FIGS. 34A, 34B and 35, the clamp can be coupled to the upper plate 1504 base 1502 by an arm 1620. The arm 1620 can have an "L-shape" that positions the clamp 1602 above and forward along the axial the axial direction of the upper plate 1504. The arm 1620 can be coupled to the upper plate such that movement of the upper plate 1504 with respect to the lower plate 1506 causes axial movement of the clamp 1602.

Figure 36:
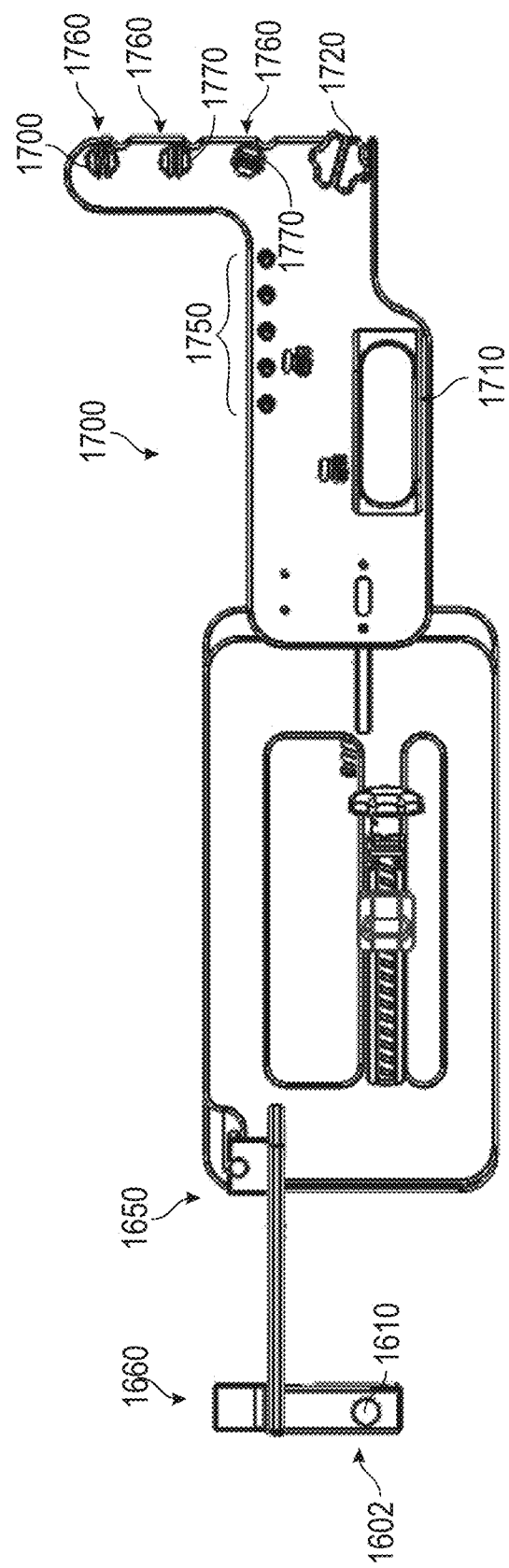
FIG. 36 is a top view of the stabilization system and the suture management system of FIG. 34A, in accordance with an embodiment.

As best seen in FIG. 36, distal docking platform 1600 can include a second stabilization device 1650. In the illustrated embodiment, the second stabilization device 1650 can also be in the form of a clamp and can be provided on the on the arm 1620. In the illustrated embodiment, the second stabilization device 1650 can be positioned on an elbow of the arm 1620. The second stabilization device 1650 can be used to stabilize another component of the mitral valve repair system descried herein. For example, the second stabilization device 1650 can be used to stabilize the proximal end (or handle) of the suture lock delivery subsystem (see e.g. FIG. 14).

The illustrated second stabilization device 1650 can include a clamp 1652 for holding components. See FIG. 34A. In the illustrated embodiment, the clamp 1652 comprises pair of plates that can be moved towards and away from each other by a control such as a screw similar to the first stabilization device. Accordingly, in the illustrated arrangement rotation of the screw can bring the plates together to clamp a portion of the suture lock delivery subsystem (not shown) to the system 1500. In several embodiments, other mechanisms can be used in the forward mount to stabilize the suture lock delivery subsystem such as friction fit devices, or devices that positively connect to engagement features on the suture lock delivery subsystem. As shown in FIG. 36, the arm may include a platform 1660 that can used to support a portion of the handle or other portion of the suture lock delivery subsystem. In one arrangement, the second stabilization device 1650 can be used to secure the front portion of the suture lock delivery subsystem while the rear or back portion of a handle suture lock delivery subsystem rests on the platform 1660.

With continued reference to FIGS. 35 and 36, the system 1500 can include a second docking platform 1700, which in the illustrated embodiment can be positioned proximal to the first docking platform 1600 and can also be referred to herein as the proximal docking platform 1700. The proximal or second docking platform 1700 can be supported above the base 1502 by an arm 1702 that extends from the top plate 1504. The proximal docking platform 1700 can be generally at the same elevation as the stabilization devices described above. The proximal docking platform 1700 can include components of a suture management system, which will be described in more detail below. The proximal docking platform 1700 can include a third stabilization device 1710. The device 1710 can include an elongate concave support surface such as a U-shaped channel extending in the axial direction that can be used to support components such as a handle of the ventricular anchor delivery subsystem according to embodiments described herein. The second docking platform 1700 can be coupled to the top plate 1504 through the arm 1702 such that movement of the top plate 1504 causes the platform 1700 to move. Accordingly, in the illustrated arrangement, proximal docking platform 1700 and the distal platform 1600 can both carried by the upper plate and in several embodiments can be fixedly carried by the upper plate.

With continued reference to FIGS. 35 and 36, the system 1500 can include a third docking platform 1800. The third docking platform 1800 can be positioned between, in an axially direction of instruments being mounted thereto, the first and second docking platforms 1600, 1700 which as described above can be positioned in distally and proximally with respect to each other. The third docking platform 1800 can also be referred to herein as the intermediate docking platform 1800. The intermediate docking platform 1800 can include a fourth stabilization device 1802, which can be in the form of a vice or clamp. The intermediate docking platform 1800 can be positioned can be positioned between the first and second docking platforms 1600, 1700. The intermediate docking platform 1800 can include an adjustment mechanism 1810, which in the illustrated embodiment can comprise a threaded engagement between the stabilization device 1802 and a lower rail 1812. The lower rail 1812 can be fixed with respect to the upper plate 1505. A screw 1816 can be rotated to move the stabilization device 1802 with respect to the rail 1812 and upper plate 1504. In this manner, the adjustment mechanism 1810 can re-position in the fourth stabilization device (and components coupled thereto) to the lower plate 1506, which can be attached to the stand or table, as needed. The adjustment mechanism 1810 can include a lock to prevent movement. The intermediate docking platform can be carried by the upper plate 1504. The adjustment mechanism 1810 can also re-position in the fourth stabilization device (and components coupled thereto) to the upper plate 1504 and components that are carried by or fixedly carried by the upper plate such as the distal and proximal docking platforms (and components coupled thereto).

In one embodiment of use, the fourth stabilization device can be used to stabilize the delivery catheter such as according to the delivery catheter 100 described above. In certain embodiments, the first stabilization device 1650 can be used to stabilize an introducer catheter while the fourth stabilization 1802 device can used to stabilize the delivery catheter 100 which is inserted through the introducer catheter. In this manner, rotation of the screw 1816 can allow fine movement of the delivery catheter with respect the introducer catheter. That is movement of the intermediate docking platform can move the delivery catheter with respect to the distal docking platform and the introducer catheter mounted thereto.

Figure 37:
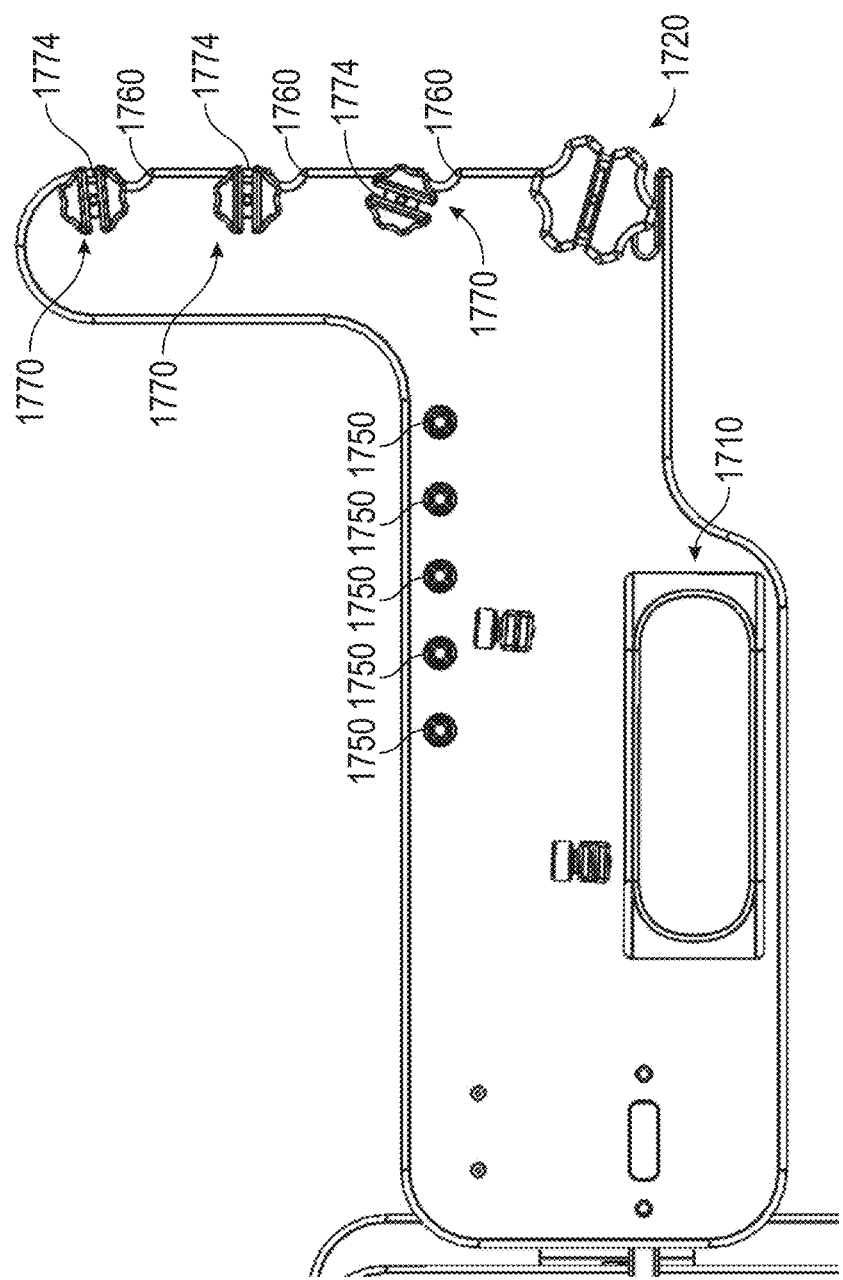
FIG. 37 is a closer top view of the rear portion of the stabilization system and the suture management system of FIG. 34A, in accordance with an embodiment.
Figure 38:
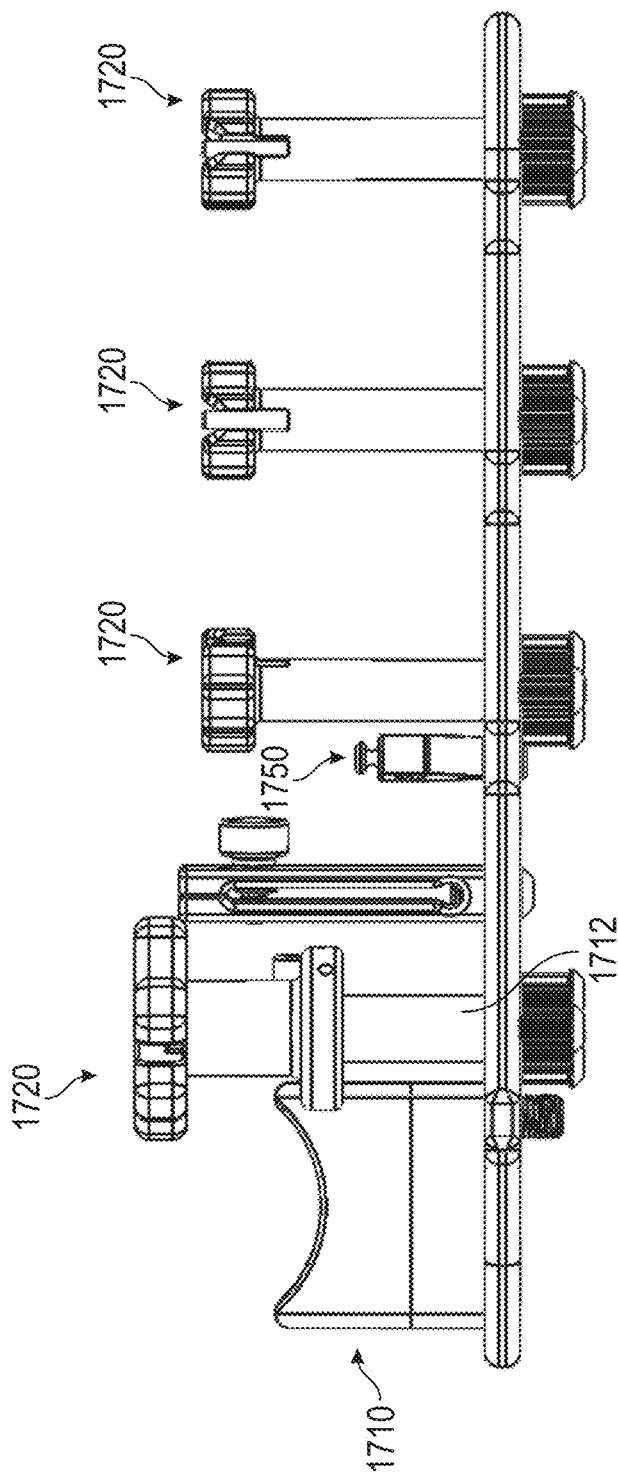
FIG. 38 is a closer review view of the stabilization system and the suture management system of FIG. 34A, in accordance with an embodiment.

With reference to FIGS. 37 and 38, a suture management system 1700 can include at least one, two, three or more tensioning components that can be used to hold each suture and assist to keep the sutures under tension at all times, thus avoiding slack which could result in the pledgets being pulled into the left atrium or the left ventricle from the force created with each heartbeat, or additionally to avoid slack sutures binding up in the left atrium or left ventricle, or even slack sutures binding up with other chordae in the left ventricle.

For example, in one embodiment, the anchor suture may be attached to an anchor tension component 1720. The anchor tension component 1720 can comprise a rotatable spool 1712 equipped with a torque limiting fixture such as a clutch to limit the amount of tension that can be applied to a suture (for example a suture coupled to the ventricular anchor) wrapped around the spool. The anchor tension component 1720 can advantageously avoid or reduce the risk of the anchor being pulled out of the heart wall if too much tension is applied to the anchor suture. In another embodiment, the anchor tension component 1720 may comprise a spring-loaded post configuration to impart tension to the sutures. In one embodiment, a proximal end of a suture coupled to the ventricle anchor 302 of the ventricular anchor delivery subsystem 300 can be wrapped around the anchor tension component 1720 after the ventricle anchor is deployed. In this manner, a constant tension can be applied to the suture and the torque clutch limiting fixture can prevent or limit excessive tension from being applied to the ventricle anchor. In one embodiment, the torque limit of the clutch is between about 2 N to about 5 N. In certain example embodiments, the torque limit of the clutch is between 2 N to 5 N.

With continued reference to FIGS. 37 and 38, at least one, two, three or more suture adjustment fingers 1770 can be provided allow adjustment of the pledget suture tension on the leaflet. In use, a suture that is coupled to a pledget can be attached to a tensioning force, such as a weight 1750 to provide the desired tension. In certain embodiments, the weight can be within the range from about 2 to about 8 grams. In certain example embodiments, the weight can be within the range from 2 to 8 grams. In the illustrated embodiment, the weights 1750 can be stored on the proximal platform 1700 by providing weight mounts such as a plurality of holes, recesses or sockets that can receive the weights 1750. The suture (e.g., a leaflet suture) can be placed in a suture guide 1760 which can be notch or groove formed on the platform 1700. The guide 1760 can be configured to allow the suture to axially slide while providing some constraint in lateral movement. The proximal docking platform 1700 can include at least one, two, three, or more suture guides 1760. By hanging the end of the suture (for example a leaflet suture) attached to a weight 1750 over the edge of a platform 1700 a constant tension can be applied to the pledget sutures which can be useful in limiting or preventing suture tangling. As noted above, the platform 1700 can be provided with more than one guide 1760 so that more than one suture can be hung over the edge of the platform 1700.

As shown in FIGS. 37 and 38, the platform 1700 can also include the suture adjustment features or fingers 1770 that can be positioned near or adjacent the notches or grooves 1760. The suture adjustment features 1770 can comprise rotatable spools. Each spool can include a slot 1774 through which a suture can extend. The rotatable spools 1770 can then be rotated to adjust the tension on the suture.

The suture management system can provide a dynamic leaflet management system. An advantage of using such a system is that the leaflet can be allowed to continue moving during the repair procedure in its "natural" state in response to the beating of the heart, but each pledget can be maintained substantially in contact with the leaflet through application of substantially constant tension on the sutures. Additionally, suture tangling can be prevented or minimized through use of the system. A further advantage can include providing the physician with the ability to individually adjust each suture for decreasing or increasing tension to tailor the final movement of the leaflet, as appropriate. For example, in an embodiment of use, after the advancing the suture lock (embodiments described above), into the patient and before locking and cutting the sutures, the tensions on the sutures can be adjusted to while viewing valve competency. This can be done by rotating the spools to increase or decrease the slack in the wire and the corresponding tension. Once the desired tension is achieved, the suture lock can be activated as described above.

A plurality of sutures can be fixed to the suture management apparatus, including for example up to 4, and multiple suture management apparatuses may be used, as needed. The apparatus components may comprise any suitable sterilizable materials which meet the apparatus performance requirements, including non-limiting examples such as stainless steel, acetal resin such as polyoxymethylene, PTFE, aluminum, 3D printed resin materials, and the like.

Leaflet Tissue Anchor Deployment System

Figure 39:
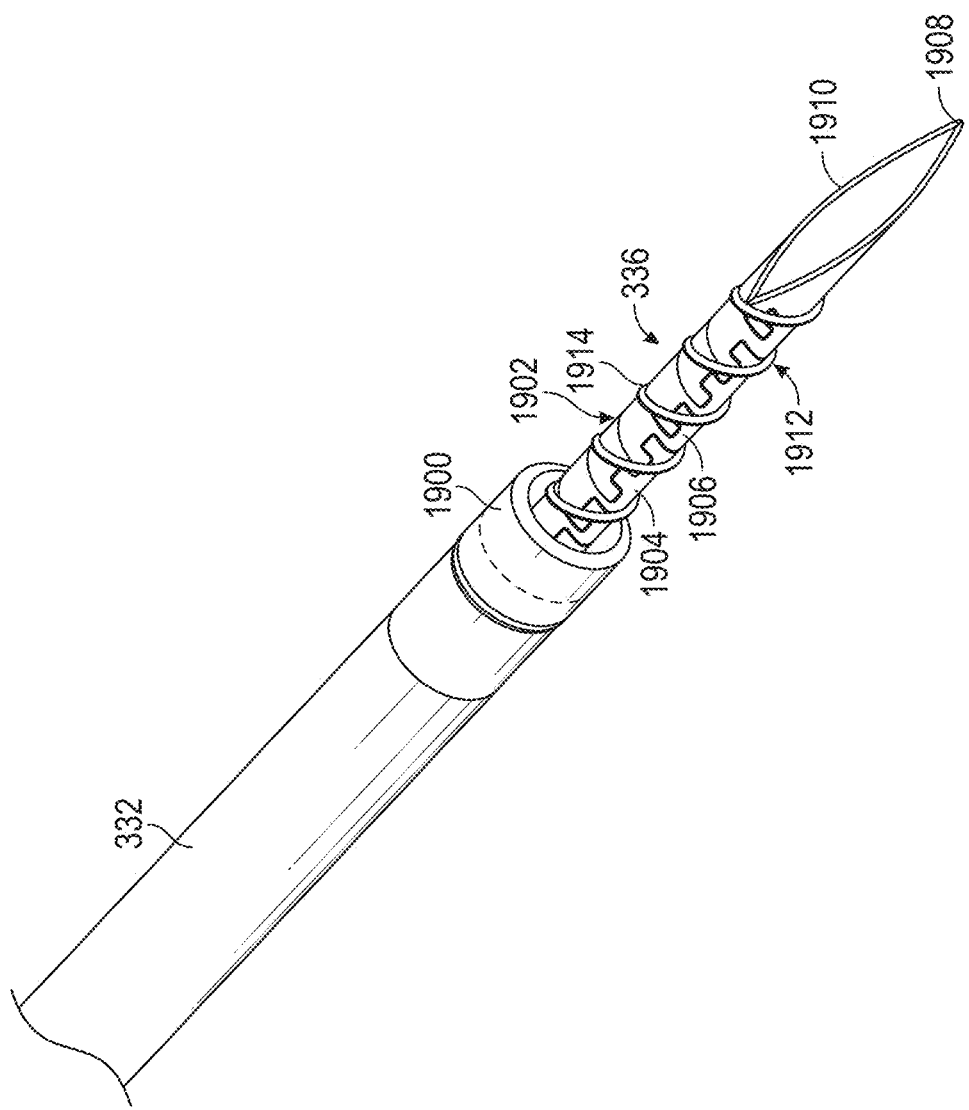
FIG. 39 is a distal end perspective view of an alternate leaflet anchor deployment needle, in accordance with an embodiment.

In accordance with a further aspect of the present disclosure, there is provided an alternative leaflet tissue anchor deployment system. Referring to FIG. 39, a needle deployment catheter 332 axially reciprocally carries a needle 336. A radio opaque marker band 1900 is provided at the distal end of the needle deployment catheter 332, so that positioning of the marker band 1900 can be visualized in relationship to the mitral valve leaflet while the needle 336 is proximal retracted within the catheter 332.

In FIG. 39, the needle 336 is illustrated in the distally advanced configuration. Needle 336 comprises a tubular body 1902 having a sidewall 1904 and at least one flexibility enhancing feature such as a slot pattern. In the illustrated embodiment at least one serpentine slot 1906 extends through the side wall. The serpentine slot 1906 may be formed in any variety of ways known in the art, such as by laser etching a hypo tube. The serpentine slot 1906 enhances the lateral flexibility of the needle 336 along a deflection zone, to facilitate aiming at the appropriate location on the mitral valve leaflet. The deflection zone is typically less than about 4 cm or less than about 2 cm in length, but long enough to contain the entire length of the pledget. In certain example embodiments, the deflection zone is typically less than 4 cm or less than about 2 cm in length, but long enough to contain the entire length of the pledget.

The needle 336 terminates distally in a sharpened tip 1908 separated from the tubular side wall 1904 by an inclined face 1910. The inclination angle of the face 1910 will generally be within a range of from about 30 degrees and 85 degrees, alternatively within a range of from about 70 degrees and 80 degrees, and in one implementation is about 75 degrees. In certain example embodiments, the inclination angle of the face 1910 will generally be within a range of from 30 degrees and 85 degrees, alternatively within a range of from 70 degrees and 80 degrees, and in one implementation is 75 degrees.

At least one tissue retention element 1912 is provided operable to permit rapid, forcible powered advancement of the needle 336 distally through tissue, while being resistant to proximal retraction of the needle 336 from the target tissue. The retention element 1912 may comprise any of a variety of structures which extend radially outwardly from the tubular sidewall 1904, such as at least one or two or five or 10 or more barbs, annular rings or tabs. In the illustrated embodiment, the retention element 1912 comprises annular rings in the form of a continuous helix 1914 which may be formed from a polymeric strand or metal wire wrapped into a helix around the tubular body 1902. In one implementation, a helical wire such as a 0.008 inch wire is welded or otherwise secured to the tubular body 1902.

Distal advance of the needle 336 from the diploma catheter 332 at a sufficient velocity enables the needle 336 to penetrate the leaflet, without the need for the leaflet stabilization anchor such as 406 disclosed in FIG. 3. Retention elements 1912 provide sufficient retention to retain the leaflet on the needle, until following deployment of the pledget. Thereafter, the needle may be proximally retracted without rotation, or may be rotated, to unscrew and remove the needle from the leaflet.

If additional leaflet stabilization is desired, stabilization may be achieved by the temporary leaflet anchor disclosed previously herein, or by alternative mechanical techniques of grasping or pinching the leaflet or by suction or freeze-grabbing with a cryo-catheter. These techniques would include a cryo-catheter of the type used in ablation procedures to freeze a target tissue. These cryoablation-catheters used for atrial fibrillation often attach themselves to the mitral leaflets accidentally and need to be deactivated to release the attached leaflets. This same cryo attachment can be used to locate and isolate the leaflet in question for stabilization during deployment of the leaflet anchor deployment needle. The cryo catheter uses a gaseous exchange (NO or Argon) to drop the temperature of the tip of the catheter, and can reach temperatures as low as minus 75 degrees Celsius.

Actuator Control System

Deployment of the mitral leaflet anchor described herein is accomplished by piercing the leaflet from the atrial side of the valve. In order to avoid the need for a grasping structure to capture and support the leaflet during leaflet puncture, and use a needle such as that shown in FIG. 39, the distal ejection of the leaflet anchor deployment needle can be timed to correspond with peak (systolic) pressure in the ventricle which occurs at about or around the QRS wave. This synchronizes piercing of the leaflet with mitral valve closure so that systolic pressure within the ventricle provides the necessary back up support during penetration of the leaflet from the atrium.

Timing of leaflet needle launch with the cardiac cycle can be accomplished manually by the clinician, or can be partially or fully automated depending upon the desired implementation. For example, a visual or audio signal or fluoro image may alert the clinician to the timing of the QRS complex, allowing the clinician to press the launch trigger or other control to deploy the needle. Since clinician reaction times can vary, it may be desirable to partially or fully automate the needle launch procedure.

For example, a needle 338 may be provided with an automated needle driver, such as a solenoid carried by the proximal end of the catheter. The solenoid is activated to distally project the needle in response to an activation signal that corresponds in time to a target time in the cardiac cycle, such as during closure of the mitral valve.

Alternatively, the activation signal may be in the form of a visual, tactile or auditory signal to the clinician, in response to which the clinician pushes a control such as a button or slider to manually advance the needle, or pushes a control that activates an electromechanical or mechanical needle driver.

In another implementation of the disclosure, needle deployment can be accomplished manually by the clinician, but only after disengagement of a lock out. In this implementation, a removable mechanical interference may be created at or linked to a proximal portion of the needle shaft. A distally facing interference surface may be carried by a radially outwardly extending tab or annular flange coupled to the needle, or a distal surface of an aperture extending through the needle. For the present purpose, 'needle' refers to the needle itself, as well as any proximally extending structure (e.g., extension tube or rod) that is mechanically linked to and moves with the needle as will be understood by those of skill in the art.

A proximally facing interference surface is configured to be movable between an engaged configuration in which it engages in an interference fit with the distally facing interference surface on the needle, and a disengaged configuration in which the distally facing interference surface and associated structure is free to advance distally to eject the needle. The proximally facing interference surface may be carried on a stop such as an axially movable pin or a pivotable or sliding lever which is movably carried by the proximal handpiece. A stop driver such as a solenoid is configured to move the stop between the engaged and disengaged configurations.

The stop may be initially engaged, to prevent deployment of the needle. In response to an activation signal indicating the target time (e.g., during or about or around at the QRS complex), the stop is retracted into the disengaged configuration. This prevents the clinician from prematurely deploying the needle, but allows manual deployment of the needle at the desired target time. The stop may be automatically returned to the engaged configuration following a preset time window following the activation signal, to prevent late deployment of the needle and create a narrow window in which the clinician is allowed to launch the needle. If the clinician failed to timely deploy the needle within the window, the opportunity to launch the needle will reappear with subsequent QRS complex occurrences.

A variety of techniques have been developed to detect the QRS complex directly, or a proxy for that point in the cardiac cycle. Direct detection techniques include power spectrum analysis, bandpass filtering, differentiation, template matching, and waveform feature-dependent real-time techniques. Proxies include blood pressure such as measured intravascularly in the arterial or venous side or within an atrium or ventricle of the heart, or measured noninvasively such as peripheral blood pressure. Venous side measurements can serve as a proxy for the timing of the QRS complex since the aortic valve is open when the mitral valve is closed, leaving a fingerprint on the cyclic venous pressure curve. The data from any of the foregoing sources may desirably be adjusted to take into account any time delay from the true QRS complex, depending upon the desired time sensitivity. The ECG signal may be obtained from a conventional ECG monitor which will normally already be present and in operation in the surgical suite.

A typical ECG waveform consists of a P wave indicating atrial depolarization, a QRS complex indicating ventricular depolarization, a T wave indicating ventricular repolarization, and a possible U wave in some cases indicating the extension of the repolarization. The dominant activity of an ECG usually relates to identification of the QRS complex in real time, for various monitoring and diagnostic purposes. The QRS complex or wave normally lasts about 80 to 120 ms in duration and corresponds to the commencement of ventricular contraction and ejection of blood via the aortic valve. In certain example embodiments, the QRS complex or wave normally lasts 80 to 120 ms in duration and corresponds to the commencement of ventricular contraction and ejection of blood via the aortic valve. This also corresponds to pressure responsive closure of the mitral valve, which is significant for the purpose of the present disclosure.

FIGS. 40-45 depict a system which provides control of an actuator in synchrony with heart 10. As used herein, actuator refers to anything that is activated in response to a control signal triggered by an event in the cardiac cycle, such as a visual, audio or tactile feedback to the clinician, an automated needle firing mechanism, or a lockout mechanism in a manually operated needle deployment embodiment, that prevents the clinician from deploying the needle until the actuator unlocks the firing mechanism.

Figure 40:
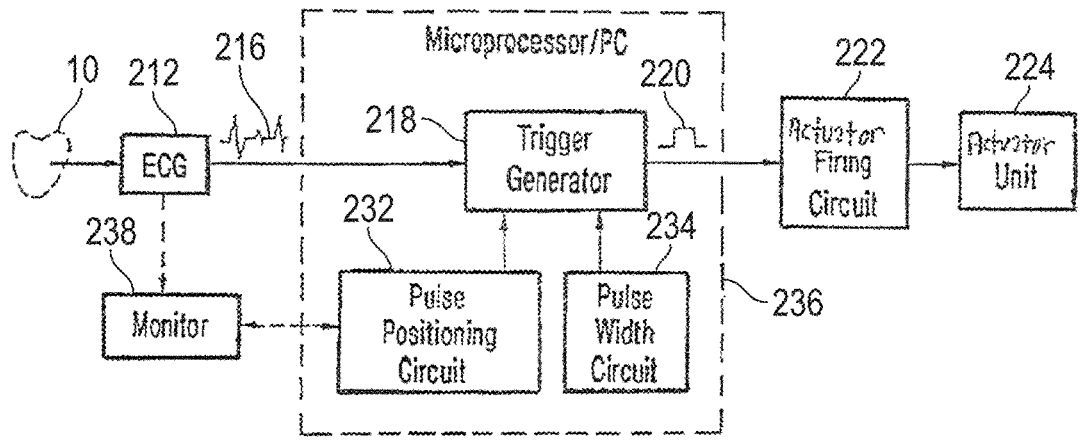
FIG. 40 is a schematic block diagram of a system to provide a synchronized control signal based upon detection of a preselected point in the cardiac cycle, in accordance with an embodiment.
Figure 41:
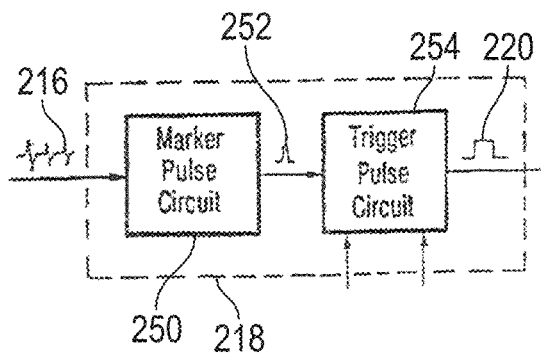
FIG. 41 is a schematic block diagram of a trigger generator used in the system shown in FIG. 23, in accordance with an embodiment.

An overview of such a system is shown in FIG. 40 and is seen to comprise a component to sense the cardiac cycle 212, a component to generate a trigger pulse for the actuator in response to the sensed cardiac cycle 218, a component to position the leading edge of the trigger pulse at a specified time within the cardiac cycle 232, a component to define the width of the trigger pulse to occur during the cardiac cycle 234, and a component to control the firing of the actuator in response to the trigger pulse and for a period in response to the defined width 222.

In particular, electrocardiogram (ECG) unit 212 electrically connects to heart 10 of a patient so as to sense the cardiac cycle and provide ECG signal 216. ECG unit 212 may be connected to the heart in any known manner for sensing cardiac signals including surface mounted electrodes typically adhesively mounted to the patient's chest, as well as internal or intracavitary electrodes. As an alternative, the sensing connection may further be incorporated integrally with the catheter 332, such as through the provision of one or more electrical leads extending through the catheter 332 to conduct electrical signals or operate a sensor (e.g., pressure sensor) or electrode at the distal end of the catheter 332. Electrodes may be either of unipolar design, in which case a surface contact may be used or bipolar design. The electrical lead may extend proximally through catheter 332 and end in a standard electrical connector which may then be removably connected to the ECG unit 212 and communicate sensed signals 216 thereto.

Signal 216 is delivered to trigger generator 218. Trigger generator 218 provides a trigger pulse 220 to actuator firing circuit 222. Actuator firing circuit 222 energizes actuator 224 such as to fire the needle or remove a barrier that inhibited the clinician from prematurely firing the needle as has been discussed.

The position of trigger pulse 220 in the heartbeat cycle of ECG signal 216 is determined by pulse positioning circuit 232. The width of the pulse 220 and its duration during the heartbeat cycle is determined by pulse width circuit 234. Trigger generator 218, as well as pulse positioning circuit 232 and pulse width circuit 234, may be included as an additional board in a PC or a microprocessor 236, in which case the system can be controlled through a computer keyboard and suitable software. PC 236 and ECG 212 may have separate monitors, or they may have a single monitor 238 which displays both the ECG and information about or around the trigger pulse 220.

Trigger generator 218 may include a marker pulse circuit 250 which provides marker pulse 252 and trigger pulse circuit 254 which responds to marker pulse 252 to create trigger pulse 220. Alternatively, marker pulse circuit 250 is included in the ECG itself in some cases.

Figure 44:
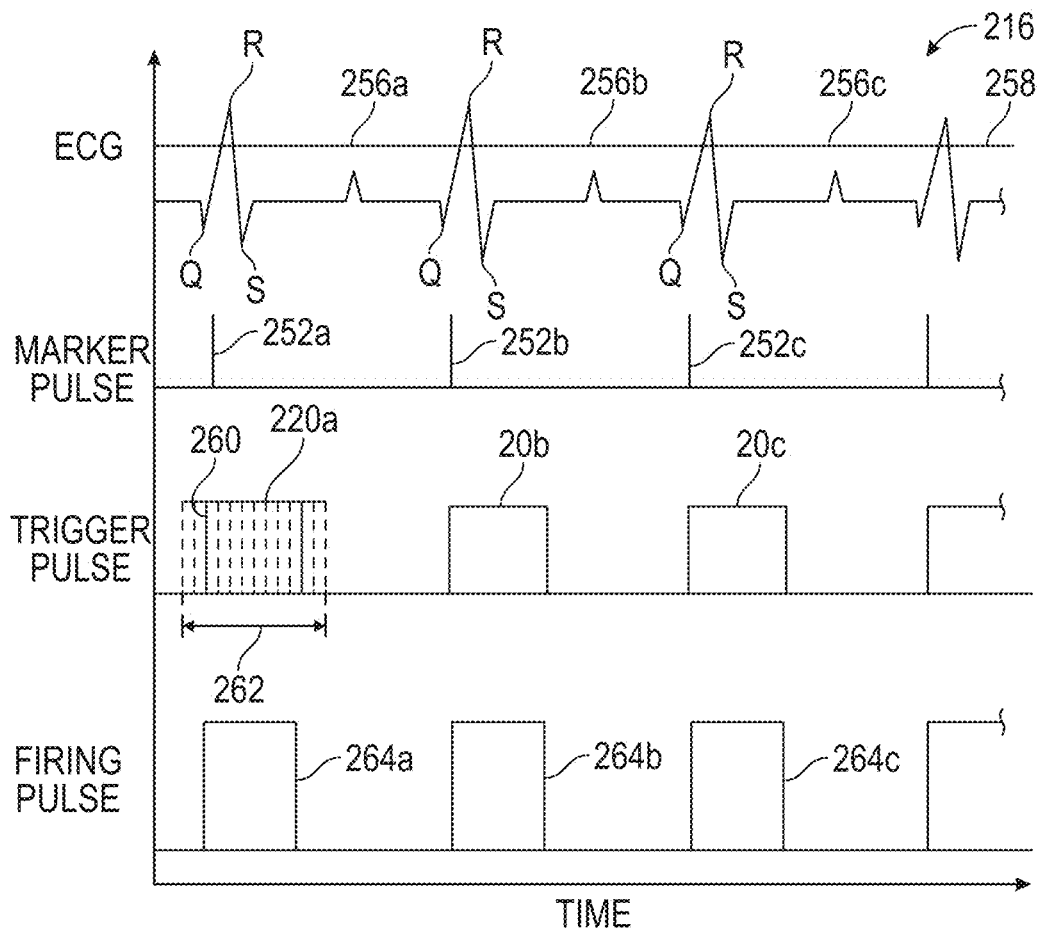
FIG. 44 illustrates an ECG signal, marker pulse, trigger pulse and firing pulse waveforms occurring in the system depicted in FIG. 40, in accordance with an embodiment.
Figure 45:
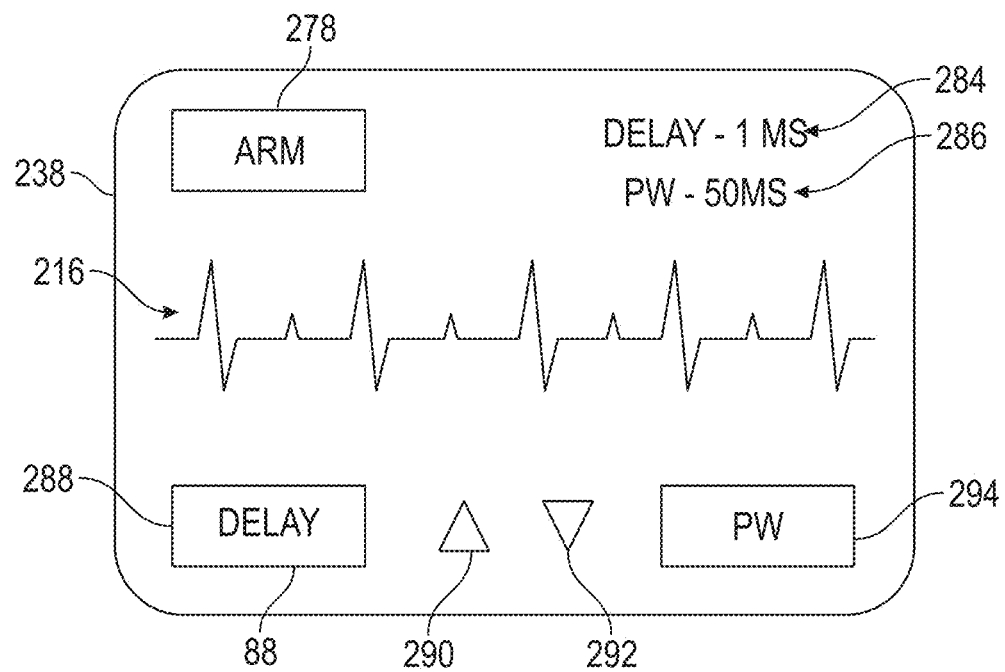
FIG. 45 illustrates a touch sensitive monitor which may be used in the device depicted in FIG. 40, in accordance with an embodiment.

This can be better understood with reference to FIG. 44, where ECG signal 216 may be seen as consisting of a series of heartbeat cycles 256a, 256b, 256c each of which contains the waveforms Q, R, S and T. Where waveform R crosses preselected threshold 258, marker pulses 252a, 252b, 252c are created. Trigger pulses 220a, 220b, 220c are then created by trigger pulse circuit 254. The position of the leading edge 260 and the overall width 262 of each trigger pulse 220 is determined respectively by pulse positioning circuit 232 and pulse width circuit 234. In response to trigger pulse 220, a firing pulse 264 indicated as 264a, 264b and 264c, FIG. 24, is created to energize actuator 224.

Figure 42:
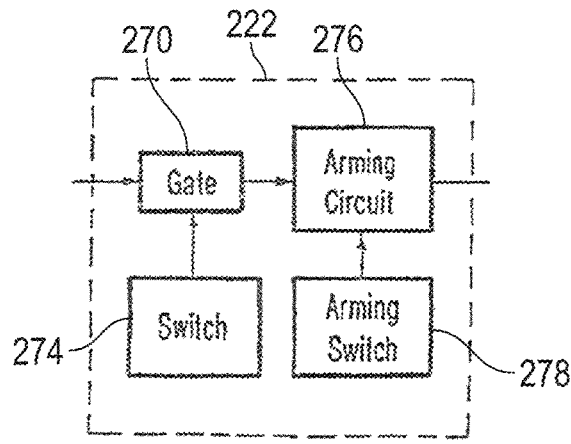
FIG. 42 is a schematic block diagram of an actuator firing circuit used in the system shown in FIG. 40, in accordance with an embodiment.
Figure 43:
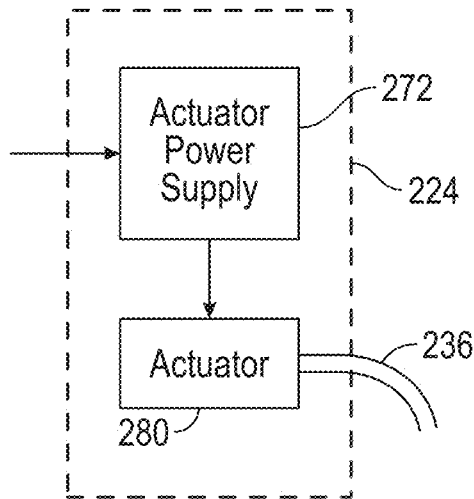
FIG. 43 is a schematic block diagram of an actuator unit used in the system shown in FIG. 40, in accordance with an embodiment.

In FIG. 42, actuator firing circuit 222 is shown to include gate 270 which generally inhibits the delivery of trigger circuit 220 to actuator laser power supply 272 (when relevant) in actuator unit 224. The inhibiting effect of gate 270 can be overcome when the operator activates a switch 274. Trigger pulse 220 is still inhibited, however, by arming circuit 276 which in turn can have its inhibiting effect overcome by the operation of arming switch 278. This double lock on the delivery of trigger pulse 220 to actuator power supply 272 ensures that the firing of the actuator is truly desired and not accidental. Thus the operator must first arm the system by operating arming switch 278 to enable arming circuit 276. Then and only then is he able to pass the next occurring trigger pulse 220 through gate 270 to the actuator power supply 272 by actuating switch 274. Further details of a suitable design for synchronizing a trigger signal with the QRS wave can be found in U.S. Pat. No. 5,674,217 to Wahlstrom, et al, filed Nov. 16, 1993, the disclosure of which is hereby incorporated in its entirety by reference herein.

Meltable Suture

The disclosed system can, in certain embodiments, utilize polytetrafluoroethylene (PTFE) or expanded polytetrafluoroethylene (ePTFE) sutures due to their desirable tensile strength and relatively low creep. However, PTFE and ePTFE sutures are not easily severable by cutting or by melting.

In order to overcome this challenge, some embodiments of the present disclosure relate to sutures wherein at least a portion of the suture is meltable. In some embodiments, the suture can be a bi-component suture, wherein a distal end of the suture comprises a meltable suture material and the proximal end of the suture is a non-meltable suture material. In some embodiments, the distal portion of the suture comprises less than 50% of the total length of the suture. In other embodiments, the proximal end of the suture comprises greater than or equal to half the total length of the suture. In another embodiment, the bi-component suture may comprise one portion of a meltable suture, wherein the meltable portion is a relatively small meltable zone with non-meltable suture material on either side of the meltable zone. The meltable zone should be located at a position on the suture so that it does not impact the tensile strength or creep resistance of the implanted prosthetic chordae. When a bi-component suture is used, the junction between the meltable portion and the non-meltable portion should be placed proximate to the location of the suture lock or the point at which the suture will be tied or knotted so as not to affect the strength of the suture. None or a relatively small portion of the meltable suture should be under tension during the normal functioning of the heart after implantation of the prosthetic chordae. The bi-component suture should have enough tensile strength over the entire length of the suture, and especially at any interface of a meltable portion with a non-meltable portion, so that the physician can provide enough tension on the suture during the tensioning step so that the suture does not break when tension is applied to correct the mitral valve regurgitation.

Figure 46:
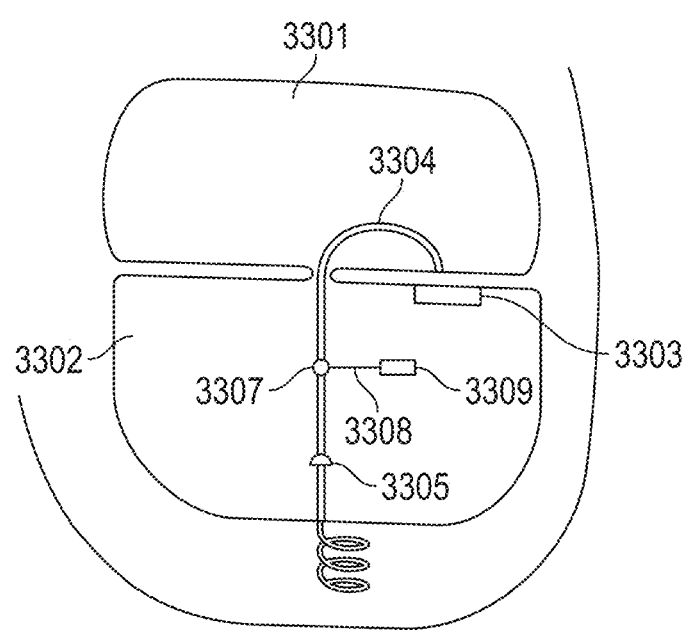
FIG. 46 is a schematic side perspective view of a heart with a transcatheter mitral chordal repair system in accordance with aspects of the present disclosure, in accordance with an embodiment.

FIG. 46 illustrates one embodiment of a schematic side view of a heart, wherein the left atrium 3301 and the left ventricle 3302 are shown separated by the posterior and anterior mitral valves (not labeled). In this embodiment, a pledget 3303 is secured to the ventricular side of the leaflet with one portion of non-meltable suture 3304 extending from the pledget into the left atrium 3301 passing to the left ventricle 3302 between the two leaflets. In the left ventricle 3302, a tissue anchor 3305 is secured to the heart tissue using a helical anchor 3306. Non-meltable suture 3308 is joined to non-meltable suture 3304 with knot 3307. Meltable suture 3309 shows only a portion of the suture after having been cut with the remaining distal end of the meltable suture having been retracted through the catheter (not shown). In this embodiment, all of the tension of the beating heart is on sutures 3304 and 3308 with substantially no tension on meltable suture 3309. The length of the distal ends of the sutures should be as small as possible. Note that only one distal end of sutures 3304 and 3308 are shown.

The system can further comprises a suture cutter. Once the tension is set in the one or more sutures and the mitral valve regurgitation is corrected or minimized, the suture cutter can be advanced through the catheter placed over the distal ends of one or more of the sutures in order to melt the meltable suture, thereby severing the suture. The distal end of the meltable suture can be retracted through the catheter to be removed from the patient. Each of the one or more sutures can be cut one at a time or two or more sutures can be melted at one time. The suture cutter comprises a heat source, for example, a coil that can be energized in order to heat the coil so that the temperature proximate to the coil rises above the melting temperature of the meltable suture.

Figure 47:
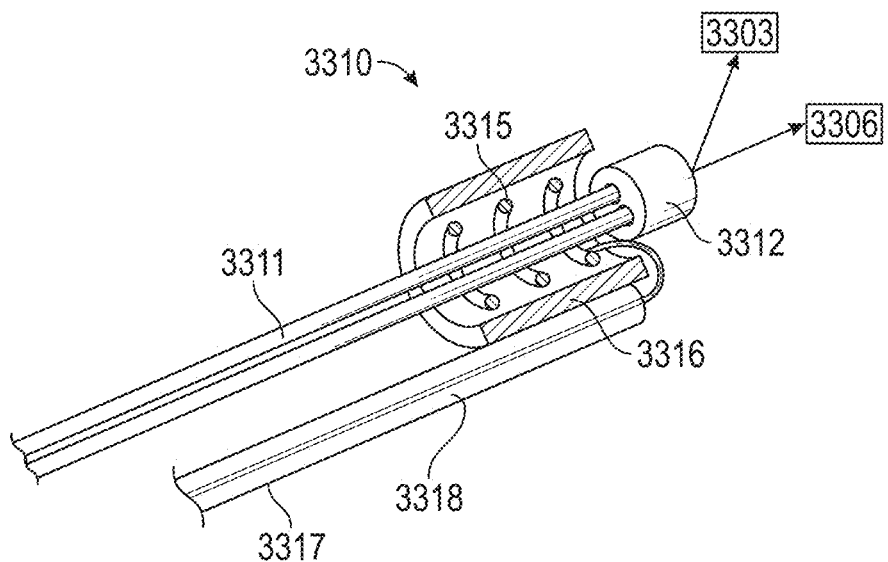
FIG. 47 is a cut-away side perspective view of a suture cutter mechanism in accordance with aspects of the present disclosure, in accordance with an embodiment.

FIG. 47 illustrates an embodiment wherein a suture cutter 3310 is advanced through the catheter (not shown) over the distal ends 3311 of the sutures and to the suture lock 3312. The suture connected to the leaflet pledget 3303 and the suture connected to the anchor 3306 having been tensioned to minimize or correct mitral valve regurgitation are clamped in the suture lock 3312 so that sutures are not able to move through the suture lock 3312 as tension is applied to the sutures during the normal functioning of the heart. The suture cutter 3310 can comprise a heating source, for example, a heater coil 3315, a short tube comprising a heater housing 3316 that is coaxial to the heater coil 3315, which may serve to insulate the heart structure from the heat, and has a larger inside diameter than the outside diameter of the heater coil, a hypotube 3317, which may serve to prevent blood from entering the catheter, and an insulated conductor 3318 which provides electrical energy to the heater coils to provide a temperature above the melting point of the meltable suture. The transmission of the electrical energy to the heater coil is actuated by the physician when the suture cutter has been moved into position and can be deactivated by the physician following the cutting of the sutures. In FIG. 47, the non-meltable suture (not labeled) extends just past the suture lock (toward the direction of the suture cutter) and the meltable portion of the suture is located coaxial with and inside the inner diameter of the coils of the suture cutter. In this way, once the distal portion of the suture or sutures has been removed, only a relatively short portion of suture ends, or tails, extend beyond the suture lock, and the remaining suture portions that extend to the leaflet and to the ventricular anchor are non-meltable sutures and remain securely clamped in the suture lock.

The meltable suture component(s) can include, but are not limited to, suitable melting compositions including polyolefin, polyethylene, ultrahigh molecular weight polyethylene, polypropylene, polyester, polyamide, polyglycolide/L-lactide, polyethylene terephthalate, silicone, collagen or other amino acid protein and a combination thereof. In some embodiments, a portion of the suture is meltable using any one of the previously described polymers as the meltable portion of the suture or meltable zone. The non-meltable portion of the suture can be PTFE or ePTFE.

Suture Lock Guide

Figure 48:
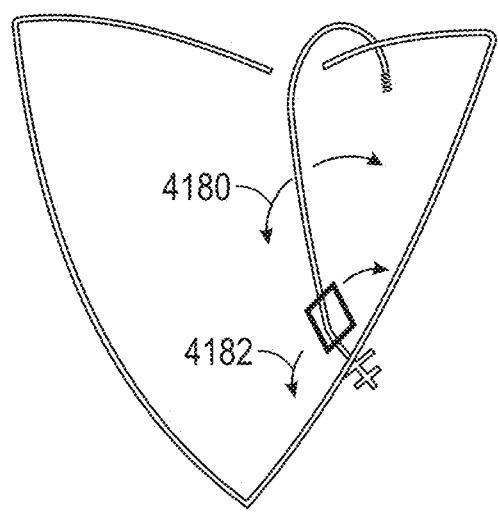
FIG. 48 depicts motion of a pledget suture and a suture lock in certain transcatheter mitral chordal repair systems, according to aspects of the present disclosure, in accordance with an embodiment.

The embodiments discussed above can provide effective mechanisms for transcatheter mitral chordal repair, e.g., implanting and effecting prosthetic chords. Embodiments discussed below build on many of these concepts to provide additional advantages. For example, the normal cardiac functions of the heart can cause mitral chordal repair systems to undergo cyclic motion and loading. In particular, a suture lock or other components (e.g., the suture) can oscillate or otherwise move within the ventricle as a result of the heart's normal compression cycles. This motion is generally shown in FIG. 48, where the arrows 4180, 4182 generally indicate motion of a suture and motion of a suture lock, respectively.

Figure 49:
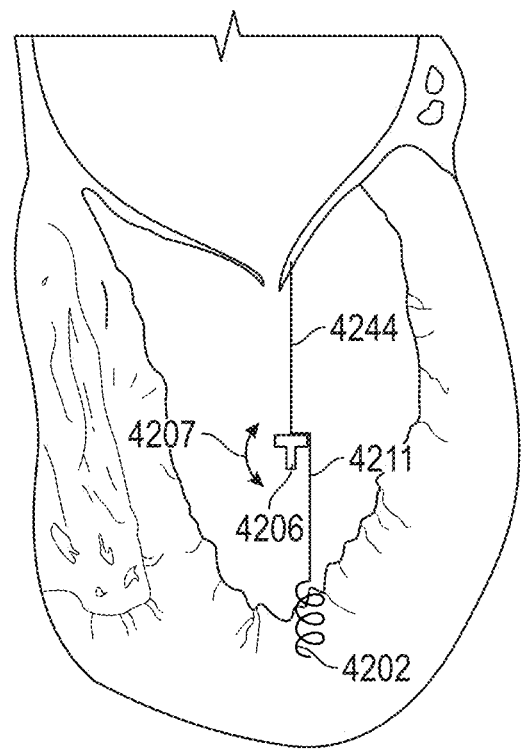
FIGS. 49 and 50 illustrate movement of sutures and a suture lock, according to aspects of the present disclosure, in accordance with an embodiment.

The oscillatory motion of the sutures and the suture lock can contribute to excessive wear on the suture, particularly at their junctures with the suture lock. The resulting wear could eventually result in the premature deterioration and failure of the prosthetic chord. In particular, in some systems the sutures pass through the suture lock, e.g., along its longitudinal direction. The sutures connecting the mitral leaflet and the anchor extend from the one end of the suture. The weight of the suture lock will pull the other end of the suture lock down slightly relative to the true orthogonal, and this angular movement can force the sutures against the suture lock. If the suture lock includes relatively sharp angles, those angles can introduce shearing forces that can cause the sutures to prematurely break. For example, FIG. 49 illustrates a suture lock 4206 whose orientation results in the suture 4211 located against a sharp angle on the suture lock 4206. During movement of the suture 4211 and suture lock 4206, the sharp angle introduces shearing forces on the suture 4211. Suture 4244 can be subjected to similar shearing forces. These shearing forces can be amplified by rotational movement of the suture lock 4206, as represented by arrow 4207.

Figure 50:
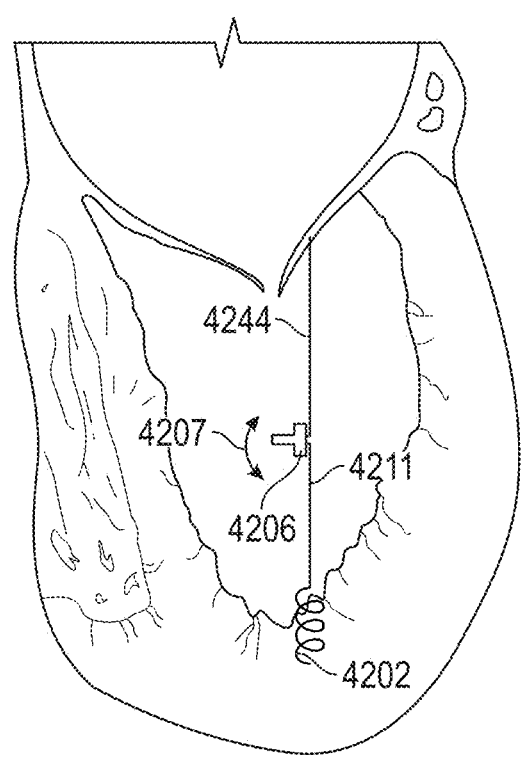

Furthermore, increasing tension on the sutures tends to rotate the suture lock into an orientation that is somewhat orthogonal to the sutures, as shown in, e.g., FIG. 50. This movement, in addition to the mass and resulting inertia of the suture lock during other movements, can add a high-impulse force to the sutures, e.g., as part of a "whipping" motion. In some situations, this could cause suture materials to shatter due to their visco-elastic characteristics. Accordingly, movement of the suture lock (e.g., relative to the anchor) can be an additional source of potential failure for mitral chordal repair systems.

Furthermore, the changing tension on the sutures can alter the length of the prosthetic chord, which can negatively impact the effectiveness of the prosthetic chord, e.g., at resolving MR. For example, and as shown in FIGS. 49 and 50 the suture lock 4206 assumes a particular orientation relative to the sutures 4211, 4244 when tension on the sutures is lowered or removed. In this situation, the prosthetic chord has a particular length, e.g., as measured between the leaflet (where the suture 4244 is coupled to the leaflet) and the ventricular tissue (where the suture 4211 is secured to the anchor 4202). In effect, part of the suture (e.g., suture 4211) is wound around the suture lock 4206 and does not contribute to the overall length of the prosthetic chord. However, when tension is applied to the sutures, that tension will rotate the suture lock 4206, as shown in FIG. 50. As a result, the portion of the suture 4211 previously wound around the suture lock 4206 is pulled away from the suture lock 4206, resulting in a corresponding increase in the length of the prosthetic chord. In some situations, this increase is around 0.10 mm to 0.30 mm, though in some cases it can be as much as 0.50 mm. In some embodiments, the amount of change will depend on the width of the suture lock 4206 and the angle of rotation of the suture lock 4206. In some situations, these changes in length with reduce the efficacy of the prosthetic chord, causing the physician to readjust the prosthetic chord or necessitating reinstallation of the prosthetic chord.

Embodiments of the present disclosure are designed to mitigate the effects of some or all of these issues, as well as providing additional advantages that improve the efficacy of the prosthetic chord and/or increase ease of implementation. For example, some embodiments include a transcatheter mitral chordal repair system designed to reduce or eliminate suture movement relative to the suture lock and other system components. Certain embodiments further serve to decrease the amount of unrestrained suture within the ventricle. Some embodiments provide for a prosthetic chord that incorporates a prosthetic papillary muscle, which can reduce the whipping effect.

Certain embodiments are designed to limit or eliminate movement of the suture lock relative to the anchor. These embodiments can also limit or eliminate movement of the sutures relative to the anchor, at least at a location near the anchor. As a result, these embodiments reduce wear on the sutures and promote longer lifetime for the mitral chordal repair system.

In some embodiments, the transcatheter mitral chordal repair system creates a prosthetic papillary construct using a retaining member also referred to herein as a suture lock guide (e.g., a socket or sleeve) that constrains motion of the suture lock. An example of such a suture lock guide was described above with reference to FIGS. 2A and 2B and was in the form of a tubular sleeve 78. Motion of the sutures relative to the suture lock can also constrained near the suture lock, which reduces the wear on the sutures. In some embodiments, the transcatheter mitral chordal repair system includes an suture lock guide also referred to herein as an anchor socket that restricts motion of the suture lock, relative to the anchor, as well as motion of the sutures relative to the suture lock.

Embodiments discussed herein can provide prosthetic systems designed to maintain integrity through about 800 million cycles, or about 20 years. In certain example embodiments, embodiments discussed herein can provide prosthetic systems designed to maintain integrity through 800 million cycles, or 20 years. Disclosed are arrangements prosthetic chords that can remain for a minimum of 400 million cycles, or about 10 years. In certain example embodiments, disclosed are arrangements prosthetic chords that can remain for a minimum of 400 million cycles, or 10 years. These prosthetic chords will perform under the range of typical situations and environments without excessive structural damage and/or functional impairment after 400 million cycles, i.e., without exhibiting holes, tears, gross delamination, severing, fraying, incomplete leaflet coaptation, excessive regurgitation, and the like.

Figure 51:
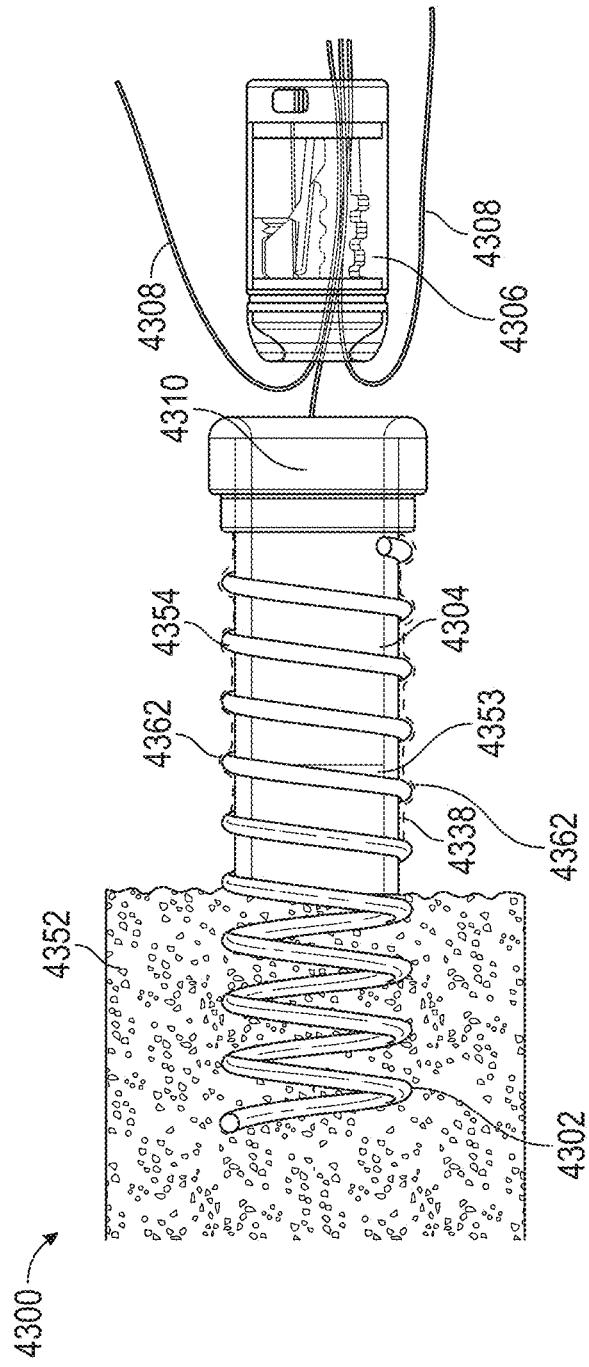
FIG. 51 illustrates an anchor, retaining member, and suture lock of a transcatheter mitral chordal repair system in which an upper portion of the anchor extends along a portion of the outer surface of the retaining member, according to aspects of the present disclosure, in accordance with an embodiment.
Figure 52:
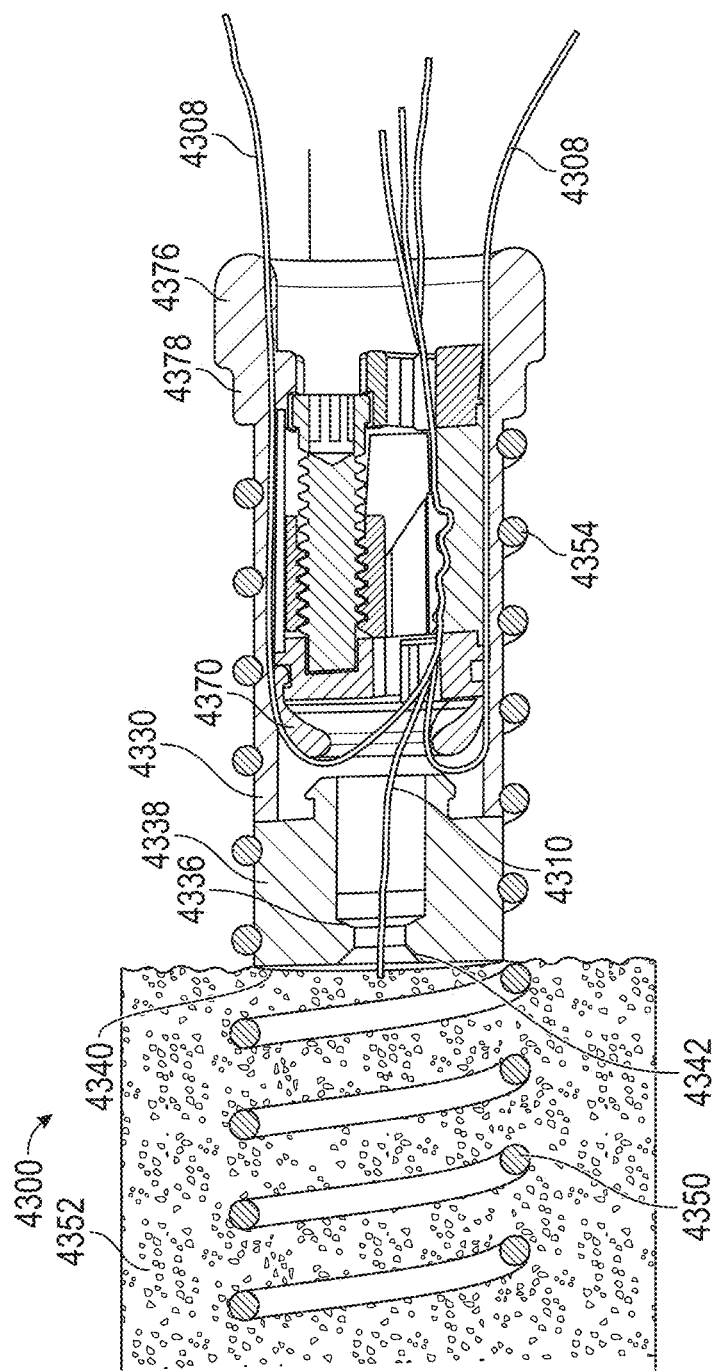
FIG. 52 illustrates a cut-away view of the transcatheter mitral chordal repair system of FIG. 51, with the suture lock located within the retaining member, in accordance with an embodiment.

FIGS. 51 and 52 illustrate components of a transcatheter mitral chordal repair system 4300, according to some embodiments of the present disclosure. That system 300 provides one or more prosthetic chords using one or more sutures or tethers deployed into a beating heart without extracorporeal circulation using a transcatheter delivery system. These embodiments can reduce wear on anchoring sutures or tethers over time by using a retaining member or restraining member, which in some embodiments includes a stent-like or stent graft-like socket anchored to a securing device or anchor located on the epicardium. The delivery systems and techniques discussed above and/or in PCT/US2017/069046 and PCT/US2019/021480, which are incorporated by reference herein, may be employed to deliver the components of system 4300.

FIGS. 51 and 52 illustrate an anchor 4302, a retaining member 4304, and a suture lock 3406. In several of the embodiments illustrated herein, the retaining member 4304 is a socket or sleeve which can be, in certain aspects of the disclosure, similar to the sleeve or socket 78 descried above with respect to FIGS. 2A and 2B. In other embodiments, the retaining member may be a pin, a hook, a clasp, a claw, a catch, a buckle, a suture, or the like. The anchor 4302 may be—in part or in full—any of the anchors disclosed above and/or in PCT/US2017/069046 or PCT/US2019/021480. Also shown in FIGS. 51 and 52 are sutures 4308 and an anchor suture 4310. While two sutures 4308 are shown in FIGS. 51 and 52, only one suture or more than two sutures may be used. The sutures 4308 can be coupled to one or more leaflets of the mitral valve, e.g., using pledgets for example using the systems or techniques described above and/or in PCT/US2017/069046 or PCT/US2019/021480. Accordingly, the sutures 4308 may be referred to as pledget sutures. The anchor 4302 can engage the ventricular tissue, and the retaining member 4304 can receive and secure the suture lock 4306 and the sutures 4308, 4310.

The suture lock guide or retaining member 4304, in some embodiments, restricts motion of the sutures 4308 and/or the suture lock 4306 while facilitating installation, adjustment, and eventually operation of the sutures 4308 as part of a prosthetic chord. For example, in some embodiments, the retaining member (also referred to herein as suture lock guide) 4304 is configured to selectively couple and decouple with the suture lock 4306. When coupled to the suture lock 4306, the retaining member 4304 may provide securing forces strong enough to prevent slippage during cardiac cycles (e.g., with non-limiting forces ranging up to approximately 1 N, 1.5 N, 2.0 N, 2.5 N, or 3 N) yet still enable a physician to pull on the sutures 4308 to tighten or loosen the sutures 4308 without displacing the suture lock 4306. In other embodiments, the retaining member 4304 is designed to secure the sutures 4308 and the suture lock 4306, such that any adjustment to the sutures will require the physician to remove the suture lock 4306 from the retaining member 4304, adjust the sutures 4308, and then re-insert the suture lock 4306 back into the retaining member 4304. Removing the suture lock from the retaining member 4304 may in certain instances requires larger forces, e.g., forces above approximately 6 N to approximately 9 N, or even in excess of 10 N in some embodiments. In other words, in some non-limiting embodiments the retaining member 4304 is configured to exert retaining forces on the suture lock that resist forces between approximately 4 N to at least 10 N, including forces of approximately 4.5 N, 5 N. 5.5 N, 6 N, 6.5 N, 7 N, 7.5 N, 8 N, 8.5 N, 9 N, 9.5 N, 10 N, 10.5 N, or 11 N.

As a result of the retaining member 4304, the suture lock 4306 can maintain a positional relationship with the anchor 4302. For example, as the heart tissue moves during cardiac cycles, the retaining member 4304 will resist displacing forces exerted on the suture lock 4306 (e.g., via the sutures 4308). In some embodiments, the retaining member 4304 transfers forces exerted on the suture lock 4306 to the anchor 4302. The displacing forces may range up to approximately 1 N, though in some situations those forces may be around 1.5 N or up to approximately 3 N.

In some embodiments, a retaining member 4304 is a socket formed by inverting a vascular graft tube. The retaining member 4304 is designed to be radially compliable to permit the suture lock 4306 to enter the retaining member 4304 while providing constraining forces. The retaining member 4304 can also be also axially stiff and wear resistant. Axial stiffness enables the suture lock 4306 to enter the retaining member 4304 without buckling. Wear resistance can be minimized with a PTFE-PTFE interaction.

For example, in the embodiments shown in FIGS. 51 and 52, the retaining member 4304 includes an interior surface 4330 defining a chamber that receives and secures the suture lock 4306 and/or the sutures 4308. In some embodiments, the retaining member 4304 is made of a material that is flexible enough to accommodate the suture lock 4306 and even permit adjustment of the sutures 4308 relative to suture lock 4306 after the suture lock 4306 is inserted into the retaining member 4304. In some embodiments, the retaining member 4304 is radially compliable to permit the suture lock 4306 to enter and couple with the retaining member 4304. The retaining member 4304 may couple with the suture lock 4306 using an interference fit or the like.

In some embodiments, the retaining member 4304 couples with an exterior surface of the suture lock 4306, e.g., a portion of the exterior surface located between a proximal end and a distal end of the suture lock 4306. For example, the retaining member 4304 contacts opposite sides of the suture lock 4306 to couple with the suture lock 4306. In other embodiments, the retaining member 4304 contacts the suture lock 4306 at three or more points to constrain movement of the suture lock 4306 relative to the anchor 4302. In FIGS. 51 and 52, the retaining member 4304 and the suture lock 4306 are both cylindrically shaped, and the retaining member 4304 engages the suture lock 4306 about or around its circumferential perimeter. In FIGS. 51 and 52 the engaging contact between the retaining member 4304 and the suture lock 4304 extend longitudinally along the circumferential surface of the suture lock. In some embodiments, the engaging contact can extend over half of the longitudinal extent of the suture lock. In other embodiments, the engaging contact can extend over a percentage of the longitudinal extent of the suture lock ranging from approximately 20% to approximately 98%. In other embodiments, that range may be more limited, e.g., approximately 40% to approximately 80%, approximately 50% to approximately 70%, or combinations of the ranges discussed herein (as well as any subranges with the ranges explicitly mentioned as examples).

FIGS. 51 and 52 also illustrate a support member 4354 or support coil that can reinforce the material of the retaining member 4304 as the retaining member 4304 secures the suture lock 4306 and the sutures 4308. In some embodiments, the anchor 4302 and the support member 4354 are two separate structures that may be integrated, while in other embodiments the anchor 4302 and the support member 4354 are unitarily formed of a single material. The support member 4354 may extend along a length of the retaining member 4304 so as to terminate at a location that is substantially aligned with a distal surface of the suture lock 4306 when fully inserted into the socket 4304. In other embodiments, the support member 4354 may extend along a length of the retaining member 4304 so as to terminate at a location that is substantially aligned with an upper portion of the suture lock 4306 but located below (or proximal of) the distal surface of the suture lock 4306. The support member 4354 contacts an outer surface of the retaining member 4304. A bonding material 4362 is placed along the support member 4354 and the exposed outer surface of the retaining member 4304. This bonding material 4362 may also contact the exposed outer surface of an anchor hub 4338.

In some embodiments, the support member 4354 provides axial rigidity to prevent folding as the suture lock 4306 enters the retaining member 4304. For example, in FIGS. 51 and 52, the support member 4354 is a support coil that resists longitudinal forces exerted on the retaining member 4304, e.g., by the suture lock 4306 as it is pressed into the retaining member 4304. This additional rigidity holds the retaining member 4304 steady, thereby increasing ease of installation. In other embodiments, the retaining member 4304 may be formed of other materials and may be formed in other configurations. For example, the support member 4304 may be formed of multiple metal strips longitudinally extending along the outer surface of the retaining member 4304 or may be one or more cylindrical cuffs longitudinally spaced along the other surface of the retaining member 4304. In some embodiments, the retaining member 4354 is formed of nitinol tines or similar material.

The support member 4354, in some embodiments, provides additional securing forces that maintain the suture lock 4306 and sutures 4308 within the retaining member 4304. For example, in FIGS. 51 and 52, the support member 4354 is a support coil. In some embodiments, as the suture lock 4306 is pressed into the retaining member 4304, the support coil linearly compresses, and its inner diameter increases to accommodate the suture lock 4306. The compressive forces of the support coil (e.g., as it recoils back towards its original configuration and smaller inner diameter) increases the frictional forces between the retaining member 4304 and the suture lock 4306. Furthermore, in some embodiments, the support coil is configured to linearly extend in response to forces pulling the suture lock 4306 from the retaining member 4304. This will further decrease the inner diameter of the support coil, augmenting the frictional forces between the retaining member 4304 and the suture lock 4306.

In some embodiments, the support member 4354 terminates at an intermediate portion of the retaining member 4304 below a distal portion of the retaining member 4304. In this manner, the distal portion of the retaining member 304 above the support member 4354 exerts relatively smaller forces on the suture lock 4306 and sutures 4308, compared to the combination of the retaining member 4304 and support member 4354. With these relatively smaller forces, the physician can adjust the tension or length of the sutures 4308 without displacing the suture lock 306 from the retaining member 4304.

Stated differently, in some embodiments the retaining member 4304 (alone or in combination with the support member 4354) provide sufficient forces to retain the suture lock 4306 during cardiac cycles (e.g., forces from approximately 0 N to approximately 4 N). Forces exerted on the sutures 4308 by the physician (e.g., pulling the proximal ends of the sutures 4308) and/or leaflet (e.g., pulling the distal ends of the sutures 4308) allow the physician to adjust the sutures 4308 relative to the suture lock 4306, while the suture lock 4306 remains secure within the retaining member 4304, in order to adjust the length of the sutures 4308 between the suture lock 4306 and the leaflet. The magnitude of the forces required to move the sutures 4308 in some embodiments range from 1 N to 2 N. Thus, the retaining member 4304 (alone or in combination with the support member 4354) secures the suture lock 4306 relative to the anchor 4302 during adjustment of the sutures 4308. One the suture lock 4306 engages the sutures 4308 (as described below), the retaining member 4304 secures the suture lock 4306, which secures the sutures 4308 as part of the prosthetic mitral chord.

Still referring to the embodiments described with reference to FIGS. 51 and 52, the retaining member 4304 is a generally cylindrical structure. The retaining member 4304 may be a stent or stent-graft structure formed (in whole or in part) of ePTFE. The materials forming the retaining member 4304 can promote tissue ingrowth to further secure the anchor 4302 and/or the prosthetic chord. The materials forming the retaining member 4304 can include a film microstructure in which the fibrillar orientation is in a direction substantially parallel the longitudinal axis of the retaining member 4304. In this manner, any longitudinal motion of sutures 4308, (e.g., ePTFE sutures) will be in line with the fibrillar orientation to further reduce friction and wear on the sutures.

Stated differently, in some embodiments, the retaining member 4304 is made from an ePTFE graft, elastomer, other polymer, or combination of these materials. For example, in some embodiments the retaining member 4304 is constructed from ePTFE stretch graft and may be densified to enhance column strength. The retaining member 4304 in some embodiments is partially or fully bio-resorbable or bio-absorbable and provides temporary fixation until, e.g., biological fibrous adhesion between the tissues and other components. In some embodiments, the retaining member 4304 includes a mesh designed to enhance biocompatibility and fibrosis following implantation. All or part of the surface of the retaining member 4304 may be configured to promote tissue growth onto and/or through its surface. In one example, this growth is achieved by providing a relatively rough and/or porous surface. Another example is to have one or multiple holes drilled through the material of the retaining member 4304, allowing scar tissue fibrocytes to grow through these holes and thereby add strength to the fixation. Additionally, biological coatings of the types known in the art can be included on the surface of the retaining member 4304 to promote healing and tissue growth.

The suture lock 4306 can be secured within the retaining member 4304, where it is aligned coaxially with the anchor 4302. This configuration can minimize or eliminate the relative motion of the suture lock 4306 with respect to the sutures 4308, at least within the retaining member 4304.

This configuration can also minimize or eliminate movement of the sutures 4308 within the retaining member 4304 relative to the suture lock 4306 and the anchor 4302.

In some embodiments, the length of the support member 4354 ranges from approximately 0.5 mm to 3.0 mm. In other embodiments. In some embodiments, the length of the support member 4354 varies from a quarter of the length of the retaining member 4304 up to the full length of the retaining member 4304.

Other embodiments (e.g., embodiments shown in FIGS. 2A, 2B, 55) do not include a support member 4354. Some of these embodiments provide varying restraining forces through other mechanisms, including by varying the materials and/or surface treatments used to construct different portions of the socket or by varying the size of the socket at different locations. Still other embodiments make use of external tools that expand an upper portion of the socket or otherwise reduce the restraining forces on the suture lock and sutures at that upper portion.

As can be seen in FIG. 52, the sutures 4308 can be located between an outer surface of the suture lock 4306 and an inner surface of the retaining member 4304. In some embodiments, these surfaces (in whole or in part) are designed to facilitate securement of the sutures 4308, for example, providing surfaces with higher coefficients of friction. In other embodiments, these surfaces (in whole or in part) are designed to facilitate easy adjustment of the sutures 4308, providing surfaces with lower coefficients of friction. One or both of these surfaces may be resilient to help secure the sutures 4308 while enabling adjustment.

Securing the sutures 4308 between the suture lock 4306 and the retaining member 4304 can provide additional advantages. For example, the suture lock 4304 and the retaining member 4304 can maintain tension on distal portions of the sutures (e.g., portions extending from the suture lock 4306 towards the leaflets) even when tension on proximal portions of the sutures (e.g., portions extending from the socket 4306 towards the physician or proximal end of the catheter) changes or is eliminated. As a result, once the suture lock 4306 is placed within the retaining member 4304, thereby securing the sutures 4308, any tension change in the proximal portions of the sutures (e.g., if the physician accidentally bumps the catheters) will not substantially affect tension in the distal portions of the sutures 4308. Accordingly, physicians need not maintain each suture 4308 in tension during the operation. Furthermore, in some embodiments, the suture lock 4306 and retaining member 4304 can be used to maintain tension in a distal portion of one suture during adjustment of another suture.

As shown in FIG. 52, in some embodiments the retaining member 4304 includes an upper enlarged portion 4376 and a lower enlarged portion 4378. These enlarged portions 4376, 4378 can provide additional axial rigidity to prevent folding or buckling as the suture lock 4306 is pushed into the retaining member 4304. In addition, the enlarged upper portion 4376 could incorporate a band that increases rigidity and provides a radiopaque marker. In some embodiments, the upper enlarged portion 4376 includes an outer surface located further out (e.g., along a radial direction) than a lower portion of the socket. The upper enlarged portion 4376 can include an inner surface that is located further out (e.g., along a radial direction) than a lower portion of the retaining member 4304. For example, the upper enlarged portion 4376 could form a tapered shape (e.g., a funnel) to assist in receiving the suture lock 4306.

The sutures 4308, 4310 may be formed from surgical-grade materials such as biocompatible polymer suture material. Examples of such material include 2-0 ePTFE (polytetrafluoroethylene) or 2-0 polypropylene. In some embodiments the sutures 4308, 4310 are inelastic. In other embodiments, the sutures 4308, 4310 can be partially or fully elastic. The sutures 4308, 4310 in some embodiments are be partially or fully bio-resorbable or bio-absorbable and provide temporary fixation until, e.g., biological fibrous adhesion between the tissues and other components. Thus, the sutures 4308, 4310 may be formed from a biocompatible material (e.g., nitinol, ePTFE, PTFE, PET, or polyester, nylon, Silicone, collagen or other amino acid protein, stainless steel, cobalt chrome, combinations of these, or the like).

FIGS. 51 and 52 illustrate an anchor hub 4338 that can contact the heart tissue 4352 and can serve as a stopping point for the anchor 4302 as it screws into the heart tissue. The anchor hub 4338 can include an upper surface that, in some embodiments, couples to a bushing 4353 (as discussed below). The anchor 4302 and the anchor hub 4338 may be joined together through mechanical means, such as a frictional fit, by chemical means, or through other means. The anchor hub 4338 can transfer forces exerted on the retaining member 4304 (e.g., via the sutures 4308) into the heart tissue 4252 via the anchor 4302. In this manner, the anchor hub 4338 works with the retaining member 4304 to dampen oscillatory motion created by the heart's movements.

In some embodiments, the proximal surface of the anchor hub 4338 contacts the suture lock 4306 (e.g., the nose portion of the suture lock 4306) and the sutures 4308. The anchor hub 4338 (or at least its proximal surface) may be formed of a material designed to augment frictional forces to secure the sutures 4308 located between the anchor hub 4338 and the suture lock 4306 or may be formed of a material that reduces frictional forces to facilitate adjustment of the sutures 4308 located between the anchor hub 4338 and the suture lock 4306. The anchor hub 4338 could be formed of PFA, silicone material, PTFE material, ePTFE material, thermoplastics, and the like (or combinations thereof). The anchor hub 4338, in some embodiments, is partially or fully formed of metal, stainless steel or titanium, or potentially a rigid plastic like PEEK, or other sufficiently rigid materials. The bushing, or proximal surface of the anchor hub 4338 that interacts with the suture lock, could be made from PFA, silicone material, PTFE material, ePTFE material, thermoplastics, and the like (or combinations thereof).

In some embodiments, a bushing 4353 is located adjacent the anchor hub 4338 to cushion the suture lock 4306. This bushing may be formed of PFA or another polymer. The bushing provides a surface that contacts the sutures 4308 and, in combination with the nose portion of the suture lock 4306, helps to secure the sutures 4308. In some embodiments, the bushing facilitates suture adjustment due to the interactions of the PFA material of the bushing and the ePTFE material of the sutures 4308. Bushing may also provide a surface that diminishes wear on the sutures, particularly if the anchor hub 4338 would otherwise present a rougher surface (e.g., due to the materials and/or surfaces of the anchor hub 4338) against the sutures 4308. The bushing 4353, or the proximal surface of the anchor hub 4338 that interacts with the suture lock, could be made from PFA, silicone material, PTFE material, ePTFE material, thermoplastics, and the like.

In some embodiments, the diameter of the hub (e.g., hub 4338) corresponds to the minor or inner diameter of the support member 4354. Depending on how it is attached, the length of the hub 4338 is sufficiently long to allow the support member 4354 to be attached to the hub 4338 and to have a driver engage with the hub 4338. The geometry where the retaining member 4304 is attached to the hub 4338 is smaller than the minor diameter of the support member 4354. The outer diameter of the retaining member 4304 is smaller than the major diameter of the support member 4354 in some embodiments.

As shown in FIG. 52, the anchor suture 4310 can pass through a channel 4336 of the anchor hub 4338 and can be secured near the bottom surface 4340 of the anchor hub 4338. In some embodiments, the channel 4336 includes a bottleneck portion 4342 that secures the anchor suture 4310 (e.g., by trapping a knot formed at the end of the anchor suture 4310 below the bottleneck portion 4342). In other embodiments, the anchor suture 4310 and the anchor hub 4338 be joined together through mechanical means, such as a frictional fit, by chemical means, or through other similar means.

The suture lock 4306 may incorporate features of the suture locks disclosed herein and/or PCT/US2017/069046 and PCT/US2019/021480. The suture lock 4306 can include a cylindrical outer surface that corresponds to the cylindrical chamber of the retaining member 4304 to provide a frictional or interference fit. The suture lock 4306 can include a locking mechanism (e.g., an internal locking mechanism) that selectively secures the anchor suture 4310 and the sutures 4308. The illustrated suture lock 4306 includes a nose portion 4370 that presents a rounded surface on which the sutures are pressed when tensioned. In this manner, the suture lock 4306 can avoid sharp edges that could fray the sutures 4308. In some embodiments, the nose portion 4370 is formed of, e.g., PFA, or another material designed to reduce wear on the sutures.

The suture lock 4306 can travel down the anchor suture 4310 until it enters the cylindrical chamber of the retaining member 4304. The retaining member 4304 can provide some radial resistance to the suture lock 4306 but can be radially compliant to receive the suture lock 4306. In some embodiments, the sutures 4308 can be adjusted, even when the suture lock 4306 is bottomed out (i.e., passes down to the end of the socket 4304, which could include pressing against the bushing 4353). For example, the sutures 4308 are most easily adjusted while the suture lock 4306 is outside of the retaining member 4304. However, even after the suture lock 4306 has entered the retaining member 4304, the sutures 4308 can still be adjusted. When the suture lock 4306 bottoms out in some embodiments, the sutures 4308 are sandwiched between the PFA bushing 4353 and the PFA nose 4370 of the suture lock 4306. At this stage, the sutures 4308 can still be adjusted in some embodiments, though with greater resistance. For example, the material of the suture lock nose 4370 and the bushing 4353 may reduce friction for easier adjustment. In other embodiments, the bushing 4353 and the nose 4370 are designed to secure the sutures and prevent further movement.

In some of the embodiments discussed above, the anchor 4302 is pre-assembled with the retaining member 4304. In other words, the anchor 4302 and the retaining member 4304 are coupled together outside of the patient. The suture lock 4306 is then coupled to the retaining member 4304 (e.g., via an interference or frictional fit) inside of the patient. In other embodiments, the retaining member 4304 and suture lock 4306 are coupled together outside the patient. The retaining member 4304 and the anchor 4302 are then coupled together (e.g., via an interference or frictional fit) inside of the patient.

In some embodiments, the retaining member 4304 is configured to expand. For example, in some embodiments the retaining member 4304 is formed of a resilient material that expands as the suture lock 4306 is pressed down into the retaining member 4304 and will reseal around the suture lock 4306 to help secure it in place. In other embodiments, the retaining member 4304 has an expanded configuration and a retracted position. The retaining member 4304 can be delivered in its expanded configuration and, once the suture lock 4306 is in place, the retaining member 4304 collapses down to its retracted position to secure the suture lock 4306 in place.

Figure 53:
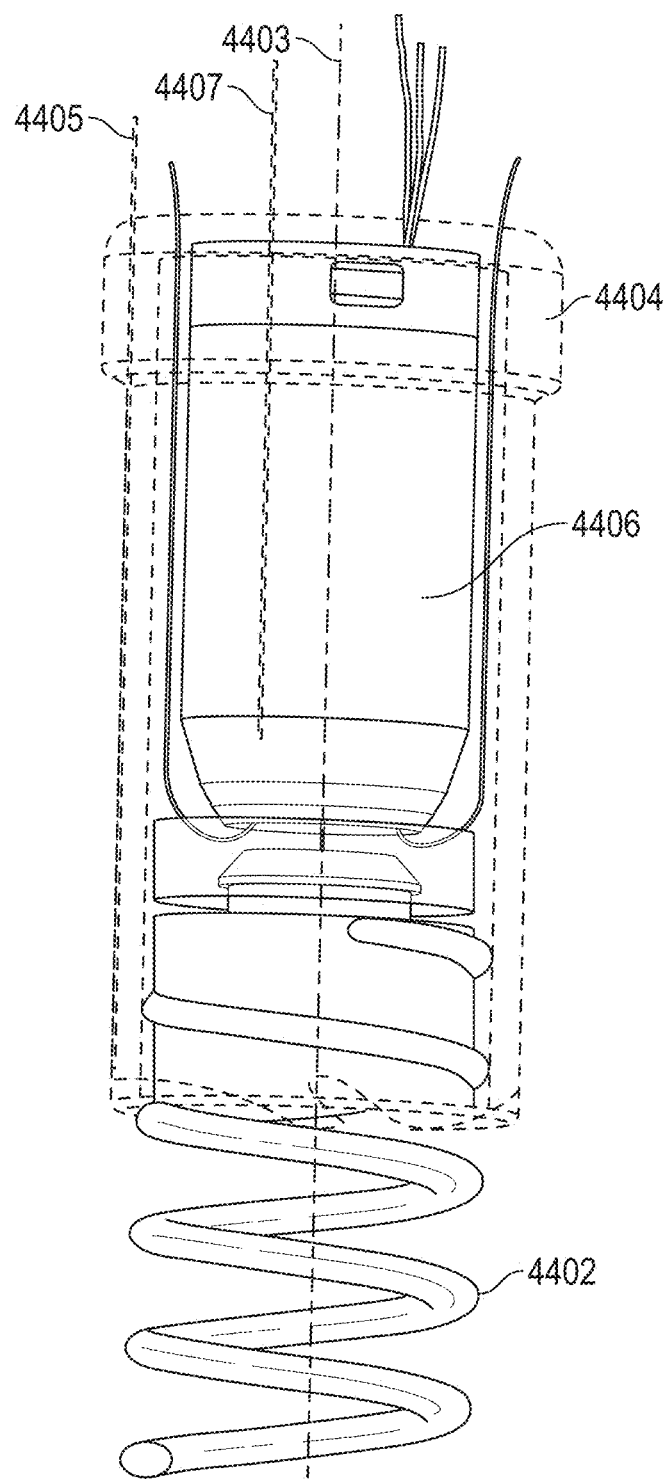
FIG. 53 illustrates an orientation of a suture lock, retaining member, and anchor according to aspects of the present disclosure, in accordance with an embodiment.

In some embodiments, and as shown in FIG. 53, an anchor 4402 defines a longitudinal line 4403, and the retaining member 4404 or restraining member (e.g., socket) constrains movement of the suture lock 4406 relative to the anchor 4402 in a direction orthogonal to the longitudinal line 4403 defined by the anchor 4402. In some embodiments, the retaining member 4404 constrains movement of the suture lock 4406 relative to the anchor 4402 in a plane orthogonal to the longitudinal line 4403. In some embodiments, the retaining member or restraining member (e.g., socket 4404) constrains movement of the suture lock relative to the anchor along the longitudinal line 4403.

As also seen in FIG. 53, the restraining member 4404 substantially aligns a longitudinal line 4403 defined by the anchor 4402 and/or a longitudinal line 4405 defined by the restraining member 4404 with a longitudinal line 4407 defined by the suture lock 4406. In some embodiments, the retaining member 4404 secures the suture lock 4406 in a co-axial relationship with the anchor 4402 and/or the retaining member 4404. In some embodiments, the longitudinal lines defined by the anchor 4402, retaining member 4404, and/or suture lock 4406 extends to a leaflet of the mitral valve.

Figure 54:
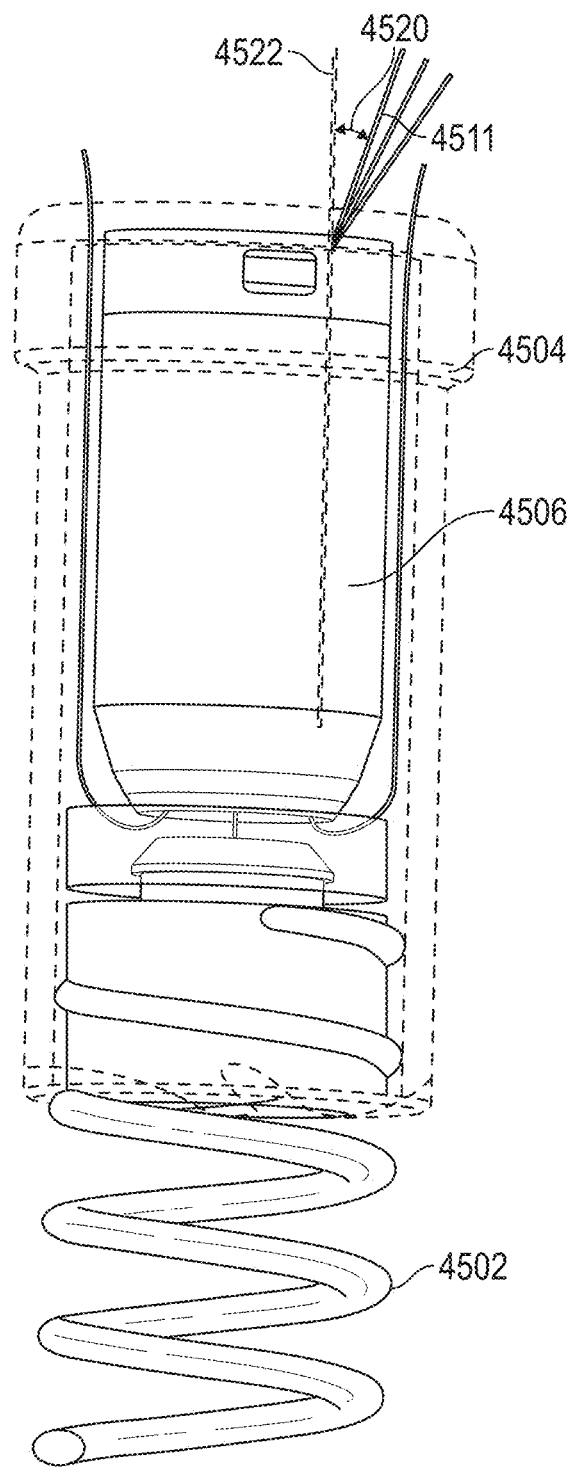
FIG. 54 illustrates an orientation of a suture lock and suture, according to embodiments of the present disclosure, in accordance with an embodiment.

In some embodiments, and as shown in FIG. 54, the retaining member 4504 constrains angular movement of a suture (suture 4511) relative to the suture lock 4506. As discussed above with respect to FIGS. 49 and 50, in some embodiments the suture lock rotates in response to forces during the cardiac cycle, such that the angles formed by the portions of the sutures extending from the suture lock and towards the leaflets, relative to a longitudinal line defined by the suture lock, will vary widely. The location of the suture lock above the anchor and closer to the leaflets also contributes to the angular movement. However, as shown in FIG. 54, the retaining member 4504, by securing the suture lock 4506 in a particular orientation, restrains angular movement of the suture 4511. For example, in some embodiments, the angle 4520 formed between the portion of a suture 4511 extending from the suture lock 4506 towards the leaflet and a longitudinal line 4522 of the suture lock 4506 is less than 45°. In some embodiments, angle 4520 can range from approximately −45° to +45°, which may also be understood as approximately 0° to 45° in two opposite directions. This angle 4520 may be formed in any plane that includes that portion of the suture 4511 and the longitudinal line 4522 of the suture lock.

While the suture 4511 will move during cardiac cycles, the retaining member 4504 can constrains angular movement (changes in angle 4520) to less than 90°. In some embodiments, the angular change is less than 45°, while in other embodiments the angular change can be less than approximately 40°, 35°, 30°, 25°, 20°, 15°, 10°, 8° or even less than approximately 5°.

Method for measuring angular changes between ventricular anchor and suture lock

The angular change between the anchor and suture lock can be determined, for example, with the following steps:

1. Fixture a ventricular anchor into one side of a tensile test machine. This can be done by simulating ventricular anatomy such as a silicone pad or by clamping into standard tensile test machine clamping jaws.
2. Fixture a prosthetic chordae into the other side of the tensile test machine. This can be done by simulating leaflet anatomy such as a silicone pad or by clamping into standard tensile test machine clamping jaws.
3. Couple the ventricular anchor and the prosthetic chordae together using a suture lock.
4. Load the system with the ventricular anchor, prosthetic chordae, and suture lock in tension to a minimum of 2 N.
5. Measure the angle between the axis of the suture lock, or any linear feature of the suture lock, and the axis of the ventricular anchor, or any linear feature of the ventricular anchor (Angle 1).
6. Unload the system with the ventricular anchor, prosthetic chordae, and suture lock to a load less than ON or a load equivalent to the hanging static weight of system on the load cell.
7. Measure the angle between the axis of the suture lock, or any linear feature of the suture lock, and the axis of the ventricular anchor, or any linear feature of the ventricular anchor (Angle 2).
8. Calculate the difference between Angle 1 and Angle 2.

During installation of the prosthetic chord, the anchor and retaining member can be delivered (e.g., via a catheter) and the anchor is implanted into the ventricular tissue. An anchor suture extends from the anchor. Sutures (e.g., pledget sutures) are then coupled to one or more of the mitral valve leaflets. A suture lock advances over the anchor suture and the pledget sutures. In some embodiments, the physician can adjust the location of the suture lock relative to the pledget sutures so that length of the pledget sutures between the suture lock and the leaflet(s) can ensure that the prosthetic chord can operate adequately (e.g., to reduce and/or eliminate MR). For example, the physician can pull on a proximal portion of one of the sutures to decrease the amount of suture located between the suture lock and the mitral valve leaflet.

However, in certain embodiments the suture lock can be unrestrained. As a result, adjustment of a suture (e.g., pulling on the suture) can move the suture lock upwards, which impacts the tension on the portions of the sutures between the suture lock and the mitral valve. This issue can be exacerbated when multiple sutures are used with the suture lock. Adjusting one of the sutures can raise the suture lock, undoing any prior adjustments of another suture.

For example, the suture can be attached to a leaflet and passes through a suture lock, which functions as a moveable pulley for the suture. Specifically, when a physician pulls on the end portion of the suture located outside of the body, this will move the suture. However, pulling the proximal end portion of the suture can move the suture lock upwards, such that the physician's movement of the suture external to the body will not have a one-to-one correspondence with the movement of the suture between the suture lock and the leaflet.

This issue can be exacerbated when multiple sutures pass through a single suture lock. For example, a physician can adjust a first suture to the correct length. However, once the physician begins to adjust a second suture, such movement will displace the suture lock, which could negatively impact the first suture and require the physician to readjust the first suture. Of course, this could then negatively impact the second suture, leading to additional needed adjustments.

Additional complications arise when the physician cuts a suture after engaging the suture lock. Prior to cutting the suture, the physician maintains tension on the suture, which maintains the suture lock in a higher position. Cutting the suture (and/or disconnecting the suture lock from the catheter) will release this tension and the suture lock can move downward, which can impact the effectiveness of the suture as a prosthetic-chord. That the physician should maintain tension on the suture (e.g., on a first suture while adjusting a second suture) creates additional complications. For example, any inadvertent movement of the catheter (e.g., an accidental bump) could cause the suture lock to move and change the length of the suture between the suture lock and the tissue (e.g., the leaflet).

Several of the embodiments discussed herein address these issues by securing the suture lock within the retaining member, thereby creating a pivot point for the sutures that is relatively stationary relative to the anchor. This can be particularly beneficial during adjustment of the sutures as the physician creates the prosthetic chord. Securing the suture lock to the anchor (e.g., with the retaining member) can substantially eliminate that upward movement of the suture lock during adjustment.

Furthermore, having a stationary pivot point can enable more direct correlations between adjustments of a proximal portion of the suture (i.e., pulling on a portion of the suture located near the physician) and resulting adjustments in the distal portion of the suture (i.e., the portion of the suture between the suture lock and the mitral valve). In particular, many of these embodiments discussed herein enable precise, bi-directional adjustment of the sutures in which movement of the guiding device (e.g., a catheter) directly translates into length change of the suture, e.g., between the leaflet and the suture lock. For example, if the guiding device is moved forward one millimeter, the suture is also moved forward one millimeter. This is referred to as "one to one motion." As one of skill in the art will readily understand from this disclosure, several embodiments discussed herein can enable one to one motion or near one to one motion under various conditions. In particular, PCT/US2017/069046 and PCT/US2019/021480, which is incorporated by reference herein, disclosed mechanisms to make a suture "pushable," including by placing a stiff tubular structure (i.e., a coil) over the suture. The stiffness provided by the coil allows the suture to be pushed similar to a cardiac guide wire. In this regard, the motion of the modified suture follows the motion of the guiding device (e.g., the catheter or the coil) in a "one to one" manner.

Stated differently, securing the suture lock within the retaining member can create fixed pivot point for the suture, such that the physician's movement of the suture external to the body will have a one-to-one correspondence with the movement of the suture between the suture lock and the leaflet. As a skilled artisan will readily appreciate, in some situations the one-to-one movement will be a near one-to-one movement due to other changes (e.g., slight elongation of the sutures or minor movement of the suture lock within the socket), which are substantially different in nature and degree from the suture lock movements at issue in, e.g., unconstrained embodiments. For example, the movement ratio could vary from 1:1 to approximately 1:0.95, 1:0.90, 1:0.85, 1:0.80, etc., down to 1:0.50.

Creating a fixed pivot point with the suture lock can create additional advantages. For example, when multiple sutures pass through the suture lock, each suture can be independently adjusted without substantially affecting the other sutures. In particular, with the suture lock secured within the retaining member, a first suture can be adjusted to the correct length. The physician can then begin to adjust a second suture without disturbing the adjustment of the first suture, since the suture lock will not move with the second suture.

Furthermore, in some embodiments a portion of a first suture is located between the outer surface of the suture lock and the inner surface of the socket. The forces provided by those surfaces will retain that portion of the first suture in place as the physician adjusts the second suture. This configuration provides additional advantages, as the physician does not need to maintain external tension on the first suture. Reducing or eliminating tension on the suture can reduce any elongation or other detrimental effects on the sutures.

In addition, the first suture can be cut without changing the location of the suture lock and without changing the length of the suture between the suture lock and the tissue. As a skilled artisan will appreciate, there may be some incremental movement (e.g., less than 5/1000th of an inch or less than 5/100th of an inch), which could be deemed less than a substantial change in location in this context.

Furthermore, in some embodiments the suture lock serves as a fixed pivot point located close to a target area of tissue (e.g., near the apex of the heart), which can increase the ease of installation.

In some embodiments multiple sutures are coupled to tissue(s) (e.g., one or more leaflets) and pass through the suture lock. Each suture has a length extending between the suture lock and the tissue(s). When the suture lock is placed into the retaining member, the sutures are held in place. Should a first suture need to be adjusted (e.g., decrease the length of the first suture between the suture lock and the tissue), the suture lock can be removed from the retaining member and the physician can pull on the first suture to reduce its length. However, the location of the suture lock remains relatively static during this adjustment (e.g., the suture lock moves no more than 1 mm.) As a result, the physician does not need to further adjust or readjust the other sutures. In some embodiments, the sutures can be adjusted while the suture lock is within the retaining member. The retaining member secures the suture lock, further reducing or eliminating movement of the suture lock during adjustment of a suture. For example, movement of the suture lock can be less than or equal to approximately 0.5 mm.

In some embodiments, the suture lock engaged in the retaining member is loose enough that the force of the leaflet on the suture (e.g., an ePTFE chord) is sufficient to pull the suture through the interface between the suture lock and the retaining member, around the nose of the suture lock, through the open clamping mechanism of the suture lock and back to the stiffened pushable portion of the suture assembly. Operable forces for this situation can vary from 0 N to approximately 2 N. In some embodiments, the forces may range from 0.15 N to 1.50 N.

In some embodiments, the physician pulls on the external portions of a suture to decrease the length of that suture between the suture lock and the leaflet. Should the physician wish to increase the length of the suture between the suture lock and the leaflet, the physician can release tension on the external portions of the suture, and the movement of the leaflet during the heart's natural cardiac cycle will pull on the suture. In some embodiments, the suture lock is placed into a first portion of the retaining member, where the forces acting on the sutures are small enough that the physician and the leaflet can effect changes in the length of the sutures between the suture lock and the leaflet, e.g., forces between 0 N to 2 N. At the same time, the securing forces provided by the retaining member prevent the suture lock from moving during these adjustments or restricts movement of the suture lock to around 0.5 mm.

In some embodiments, once the lengths of the sutures between the suture lock and the corresponding tissues are correct (e.g., MR is clinically reduced or eliminated), the suture lock is pressed into a second portion of the retaining member, where the retaining member can apply greater securing forces to the suture lock and the sutures. As a result, the forces provided by the leaflet will not cause the suture to move within the suture lock (or to move only by a small amount, e.g., around 0.5 mm), so that the length of the sutures between the suture lock and the tissues remains constant (or moves only by the amount of stretch provided by the sutures, e.g., approximately 10%). At this point, the physician can take a measured analysis of the placement and tension provided by the prosthetic chords. If satisfactory, the physician can engage the suture lock to clamp down on the sutures. In this configuration, the prosthetic chords can operate for at least 400 million cycles, i.e., about 10 years, or even at 800 million cycles or about 20 years. In certain example embodiments, the prosthetic chords can operate for at least 400 million cycles, i.e., 10 years, or even at 800 million cycles or 20 years.

In some embodiments, the sutures are permanently secured using only the restraining forces provided by the retaining member, either alone or in combination with the external surface of the suture lock. For example, the suture lock may lack any internal clamping or restraining mechanisms, instead providing an outer surface that, along with the inner surface of the retaining member, secures the sutures against further movement from the forces originating from the heart's natural cycles.

In some embodiments, the retaining member enables the suture lock to work with sutures of different sizes. For example, sutures of a larger size and/or thickness may be secured once the suture lock is inserted into a first portion of the retaining member. Sutures of a smaller size can also be secured, e.g., by pressing the suture lock deeper into the retaining member.

Embodiments of the present disclosure can provide further advantages that facilitate easy adjustment of the suture. For example, friction can create difficulties in adjusting the sutures, as well as the life and efficacy of the sutures. Some embodiments address this issue by using a suture lock having a tapered nose. For example, and as shown in FIG. 52, the distal end of the suture lock 4306 includes a tapered nose 4370. The outer surface of the suture lock 4306 has a cylindrical shape, and the outer surface of the nose portion 4370 likewise has a cylindrical shape whose radius decreases towards the distal end of the nose 4370.

The front surface of the nose portion 4370 presents an inner aperture surrounded by a ring of the tapered nose. In some embodiments, the diameter of the inner aperture can range from 1 mm to 3 mm. The thickness of the ring can range from 0.5 mm to 2.0 mm.

The tapered nose portion 4370 can facilitate insertion of the suture lock 4306 into the retaining member 4304. In some embodiments, the nose portion 4370 tapers more steeply while in other embodiments the nose portion 4370 tapers less steeply. In addition, or alternatively, the retaining member 4304 may include a proximal portion whose profile tapers outward to guide the suture lock 4306 into interior portions of the retaining member 4304. For example, the proximal end of the retaining member 4304 may have a larger radius than a middle portion of the retaining member

4304. As discussed above, an anchor suture 4310 can also be used to guide the suture lock 4306 down into the retaining member 4304.

As shown in FIG. 52, the interior surface of the nose portion 4370 can include a proximal portion whose thickness increases along a longitudinal line from the front portion to a middle portion. After that middle portion, the thickness of the nose portion decreases towards a distal portion. The proximal end of the nose portion may be configured to snap fit onto the suture lock body in some embodiments.

To facilitate bi-directional adjustment, certain embodiments reduce the frictional forces on the sutures via the suture lock and the retaining member. For example, the profile of the nose provides a rounded surface that facilitates movement of the suture around the nose without creating sharp edges that wear down the suture. In addition, the composition of the nose can include, e.g., PFA or other materials that further reduce friction between sutures and the nose.

The nose portion can be configured to accommodate multiple sutures simultaneously. At the same time, the tapered profile enables easier access into the retaining member. To take advantage of both of these features, the size of the aperture in the nose portion can correspond to the number of sutures to be used. For example, the diameter of the nose aperture may be 1 mm when two sutures are used, and the diameter of the nose aperture may be 2 mm when four sutures are used. Generally speaking, the ratio of diameter to number of sutures may be approximately 0.5 mm per suture. In some embodiments, different nose portions (e.g., nose portions with apertures of different sizes) may be interchangeably used with a single suture lock body. In other embodiments, the size of the suture lock (e.g., the diameter of the suture lock) is larger or smaller to accommodate different numbers of sutures.

In some embodiments, the retaining member is formed of an ePTFE material in which the fibrillar orientation of the film microstructure is oriented in a direction substantially parallel the longitudinal axis of the retaining member. In this manner, any longitudinal motion of the suture (e.g., an ePTFE suture) will be in line with the fibrillar orientation to further reduce friction and wear on the sutures. For example, in some embodiment, the retaining member (in whole or at least the interior surface) is formed of a substantially monolithic ePTFE covering having a node and fibril microstructure in which the nodes are oriented generally perpendicular to the longitudinal axis of the retaining member and the fibrils are oriented generally parallel to the longitudinal axis of the retaining member.

As discussed above, the retaining member engages the sutures and/or the suture lock. In some embodiments it is necessary to disengage the suture lock from the retaining member to allow slack into the sutures. This simplifies maintaining tension in one suture relative to another because it eliminates the length changes created through the catheter. In these embodiments the suture lock can be disengaged from the interference fit with the retaining member to add slack to the sutures. In other words, in some embodiments multiple sutures pass through the suture lock, which is inserted into the retaining member. As a result, the sutures are held in place between the outer surface of the suture lock and the interior surface of the retaining member. Should the physician need to adjust one of the sutures, the suture lock can be removed from the retaining member. At this stage, the suture at issue can be adjusted without significant upward movement of the suture lock. Accordingly, adjustment of that suture does not significantly alter the tension in the other sutures.

In some embodiments, the retaining member serves as a prosthetic papillary muscle as part of the prosthetic chord. The materials selected for, e.g., the retaining member and the suture (as well as the anchor and/or suture lock) can be selected to promote tissue encapsulation, tissue ingrowth, and/or particular biological reactions.

Figure 55:
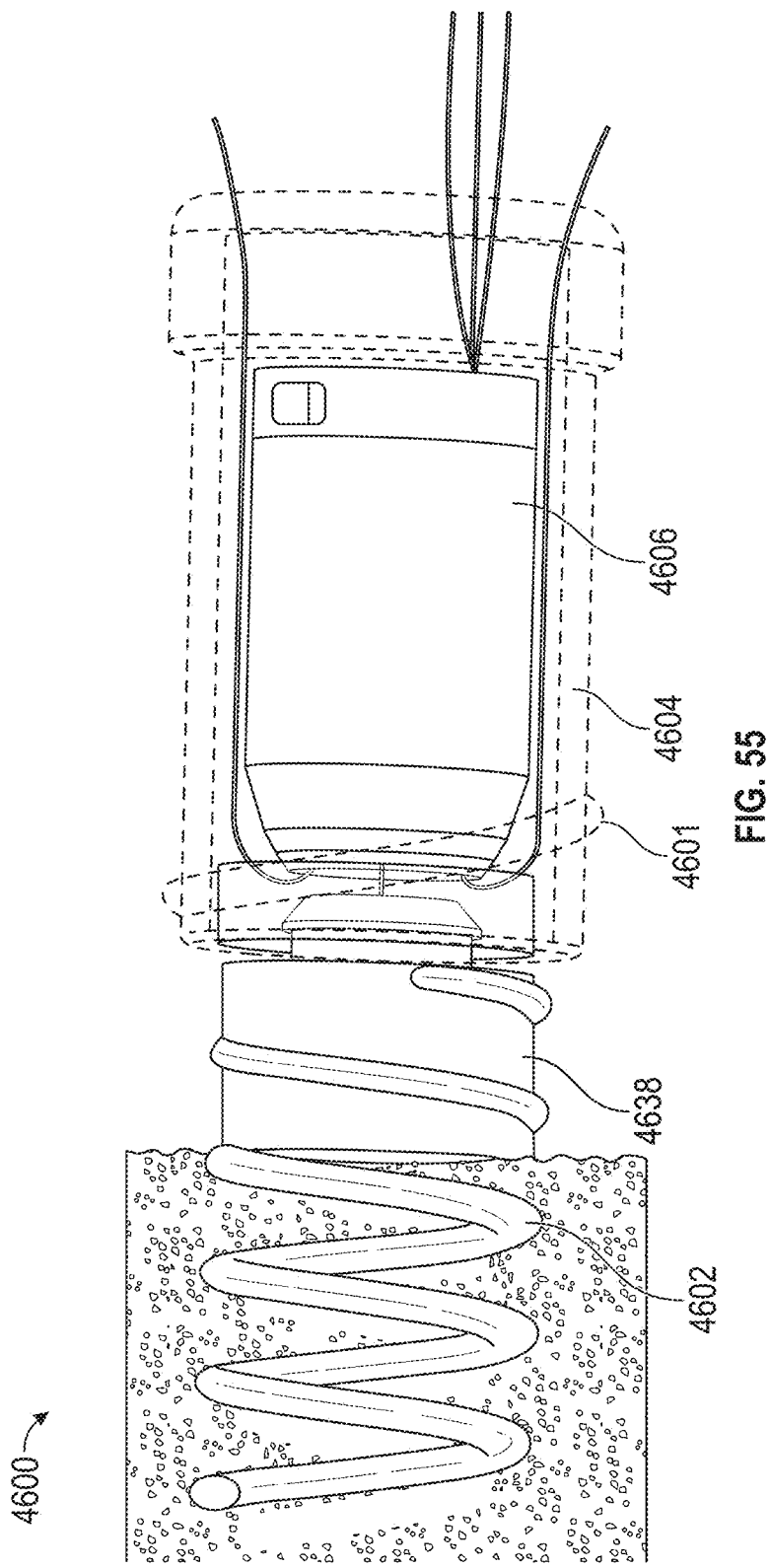
FIG. 55 illustrates an anchor, retaining member, and suture lock of a transcatheter mitral chordal repair system in which the anchor extends over an anchor hub, according to embodiments of the present disclosure, in accordance with an embodiment.

FIG. 55 illustrates another embodiment of a transcatheter mitral chordal repair system 4600. This system 4600 includes features similar to those shown in FIGS. 51 and 52. However, in this embodiment the retaining member 4604 does not include a support member. Instead, the anchor 4602 extends around the anchor hub 4638 at terminates at the lower surface of the retaining member 4604. A mechanical bond or joint 4601 secures the retaining member 4604 to the anchor hub 4638. The anchor 4602 and the anchor hub 4638 can be joined together in a manner as discussed above. In FIG. 55, the walls of the retaining member 4604 can be 25% to 100% thicker than the walls of the socket in FIGS. 51 and 52. Thicker walls can provide axial support to prevent buckling as the suture lock 4606 enters the retaining member 4604, while still being compliant enough to permit passage. A mechanical bond or joint secures the anchor hub 4638 to the retaining member 4604, which extends over the anchor hub 4638.

Figure 56:
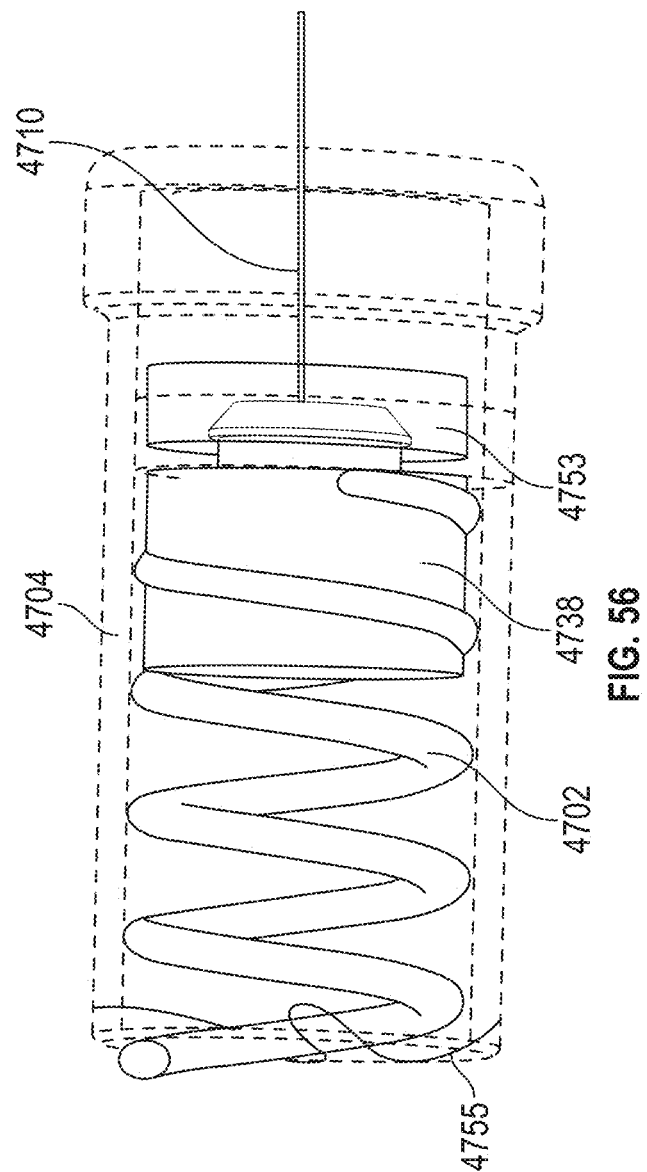
FIGS. 56, 57 and 58 illustrate an anchor, retaining member, and suture lock of a transcatheter mitral chordal repair system in which the anchor is advanced out of the retaining member and into adjacent tissue, in accordance with an embodiment.
Figure 57:
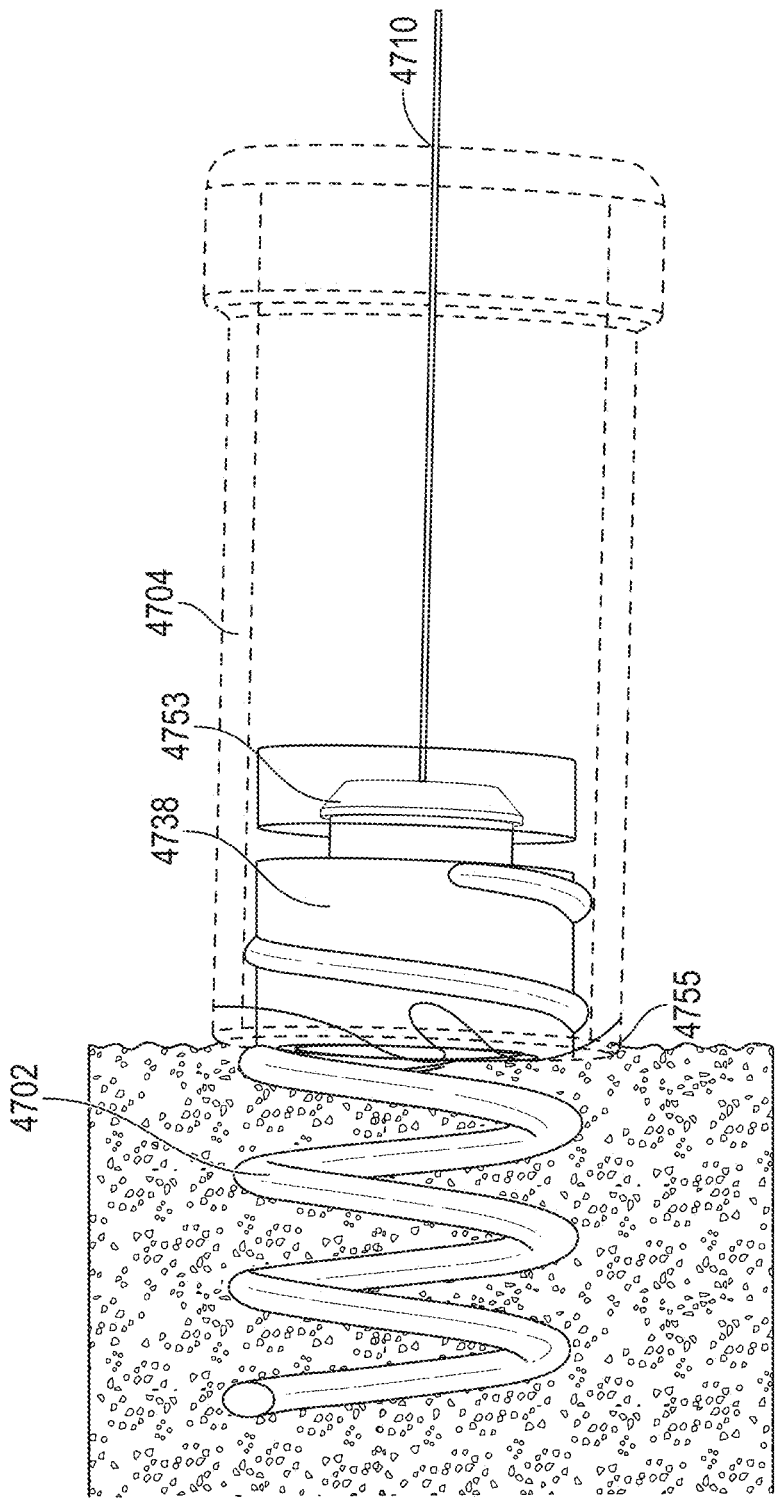
Figure 58:
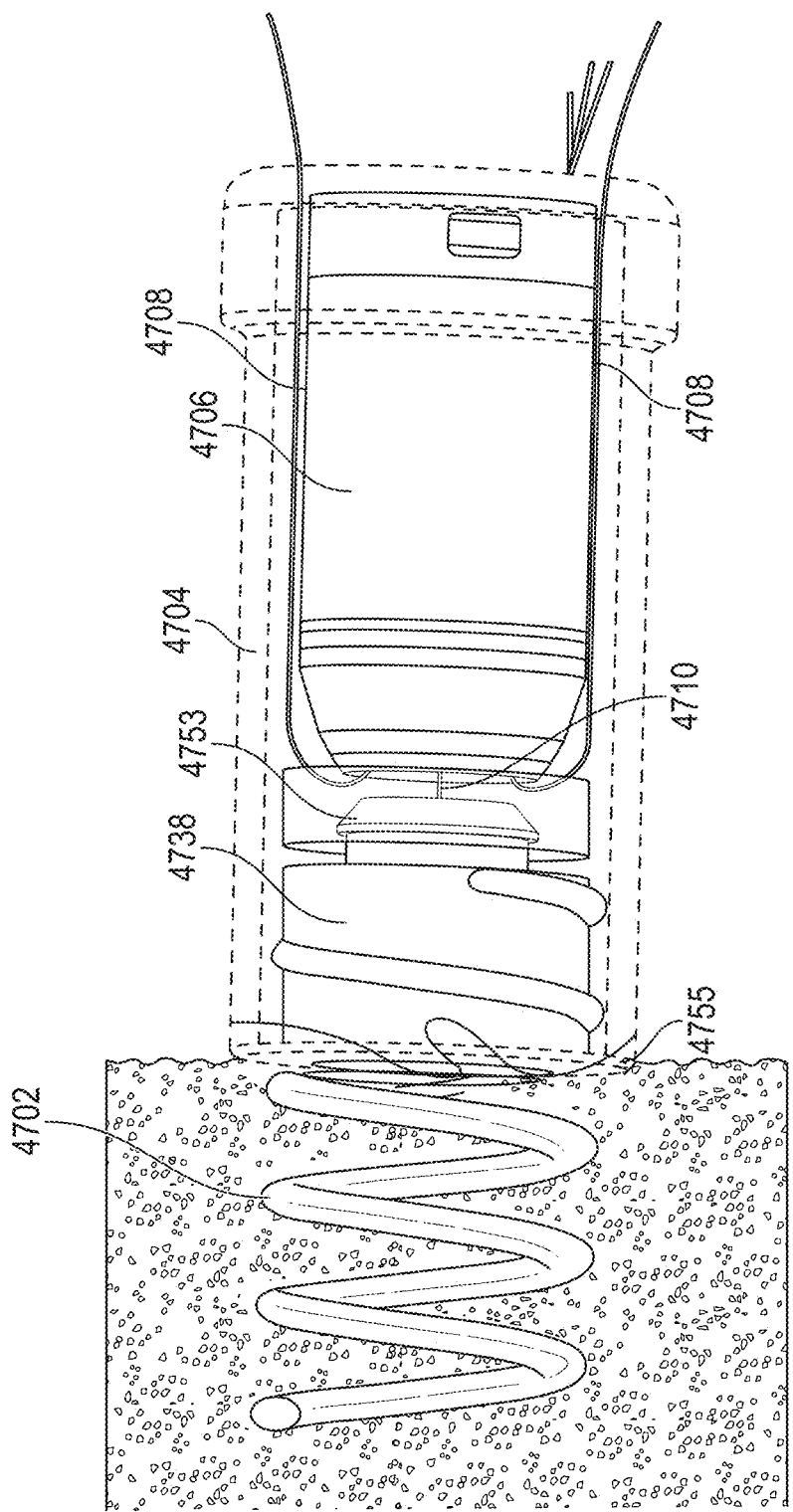

Some embodiments involve a method for transcatheter mitral chordal repair using a transcatheter mitral chordal repair system. During this process, the anchor and anchor socket are delivered together, e.g., via a delivery catheter. FIGS. 56-58 illustrate a method of deploying an anchor 4702, socket 4704, and suture lock 4706. In FIG. 56, the anchor 4702 is located within the socket 4704. In this configuration, both anchor 4702 and socket 4704 can be passed through a catheter and into the left ventricle (e.g., via the left atrium). In some embodiments, the anchor 4702 is fully retracted within the socket 4704 to prevent the anchor 4702 from contacting or piercing the catheter or other tissue. Once the socket 4704 is located against the ventricular wall, the anchor 4702 is advanced out of the socket 4704 and into the tissue. A socket attachment device 4755 captures the coil threads as the anchor 4702 emerges from the socket 4704, until the socket attachment device 4755 ultimately contacts the anchor hub 4738 to lock the anchor 4702 in place. In some embodiments, the socket attachment device 4755 is a suture with a loop or a series of loops through which the coil passes. In other embodiments, the socket attachment device 4755 is an extension of the socket material at the distal end of the socket 4704, this extension having a hole or series of holes through which the coil passes. In both these examples, extrusion of the coil through the hole or loop advances the coil until the socket attachment device 4755 is secured against the anchor hub 4738.

FIG. 57 illustrates the anchor 4702 and socket 4704 once the anchor 4702 is deployed into the ventricular tissue. A socket attachment device 4755 secures the anchor hub 4738 (and thus the anchor 4702) in place relative to the socket 4704. The suture lock 4706 is then advanced along the anchor suture 4710 into the socket 4704 until it contacts the bushing 4753, as shown in FIG. 58. Once the sutures 4708 are correctly tensioned, the suture lock 4706 can be activated and locks the sutures 4708 and the anchor suture 4710 in place. The suture lock 4706 is coaxially aligned with the anchor 4702, in parallel with the sutures 4708 that are pinned between the outer surface of the suture lock 4706 and the inner surface of the socket 4704. The sutures 4708 are also pinned between the curved nose of the suture lock 4706 and the bushing 4753.

Figure 59:
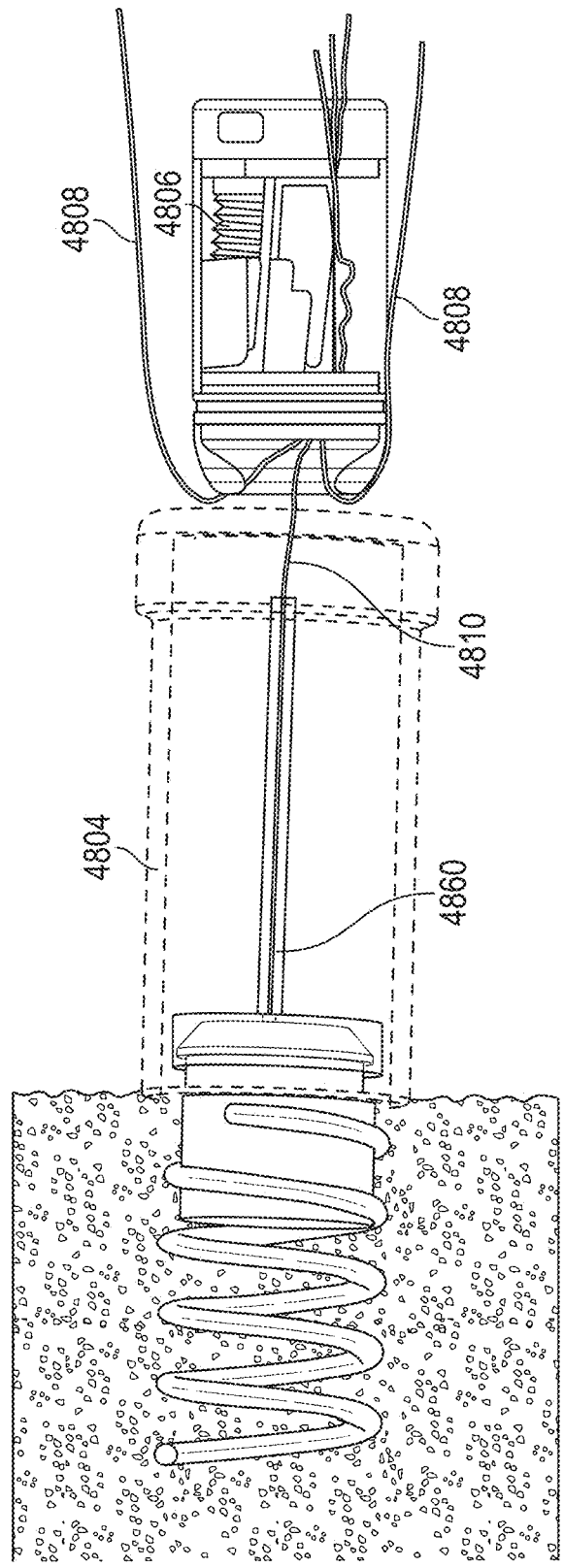
FIGS. 59 and 60 illustrate an anchor, retaining member, and suture lock of a transcatheter mitral chordal repair system in which an anchor pledget is located between the suture lock and the anchor hub, according to aspects of the present disclosure, in accordance with an embodiment.
Figure 60:
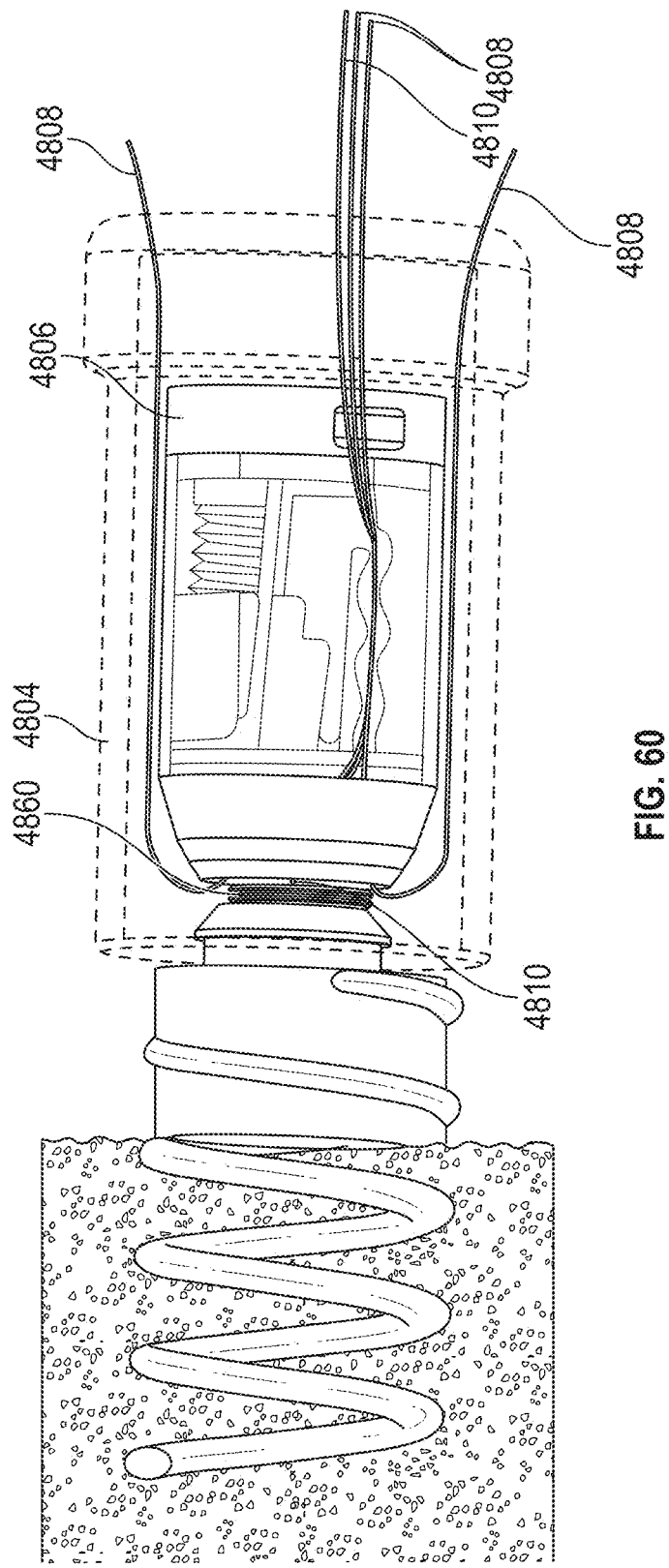

FIGS. 59 and 60 illustrate another embodiment of a transcatheter mitral chordal repair system 4800. This system can include features similar to those shown in FIGS. 51 and 52. In this embodiment, an anchor pledget 4860 is incorporated into the anchor suture 4810. As the suture lock 4806 is advanced into the socket 4804, the anchor pledget 4860 collapses to create a bushing in between the anchor hub 4838 and suture lock 4806. The suture lock 4806 can selectively engage the sutures 4808 coupled to leaflets and remaining portions of the anchor suture 4810.

Figure 61:
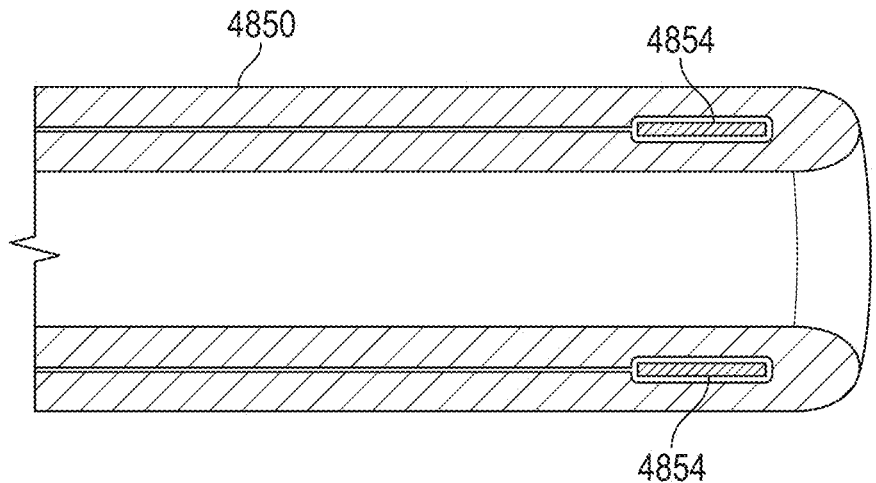
FIG. 61 illustrates a side cutaway view of a retaining member, according to aspects of the present disclosure, in accordance with an embodiment.

FIG. 61 illustrates a socket formed of densified ePTFE 4850. In some embodiments the socket is formed of ePTFE. The socket can be formed by folding a tube back on itself, creating two layers. This reinforces the socket to resist axial compression and folding as the suture lock enters the socket. In some embodiments, the retaining member is made from a thick-wall graft material. To increase the axial stiffness, the thick wall graft material can be densified. An example of this is shown in FIG. 61, depicting a graft material that has been rolled to obtain the proper thickness and density. Furthermore, the resulting two-layer construct increases densified pliability.

Figure 62:
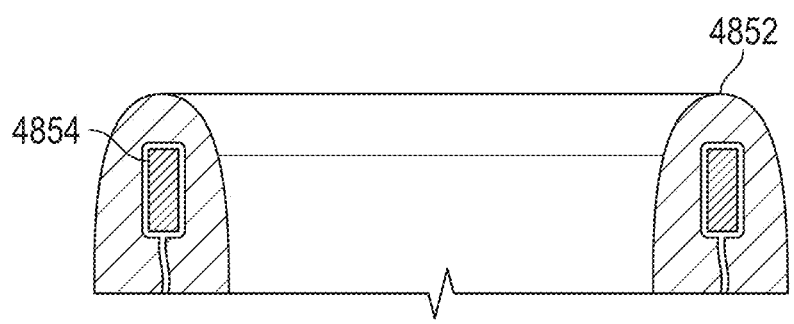
FIG. 62 illustrates a side cutaway view of an upper portion of a retaining member, according to aspects of the present disclosure, in accordance with an embodiment.

FIG. 62 illustrates a "rolled" end 4852 of the PTFE socket. In some embodiments the socket is formed of ePTFE. The marker band 4854 is placed on the exterior surface of the tube before it is rolled, located so that the band is placed between the two rolled layers at the top of the socket. This band can be a radiopaque band. In some embodiments, the retaining member includes an end portion whose radial stiffness is different than other portions. For example, the proximal portion of a retaining member can be formed with an increased radial stiffness. In some embodiments, a marker band is placed between layers of the graft material as it is rolled to form the retaining member, as shown in FIG. 62. This marker band increases the radial stiffness and makes this portion of the retaining member radiopaque. In some embodiments, the marker band is retained between the two layers of PTFE or ePTFE and densified into the PTFE or ePTFE structure.

Figure 63:
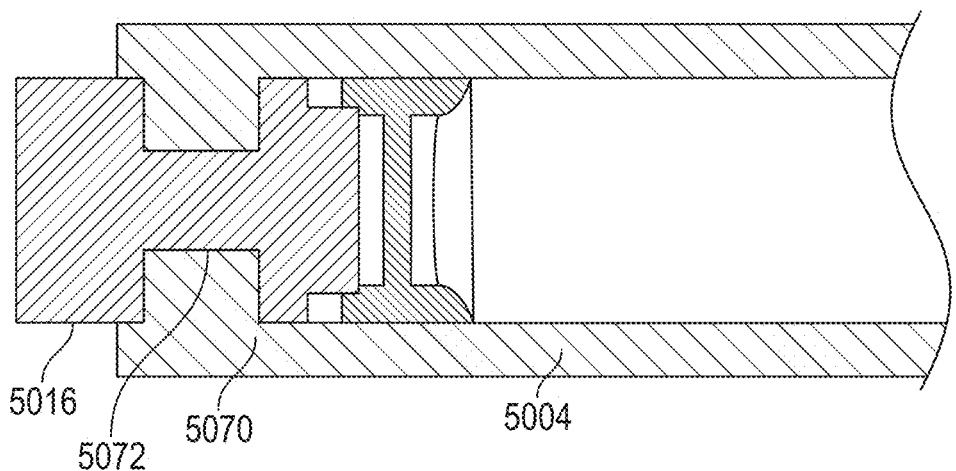
FIG. 63 illustrates a retaining member including a densified portion that secures an anchor hub, aspects to embodiments of the present disclosure, in accordance with an embodiment.
Figure 64:
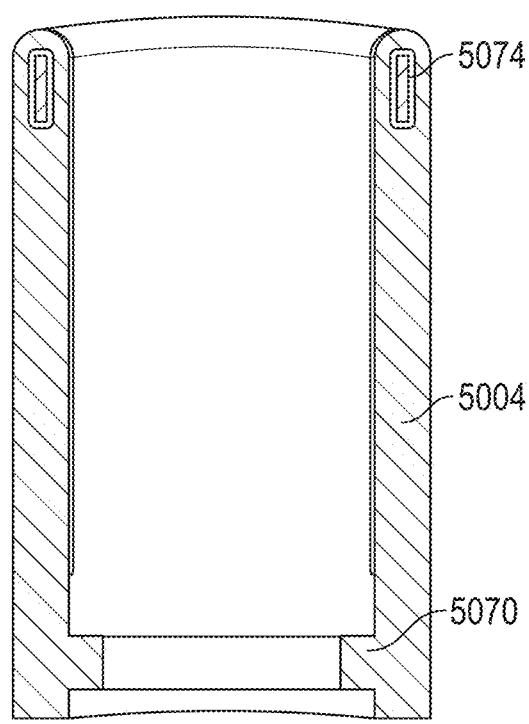
FIG. 64 illustrates a cutaway view of the socket of FIG. 63, in accordance with an embodiment.

FIGS. 63 and 64 illustrate a densified PTFE socket 5004 designed to interface with an anchor hub 5016. In some embodiments the socket 5004 is formed of ePTFE. The densified PTFE or ePTFE socket 5004 includes a lower extension 5070 designed to fit around a corresponding groove 5072 in the anchor hub 5016. This secures the socket 5004 to the hub 5072. A radiopaque band 5074 is located near the top of the socket 5004. The densified PTFE or ePTFE can be used to keep retention of the anchor. As shown in FIG. 63, by pressing the PTFE or ePTFE into a retention ring on the anchor, it will be held in place. FIG. 64 illustrates an exemplary retaining member in which a marking band has been incorporated into a proximal portion while a distal portion include a densified portion designed to retain an anchor (not shown in FIG. 64).

Figure 65A:
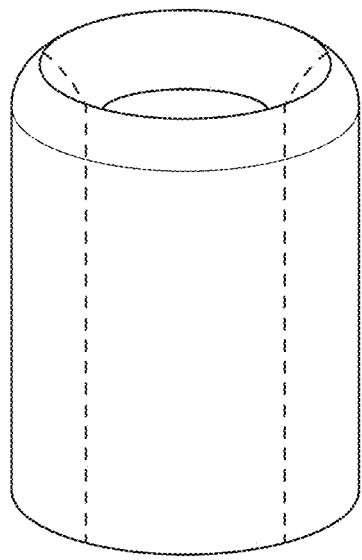
FIG. 65A illustrates a side perspective view of a socket, according to aspects of the present disclosure, in accordance with an embodiment.
Figure 65B:
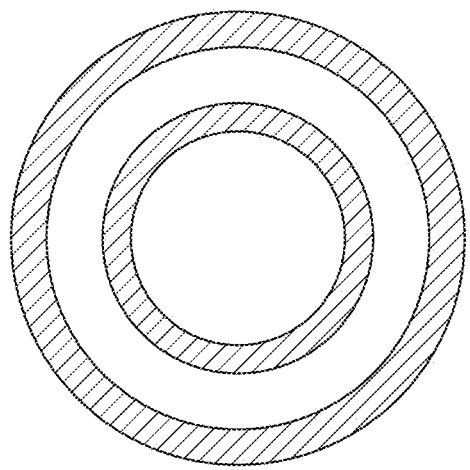
FIG. 65B illustrates a top cutaway view of the socket of FIG. 65A, in accordance with an embodiment.

FIGS. 65A and 65B illustrate a socket formed by inverting a vascular graft tube, creating an outside wall and an inside wall. This creates a socket from materials that are biocompatible. This material can be the same as the suture material, thereby minimizing or lessening wear of the sutures where they exist the socket. The direction of the fibrils of the socket surfaces can be oriented to match the direction of the fibrils of the suture to further minimize wear.

The various prosthetic chordae tendinae deployment systems discussed above can be used in many different medical applications. These embodiments can reduce or eliminate movement of the sutures relative to the suture lock as well as movement of the suture lock relative to the anchor. For example, in some embodiments an anchor is delivered into heart tissue, e.g., near the apex of the left ventricle or near a papillary muscle. As discussed above, the anchor can be delivered through a trans-septal catheter advanced into the left atrium and through the mitral valve. The anchor is a helical anchor and is coupled to a retaining member. In some embodiments, the anchor is initially delivered within the retaining member and is advanced out of the retaining member and into the heart tissue. An anchor suture is attached to the anchor (e.g., via an anchor hub). A leaflet anchor (e.g., pledget) is then delivered and attached to a leaflet of the mitral valve. In some embodiments, the pledget is located on the ventricle side of the leaflet with a pledget suture extending from the atrium side of the leaflet. In other embodiments, the pledget is located on the atrium side of the leaflet and the pledget suture extends from the ventricular side of the leaflet. Multiple pledgets and sutures may be placed in one or more leaflets.

To affect the prosthetic chordae tendinae, in certain embodiments, a suture lock can be advanced over the anchor suture and the sutures. Specifically, the proximal ends of the sutures enter through an aperture in the suture lock and pass through the suture lock. The suture lock is advanced towards the retaining member, guided by the suture anchor. Because the suture lock is radiopaque, and because the retaining member can include a radiopaque band near its proximal surface, the physician can use imaging technology to confirm the location of the suture lock relative to the retaining member. Furthermore, the use of a radiopaque band in the retaining member enables the physician to confirm once the suture lock has been fully inserted into the retaining member.

In certain embodiments, once the suture lock reaches the retaining member, the physician can adjust the length of the sutures between the suture lock and the leaflet to effect each new prosthetic chordae tendinea. In some embodiments, some or all of this adjustment is made with the suture lock at or in the retaining member. In certain embodiments, any movement of the sutures can result in one-to-one movement or near one-to-one movement of the suture distal of the suture lock, as the suture lock is maintained in a relatively constant position at the retaining member. For example, the ratio of proximal suture movement to distal suture movement can be from 0.5 to 1.0.

In some embodiments, this adjustment is made with the suture lock just outside of the retaining member, with the physician holding the suture lock in place and holding the sutures in tension. In other embodiments, this adjustment is made with the suture lock in the retaining member (either in a proximal portion of the retaining member or into a distal portion of the retaining member adjacent the anchor hub). In these embodiments, the retaining member holds the suture lock in place but enables the sutures to slide through the suture lock. The physician does not need to hold the suture lock in place.

Furthermore, in some embodiments the restraining force of the retaining member can be sufficient to hold the sutures in place against the forces exerted by the leaflet, and yet permit the sutures to slide in response to pulling forces from the physician. In these embodiments, the physician does not need to hold the suture lock in place and also does not need to hold each suture in tension. Instead, the retaining member maintains the tension of the distal portion of the pledget suture (i.e., the portion of the pledget suture distal of the retaining member and extending to the leaflet). This allows the physician to individually adjust each pledget suture, and any inadvertent movement of the catheter (e.g., accidental bumping) will not affect the sutures. Of course, the adjustments by the physician in this situation are in one direction (i.e., shortening the length of suture between the suture lock and the pledget). Should the physician need to increase the length of the suture between the suture lock and the pledget, the physical can remove the suture lock from the suture so that movement by the leaflets will again pull the sutures through the suture lock.

Once the sutures are appropriately tightened, the physician can lock the sutures in place using the suture lock, e.g., using the techniques described herein and/or in PCT/US2017/069046 and PCT/US2019/021480. In other embodiments, the retaining member locks the sutures in place without the need for an additional locking mechanism within the suture lock. The physician can then cut the excess suture (e.g., the suture located proximally of the retaining member). Because the sutures are not in tension proximal of the retaining member, cutting these sutures will not cause significant movement of the suture lock and/or the sutures located between the suture lock and the leaflets.

In other embodiments, the retaining member and the suture lock are integrated and are delivered as a unit. In some embodiments, that unit includes the anchor or is coupled to the anchor during the delivery process. The physician can adjust the length of the sutures extending between the suture lock and the leaflets and can using the suture lock to permanently lock the sutures in place.

The resulting prosthetic chordae tendinae in these embodiments can be more durable than prior prosthetic chordae tendinae. First, movement of the sutures relative to the suture lock is reduced or eliminated, reducing the wear of the sutures. Second, movement of the suture lock relative to the anchor is reduced or eliminated, further reducing the wear of the sutures. The orientation of the sutures relative to the suture lock also reduces suture wear. Additional features discussed above (including, e.g., the nose portion of the suture lock) increases the lifetime of the prosthetic chordae tendinae.

Figure 66:
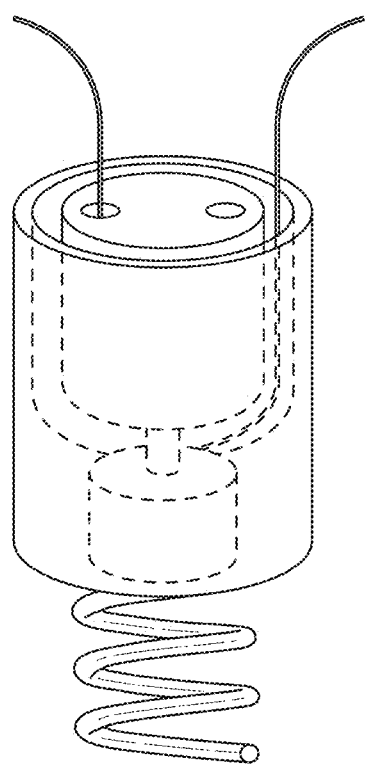
FIG. 66 is a schematic illustration of an anchor, retaining member, and suture lock according to aspects of the present disclosure, in accordance with an embodiment.
Figure 67:
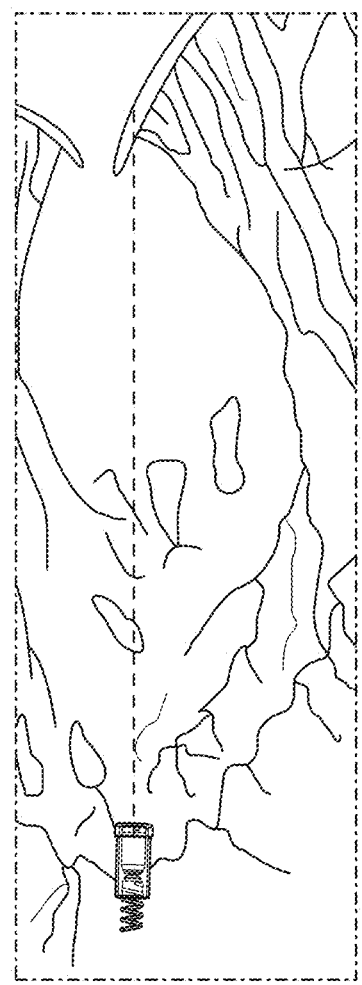
FIG. 67 illustrates an orientation of a prosthetic chord, according to aspects of the present disclosure, in accordance with an embodiment.

FIG. 66 illustrates an anchor, retaining member, and suture lock according to aspects of the present disclosure. FIG. 67 illustrates an orientation of a prosthetic chord, according to aspects of the present disclosure.

Suture Lock Boot

In certain aspects described herein, once the tension and length of the neo chordae implant is optimized, the suture lock can locked to fix the length of the sutures such that the sutures no longer move with respect to the suture lock.

In further aspects of the disclosure, after tensioning of the sutures by the physician to correct or minimize the mitral valve defect, the sutures can be clamped or pinned or otherwise engaged and locked in the suture lock so that the applied length adjustment and tension of the sutures is retained. With this step and resulting lock engagement, the mitral defect can be corrected or minimized and remains corrected throughout the functional lifetime of the neo chordae (i.e., the prosthetic chord). In order to advance the suture lock through the delivery catheter and to clamp or pin the sutures within the suture lock, the suture lock can be coupled to a lock driver mechanism that allows the physician to provide the necessary force to clamp or otherwise lock the sutures within the suture lock, i.e., a lock driver, such as lock screw driver in one alternative embodiment, for example, a stored energy mechanism, or the like, depending on the tightening requirements of the suture lock.

Figure 68:
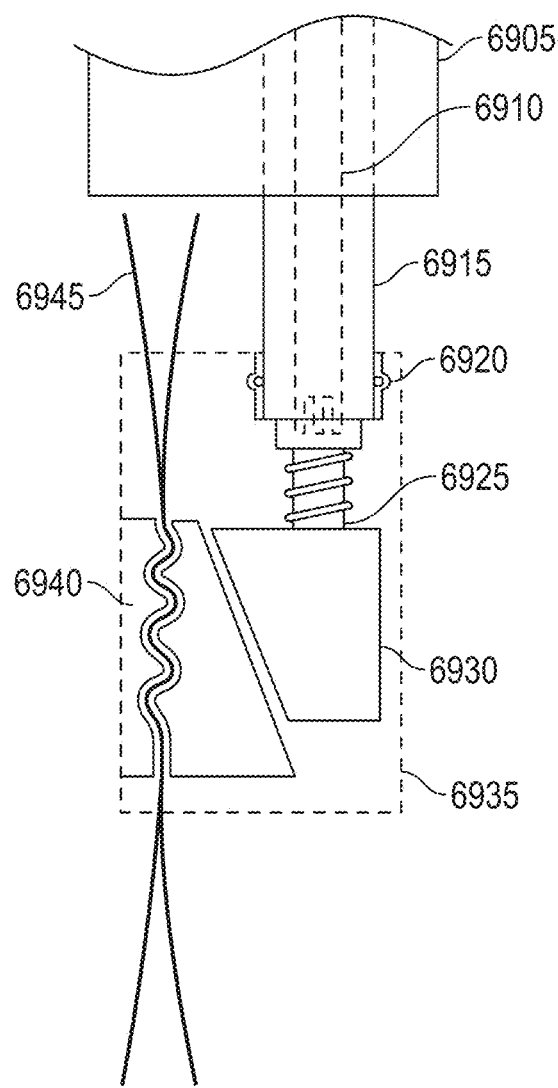
FIG. 68 is a side perspective view of a suture lock and lock driver mechanism in accordance with embodiments of the present disclosure, in accordance with an embodiment.

In some aspects, the suture lock may further be coupled to a boot located on or with the lock driver, wherein the boot comprises a retaining mechanism configured to reversibly retain the suture lock to the boot to enhance engaging of the lock driver. According to some embodiments and as shown, for example, in FIG. 68, the system comprises delivery catheter 6905, suture lock 6935 and boot 6915. Also shown in FIG. 68, suture lock 6935 includes screw 6925 which engages with lock driver 6910, wherein the lock driver can be rotated in order to advance or retract ramp (or push wedge) 6930, thereby clamping sutures 6945 against an opposing internal surface of the suture lock 6940. Suture lock 6935 is coupled to boot 6915. Lock driver 6910 (shown by dotted lines) is engaged with the screw head of screw 6925. The insertion of lock driver 6910 coaxially through boot 6915 can force suture lock retaining member 6920 (two suture lock retaining members 6920 are shown in FIG. 68, on opposite sides of boot 6915 from each other) to protrude from the outer surface of boot 6915. The suture lock retaining member 6920 can provide a frictional fit (not shown) to the suture lock 6935 or can engage one or more indentations (shown in dotted perspective view) in the suture lock 6935. In an alternative embodiment, a frictional fit between the lock driver and the boot alone may be used, without the requirement for suture lock retaining member(s) or indentation(s). Provided that the lock driver 6910 is positioned at a position that is distal to the suture lock retaining member 6920, then the suture lock retaining member 6920 of the boot 6915 will couple with the suture lock 6935 to restrict or eliminate movement of the suture lock 6935 relative to the boot 6915. Once the physician has tensioned the sutures to correct the movement of the mitral valve, the physician can then rotate the lock driver 6910 to clamp or pin the sutures within the suture lock 6935. It would be apparent to one of skill in the art than alternative suture lock clamping or locking configurations are within the scope of the present disclosure, such as either pushing or pulling components together to engage the locking of the suture lock.

Once the sutures have been clamped within the suture lock, the physician can use any known visualization technique in order to confirm that the mitral valve defect has been corrected or minimized. If, for example, further adjustments need to be made, the lock driver 6910 can be rotated in order to lessen the force on the sutures 6945 and adjust the tension as needed and repeat the procedure to clamp the sutures. Upon confirmation that the mitral valve defect has been corrected or minimized, lock driver 6910 can be retracted, thereby disengaging from the screw head of screw 6925.

Figure 69:
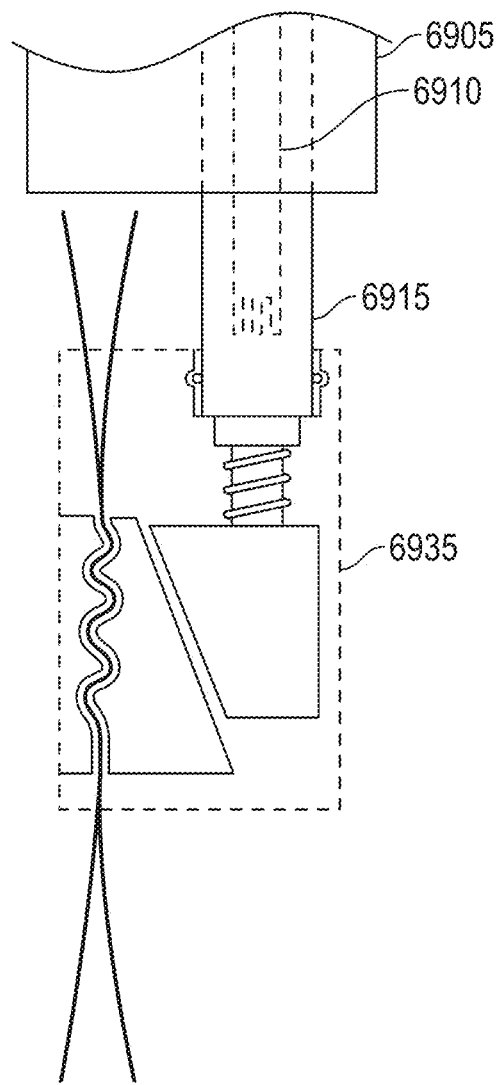
FIG. 69 is a side perspective view of a suture lock after tightening and initial dis-engagement of a lock driver mechanism and boot in accordance with aspects of the present disclosure, in accordance with an embodiment.
Figure 70:
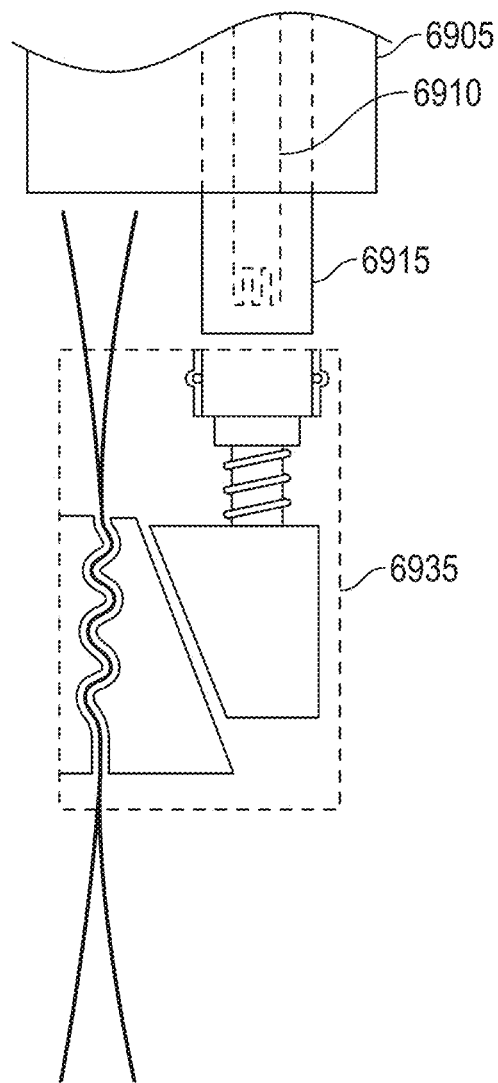
FIG. 70 is a side perspective view of the configuration of FIG. 69 upon further dis-engagement of the lock driver and boot in accordance with aspects of the present disclosure, in accordance with an embodiment.

FIGS. 69 and 70 depict removing the lock driver 6910 and the boot 6915 from the suture lock 6935. As lock driver 6910 is retracted from the suture lock and past the suture lock retaining member, the suture lock retaining members retracts into the boot, thereby disengaging the boot 6915 from the suture lock. With the suture lock retaining members retracted, the boot 6915 can also disengage from the suture lock. Once the boot 6915 disengages the suture lock retaining member 6920 (not shown) from the suture lock 6935, the physician can then remove the lock driver 6910 and the boot 6915 from the catheter.

In some embodiments, the anchor may further comprise a retaining member configured to couple with the suture lock so that the suture lock maintains a positional relationship with the anchor. In these embodiments, the physician can apply pressure on the lock driver and the boot in order to insert the suture lock into the retaining member. Once the suture lock has been inserted into the retaining member and the sutures have been properly tensioned, then the sutures can be clamped in the suture lock, and the lock driver and the boot can be retracted from the suture lock and from the catheter as was discussed above.

The suture lock can further comprise alternative mechanisms configured to actuate the suture retaining mechanism. In some embodiments, the suture retaining mechanism can be a screw wherein the rotation of the screw can reversibly apply or remove pressure on the sutures. FIGS. 68-70 show embodiments wherein the suture retaining mechanism comprises a screw 6925, one or more ramps 6930 and a surface of the suture lock 6940. The ramp and/or the opposing surface of the suture lock can comprise a plurality of notches, each having a height that is advanced to clamp the sutures by the rotation of a screw. The height of each notch may increase or decrease from an innermost notch to an outermost notch. Other suture retaining mechanism such as, for example, a spring or other stored energy mechanism may be used to provide the force that clamps the sutures within the suture lock. The spring can be activated, for example, in any known way whereby stored energy of the spring could be released during the removal of the boot from the suture lock.

In certain arrangements, a suture can include a thread, cable, wire, filament, strand, line, yarn, gut, or similar structure, whether natural and/or synthetic, in monofilament, composite filament, or multifilament form (whether braided, woven, twisted, or otherwise held together).

Although this disclosure describes certain embodiments and examples, many aspects of the above-described systems and methods may be combined differently and/or modified to form still further embodiments or acceptable examples. All such modifications and variations are intended to be included herein within the scope of this disclosure. Indeed, a wide variety of designs and approaches are possible and are within the scope of this disclosure.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

The disclosure herein of any particular feature, aspect, method, property, characteristic, quality, attribute, element, or the like in connection with various embodiments can be used in all other embodiments set forth herein. Also, any methods described herein may be practiced using any device suitable for performing the recited steps.

Moreover, while components and operations may be depicted in the drawings or described in the specification in a particular arrangement or order, such components and operations need not be arranged and performed in the particular arrangement and order shown, nor in sequential order, nor include all of the components and operations, to achieve desirable results. Other components and operations that are not depicted or described can be incorporated in the embodiments and examples. For example, one or more additional operations can be performed before, after, simultaneously, or between any of the described operations. Further, the operations may be rearranged or reordered in other implementations. Also, the separation of various system components in the implementations described above should not be understood as requiring such separation in all implementations, and it should be understood that the described components and systems can generally be integrated together in a single product or packaged into multiple products.

In summary, various illustrative embodiments and examples are described herein. Although the systems and methods have been disclosed in the context of those embodiments and examples, this disclosure extends beyond the specifically disclosed embodiments to other alternative embodiments and/or other uses of the embodiments, as well as to certain modifications and equivalents thereof. This disclosure expressly contemplates that various features and aspects of the disclosed embodiments can be combined with, or substituted for, one another. Accordingly, the scope of this disclosure should not be limited by the particular disclosed embodiments described above, but should be determined only by a fair reading of the claims that follow as well as their full scope of equivalents.

What is claimed is:

1. A tissue anchor, comprising:
    a hub;
    a suture extending proximally from the hub;
    a helical anchor extending distally from the hub; and
    a secondary anchor axially moveable relative to the hub in a distal direction from a first configuration to a second, deployed configuration to engage tissue and inhibit unscrewing of the helical anchor.

2. The tissue anchor as in claim 1, wherein the secondary anchor comprises a tine that is carried by a support and extends between a proximal end and a sharpened distal end.

3. The tissue anchor as in claim 2, wherein the support comprises an annular structure.

4. The tissue anchor as in claim 2, wherein the support can receive a tubular structure of a deployment system for advancing the support distally with respect to the helical anchor.

5. The tissue anchor as in claim 2, wherein the hub includes a tine guide for axially moveably receiving the tine.

6. The tissue anchor as in claim 5, wherein the tine guide includes a deflection surface for deflecting the tine into a launch angle that inclines radially outwardly in the distal direction.

7. The tissue anchor as in claim 6, wherein the launch angle is within a range of 30 to 45 degrees.

8. The tissue anchor as in claim 1, wherein the hub includes an aperture for axially moveably receiving the secondary anchor.

9. The tissue anchor as in claim 1, further comprising a core wire attached to the hub and extending concentrically through the helical anchor, and a suture anchor guide extending proximally from the hub.

10. The tissue anchor as in claim 9, wherein in the second, deployed configuration the secondary anchor extends through the suture anchor guide.

11. The tissue anchor as in claim 10, wherein the secondary anchor extends through an aperture in the suture anchor guide.

12. The tissue anchor as in claim 11, wherein as the secondary anchor moves to the second, deployed configuration, the secondary anchor is operable to pierce the suture anchor guide.

13. The tissue anchor as in claim 12, wherein the core wire extends distally beyond the helical anchor.

14. The tissue anchor as in claim 1, further comprising a radiopaque marker carried by the secondary anchor.

15. The tissue anchor as in claim 1, further comprising a core wire attached to the hub and extending concentrically through the helical anchor, a radiopaque marker axially movably carried by the core wire, and a spring carried by the core wire.

16. The tissue anchor as in claim 15, further comprising a distal stop on the core wire operable to limit distal travel of the radiopaque marker.

17. The tissue anchor as in claim 1, further comprising a tissue piercing point on a distal end of the helical anchor, and a barb on the helical anchor, proximal to the point and configured to resist rotation of the helical anchor out of engagement with tissue.

18. The tissue anchor of claim 1, wherein the secondary anchor is operable to increase an anchor torque resistance of the tissue anchor by a factor between 2 to 5 as compared to an anchor torque resistance of the tissue anchor without the secondary anchor.

19. The tissue anchor of claim 1, wherein an anchor torque resistance of the helical anchor with the secondary anchor is between 2 N/cm to 5 N/cm.

20. The tissue anchor of claim 1, wherein the secondary anchor increases an anchor torque resistance of the helical anchor by at least a factor of 2 as compared to an anchor torque resistance of the tissue anchor without the secondary anchor.

* * * * *